United States Patent [19]

Hagen et al.

[11] Patent Number: 5,378,677
[45] Date of Patent: Jan. 3, 1995

[54] THIOCHROMENONE DERIVATIVES AS ANTIDOTES, AND HERBICIDES CONTAINING THEM

[75] Inventors: Helmut Hagen, Frankenthal; Peter Raatz, Ludwigshafen; Helmut Walter, Obrigheim; Andreas Landes, Limburgerhof, all of Germany

[73] Assignee: BASF Aktiengesellschaft, Ludwigshafen, Germany

[21] Appl. No.: 5,797

[22] Filed: Jan. 19, 1993

[30] Foreign Application Priority Data

Jan. 23, 1992 [DE] Germany .............................. 4201720

[51] Int. Cl.[6] .............................................. A01N 25/32
[52] U.S. Cl. .................................... 504/104; 504/105; 504/343
[58] Field of Search ............... 504/104, 105, 106, 108, 504/343, 313, 314, 315

[56] References Cited

U.S. PATENT DOCUMENTS

| | | | |
|---|---|---|---|
| 4,249,937 | 2/1981 | Iwataki et al. | 504/190 |
| 4,347,372 | 8/1982 | Fory et al. | 548/217 |
| 4,440,566 | 4/1984 | Luo | 504/313 |
| 4,614,745 | 9/1986 | Ilvespää et al. | 514/432 |
| 4,888,042 | 12/1989 | Arai et al. | 504/313 |

FOREIGN PATENT DOCUMENTS

| | | |
|---|---|---|
| 134198 | 3/1985 | European Pat. Off. |
| 459140 | 12/1991 | European Pat. Off. |
| 2014991 | 9/1979 | United Kingdom |
| 92/10498 | 6/1992 | WIPO |

OTHER PUBLICATIONS

*Research Disclosure;* Jul. 1976, No. 147.
Ann. Chem. 680 (1964), 40 et seq.

*Primary Examiner*—Richard L. Raymond
*Assistant Examiner*—Brian G. Bembenick
*Attorney, Agent, or Firm*—Keil & Weinkauf

[57] ABSTRACT

Herbicidal agents containing at least one thiochromenone of the formula I

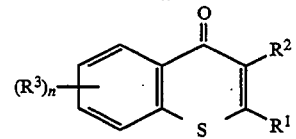

where
n is 1, 2, 3 or 4, and the radicals $R^3$ may have different meanings when n is $>1$;
$R^1$ is hydrogen; cyano; halogen; substituted or unsubstituted alkyl, aryl or hetaryl;
a group $-XR^4$ or a group $-COYR^4$, where
X is oxygen, sulfur and $NR^5$,
Y is oxygen and $NR^5$,
$R^4$ is one of the following groups:
hydrogen; formyl; alkyl; cycloalkyl; alkylcarbonyl; cycloalkylcarbonyl; alkylsulfonyl; cycloalkylsulfonyl;
substituted or unsubstituted aryl, hetaryl, arylcarbonyl, hetarylcarbonyl, arylsulfonyl or hetarylsulfonyl;
and
$R^5$ is hydrogen or substituted or unsubstituted alkyl, aryl or hetaryl;
$R^2$ is hydrogen; cyano; nitroso; nitro; halogen; substituted or unsubstituted alkyl, alkoxy, alkylthio, aryl or hetaryl;
a group $-NR^4R^5$ or a group $-COYR^4$, where
Y, $R^4$ and $R^5$ have the above meanings;
$R^3$ is hydrogen; cyano; halogen; substituted or unsubstituted alkyl, aryl or hetaryl;
a group $-YR^4$, a group $-COYR^4$, a group $-COR^6$ or a group $-SO_2R^7$, where
Y and $R^4$ have the above meanings;
$R^6$ is one of the following groups:
hydrogen; alkyl; cycloalkyl; substituted or unsubstituted aryl or hetaryl;
and
$R^7$ is hydrogen; alkyl; cycloalkyl; substituted or unsubstituted aryl or hetaryl;
or a group $-NR^4R^5$, where $R^4$ and $R^5$ have the above meanings,
and the plant-tolerated salts of those compounds I in which one or several of the substituents denote an acidic or basic group,
and at least one herbicidal active ingredient.

13 Claims, No Drawings

THIOCHROMENONE DERIVATIVES AS ANTIDOTES, AND HERBICIDES CONTAINING THEM

The present invention relates to herbicides containing at least one substituted thiochromenone of the formula I

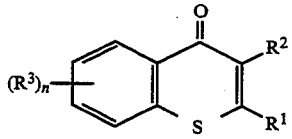

where
n is 1, 2, 3 or 4, and the radicals $R^3$ may have different meanings when n is $>1$;
$R^1$ is hydrogen; cyano; halogen; unsubstituted or substituted alkyl, aryl or hetaryl;
—$XR^4$ or —$COYR^4$, in which
X is oxygen, sulfur or $NR^5$,
Y is oxygen or $NR^5$,
$R^4$ is one of the following groups:
  hydrogen; formyl; alkyl; cycloalkyl; alkylcarbonyl; cycloalkylcarbonyl; alkylsulfonyl; cycloalkylsulfonyl; unsubstituted or substituted aryl, hetaryl, arylcarbonyl, hetarylcarbonyl, arylsulfonyl or hetarylsulfonyl, and
$R^5$ is hydrogen or unsubstituted or substituted alkyl, aryl or hetaryl;
$R^2$ is hydrogen; cyano; nitroso; nitro; halogen; unsubstituted or substituted alkyl, alkoxy, alkylthio, aryl or hetaryl;
—$NR^4R^5$ or —$COYR^4$, in which
Y, $R^4$ and $R^5$ have the abovementioned meanings;
$R^3$ is hydrogen; cyano; halogen; unsubstituted or substituted alkyl, aryl or hetaryl; —$YR^4$, —$COYR^4$, —$COR^6$ or $SO_2R^7$, in which
Y and $R^4$ have the abovementioned meanings;
$R^6$ is one of the following groups:
hydrogen; alkyl; cycloalkyl; unsubstituted or substituted aryl or hetaryl, and
$R^7$ is hydrogen; alkyl; cycloalkyl; unsubstituted or substituted aryl or hetaryl,
or —$NR^4R^5$ in which $R^4$ and $R^5$ have the abovementioned meanings,
and the plant-tolerated salts of the compounds I in which one or more of the substituents is an acidic or basic group,
and at least one herbicidal active ingredient.

Particularly suitable herbicidal active ingredients are compounds selected from
A) the group consisting of the cyclohexenone derivatives of the general formula II

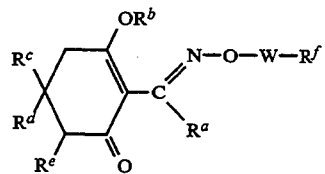

where
$R^a$ is $C_1$-$C_6$-alkyl;
$R^b$ is hydrogen, one equivalent of an agriculturally suitable cation, $C_2$-$C_8$-alkylcarbonyl, $C_1$-$C_{10}$-alkylsulfonyl, $C_1$-$C_{10}$-alkylphosphonyl or benzoyl, benzenesulfonyl or benzenephosphonyl, where the three last-mentioned groups may furthermore each carry from 1 to 5 halogen atoms;
$R^c$ is hydrogen, cyano, formyl, $C_1$-$C_6$-alkyl, $C_1$-$C_{14}$-alkoxy-$C_1$-$C_6$-alkyl, $C_1$-$C_4$-alkylthio-$C_1$-$C_6$-alkyl, phenoxy-$C_1$-$C_4$-alkyl, phenylthio-$C_1$-$C_6$-alkyl, pyridyloxy-$C_1$-$C_6$-alkyl, pyridylthio-$C_1$-$C_6$-alkyl, where the phenyl and pyridyl rings may each furthermore carry from one to three radicals selected from the group consisting of nitro, cyano, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio, $C_3$-$C_6$-alkenyl, $C_3$-$C_6$-alkenyloxy, $C_3$-$C_6$-alkynyl, $C_3$-$C_6$-alkynyloxy and —$NR^gR^h$, in which
$R^g$ is hydrogen, $C_1$-$C_4$-alkyl, $C_3$-$C_6$-alkenyl, $C_3$-$C_6$-alkynyl, $C_1$-$C_6$-acyl or benzoyl which may carry from one to three radicals selected from the group consisting of nitro, cyano, halogen, $C_1$-$C_4$-alkyl, partially or completely halogenated $C_1$-$C_4$-alkyl, $C_1$-$C_4$-alkoxy and $C_1$-$C_4$-alkylthio, and
$R^h$ is hydrogen, $C_1$-$C_4$-alkyl, $C_3$-$C_6$-alkenyl or $C_3$-$C_6$-alkynyl;
$C_3$-$C_7$-cycloalkyl or $C_5$-$C_7$-cycloalkenyl, where these groups may furthermore carry from one to three radicals selected from the group consisting of hydroxyl, halogen, $C_1$-$C_4$-alkyl, partially or completely halogenated $C_1$-$C_4$-alkyl, $C_1$-$C_4$-alkoxy, $C_1$-$C_4$-alkylthio, benzylthio, $C_1$-$C_4$-alkylsulfonyl, $C_1$-$C_4$-alkylsulfenyl and $C_1$-$C_4$-alkylsulfinyl, a 5-membered saturated heterocyclic structure which contains one or two oxygen or sulfur atoms or one oxygen and one sulfur atom as hetero atoms and which may furthermore carry from one to three radicals selected from the group consisting of $C_1$-$C_4$-alkyl, partially or completely halogenated $C_1$-$C_4$-alkyl, $C_1$-$C_4$-alkoxy and $C_1$-$C_4$-alkylthio, a 6-membered or 7-membered saturated or mono- or diunsaturated heterocyclic structure which contains one or two oxygen or sulfur atoms or one oxygen and one sulfur atom as hetero atoms and which may furthermore carry from one to three radicals selected from the group consisting of hydroxyl, halogen, $C_1$-$C_4$-alkyl, partially or completely halogenated $C_1$-$C_4$-alkyl, $C_1$-$C_4$-alkoxy and $C_1$-$C_4$-alkylthio, a 5-membered heteroaromatic structure containing from one to three hetero atoms selected from the group consisting of one or two nitrogen atoms and one oxygen or sulfur atom, where the heteroaromatic structure may furthermore carry from one to three radicals selected from the group consisting of cyano, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio, $C_2$-$C_6$-alkenyl, $C_2$-$C_6$-alkenyloxy, $C_3$-$C_6$-alkynyloxy and $C_1$-$C_4$-alkoxy-$C_1$-$C_4$-alkyl, phenyl or pyridyl, each of which may furthermore carry from one to three radicals selected from the group consisting of nitro, cyano, formyl, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio, $C_3$-$C_6$-alkenyl, $C_3$-$C_6$-alkenyloxy, $C_3$-$C_6$-alkynyl, $C_3$-$C_6$-alkynyloxy and —$NR^kR^l$, where $R^k$ and $R^l$ have the abovementioned meanings;
$R^d$ is hydrogen or hydroxyl or, when $R^c$ is $C_1$-$C_6$-alkyl, $R^d$ is $C_1$-$C_6$-alkyl;

$R^e$ is hydrogen, halogen, cyano, $C_1$–$C_4$-alkoxycarbonyl or a $C_1$–$C_4$-alkylketoxime group;

W is a $C_1$–$C_6$-alkylene, $C_3$–$C_6$-alkenylene or $C_3$–$C_6$-alkynylene chain, each of which may furthermore carry from one to three radicals selected from the group consisting of from one to three $C_1$–$C_3$-alkyl substituents, from one to three halogen atoms and one methylene substituent;

a $C_3$–$C_6$-alkylene or $C_4$–$C_6$-alkenylene chain, both of which may furthermore carry from one to three $C_1$–$C_3$-alkyl radicals and in each case a methylene group of the chains may be substituted by oxygen, sulfur, sulfoxyl, sulfonyl or a group —N($R^i$)—, in which $R^i$ is hydrogen, $C_1$–$C_4$-alkyl, $C_3$–$C_6$-alkenyl or $C_3$–$C_6$-alkynyl;

$R^f$ is hydrogen; vinyl;

a group —CH=CH—Z, in which Z is cyano, halogen, $C_1$–$C_4$-alkyl, partially or completely halogenated $C_1$–$C_4$-alkyl, $C_3$–$C_6$-cycloalkyl which in turn may furthermore carry from one to three substituents selected from the group consisting of hydroxyl, halogen, $C_1$–$C_4$-alkyl, partially or completely halogenated $C_1$–$C_4$-alkyl and $C_1$–$C_4$-alkoxy; carboxyl, $C_1$–$C_8$-alkoxycarbonyl, benzyloxycarbonyl, phenyl, thienyl or pyridyl, where these three aromatic radicals may each furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and $C_3$–$C_6$-cycloalkyl, where the cycloalkyl substituent in turn may furthermore carry from one to three radicals selected from the group consisting of halogen, $C_1$–$C_4$-alkyl, partially or completely halogenated $C_1$–$C_4$-alkyl and $C_1$–$C_4$-alkoxy;

ethynyl which may carry one of the following radicals:
$C_1$–$C_4$-alkyl or $C_3$–$C_6$-cycloalkyl, both of which may furthermore carry from one to three substituents selected from the group consisting of hydroxyl, halogen, $C_1$–$C_4$-alkyl, partially or completely halogenated $C_1$–$C_4$-alkyl and $C_1$–$C_4$-alkoxy, or phenyl, thienyl or pyridyl, where each of the aromatic radicals may furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy and $C_1$–$C_4$-alkylthio;

phenyl, halophenyl, dihalophenyl, a 5-membered heteroaromatic group having from one to three hetero atoms selected from the group consisting of from one to three nitrogen atoms and one oxygen or sulfur atom, or a 6-membered heteroaromatic group having from one to four nitrogen atoms, all of which may not be simultaneously adjacent to one another, where the phenyl and hetaryl groups may furthermore carry from one to three radicals selected from the group consisting of nitro, $C_1$–$C_4$-alkoxy, $C_1$–$C_4$-alkylthio, partially or completely halogenated $C_1$–$C_4$-alkoxy, radicals Z or a radical —$NR^kR^l$, in which $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which may furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio, or B) the group consisting of the 2-(4-hetaryloxy)- or 2-(4-aryloxy)-phenoxycarboxylic acid derivatives of the formula III

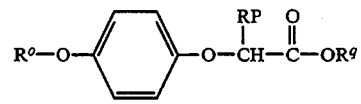

where $R^o$ is phenyl, pyridyl, benzoxazyl, benzothiazyl or benzopyrazinyl, where these aromatic ring systems may carry up to two of the following radicals: halogen, nitro, $C_1$–$C_4$-alkyl, partially or completely halogenated $C_1$–$C_4$-alkyl and/or partially or completely halogenated $C_1$–$C_4$-alkoxy;

$R^p$ is hydrogen or methyl, and $R^q$ is hydrogen, $C_1$–$C_4$-alkyl, $C_3$- or $C_4$-alkenyl, $C_3$- or $C_4$-alkynyl, $C_1$–$C_4$-alkoxy-$C_1$–$C_4$-alkyl, $C_3$- or $C_4$-alkylideneiminoxy-$C_2$- or —$C_3$-alkyl, tetrahydrofuranylmethyl, isoxazolidinyl or one equivalent of an agriculturally suitable cation.

The present invention furthermore relates to methods for selectively controlling herbicidal plant growth in crops with these herbicides.

The literature discloses thiochromenones of the formula I in which at least one of the radicals $R^1$, $R^2$ or $R^3$ is substituted amino, having a pharmaceutical action (EP-A 159,964, GB-A 2,014,991). Furthermore, the preparation of the thiochromenones of the formula I is described in a publication by Bosserr et al. (Ann. Chem. 680 (1964), 40 et seq.).

However, the stated publications do not describe any antidote or antagonistic action of the known compounds in combination with herbicidal active ingredients.

It is an object of the present invention to provide herbicides which ensure good control of undesirable plants without significantly damaging the crops or substantially reducing their yield at harvest.

We have found that this object is achieved by the herbicides defined at the outset.

We have also found methods for treating crops with the antagonistic compounds I and the herbicides II or herbicides III, whether the compounds I and II or I and III are formulated and applied together or separately, and the order of application in the case of separate application, being unimportant.

The herbicides contain at least one antagonistic compound I and at least one herbicide II or one herbicide III.

However, further antagonistic or herbicidal compounds may be present in the novel herbicides.

The substituents $R^1$ to $R^3$ of the substituted thiochromenones have the following specific meanings:

n is 1, 2, 3 or 4, and the radicals $R^3$ may have different meanings when n is >1;

$R^1$ is hydrogen; cyano;

halogen, such as fluorine, chlorine, bromine or iodine, preferably chlorine or bromine; alkyl, such as straight-chain or branched $C_1$–$C_{16}$-alkyl, in particular straight-chain or branched $C_5$–$C_{16}$-alkyl;

$C_1$–$C_4$-alkyl, such as methyl, ethyl, propyl, 1-methylethyl, butyl, 1-methylpropyl, 2-methylpropyl or 1,1-dimethylethyl, preferably methyl, ethyl or 2-methylpropyl, where this group may carry from one to five halogen atoms, such as fluorine, chlorine, bromine or iodine, preferably fluorine or chlorine, or one of the following radicals: hydroxyl, mercapto, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy and 2-methylpropoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably ethylthio and butylthio, aryl or hetaryl, in particular phenyl, naphthyl, thienyl or pyridyl, where the aromatic radicals in turn may carry from one to five halogen atoms, such as fluorine, chlorine, bromine or iodine, and/or from one to three of the following substituents:

$C_1$–$C_4$-alkyl, such as methyl, ethyl, propyl, 1-methylethyl, butyl, 1-methylpropyl, 2-methylpropyl and 1,1-dimethylethyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or 2-methylpropoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxY, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably ethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, aryl or hetaryl, in particular phenyl, naphthyl, thienyl or pyridyl, where these aromatic radicals in turn may carry from one to five halogen atoms, such as fluorine, chlorine, bromine or iodine, preferably fluorine or chlorine, and/or from one to three of the following substituents:

$C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or 2-methylpropoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, —$XR^4$ or —$COYR^4$, in which X is oxygen, sulfur or $NR^5$, Y is oxygen or $NR^5$, $R^4$ is one of the following groups: hydrogen; formyl; $C_1$–$C_{16}$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, butyl or 2,2-dimethylbutyl, $C_3$–$C_7$-cycloalkyl, such as cyclopropyl, cyclobutyl, cyclopentyl, cyclohexyl or cycloheptyl, preferably cyclopropyl or cyclohexyl, $C_1$–$C_{16}$-alkylcarbonyl, in particular $C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably methylcarbonyl, ethylcarbonyl or butyl carbonyl, $C_3$–$C_7$- cycloalkylcarbonyl, such as cyclopropylcarbonyl, cyclobutylcarbonyl, cyclopentylcarbonyl, cyclohexylcarbonyl or cycloheptylcarbonyl, preferably cyclopropylcarbonyl or cyclohexylcarbonyl, $C_1$–$C_{16}$-alkylsulfonyl, in particular $C_1$–$C_6$-alkylsulfonyl, such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl- 2-methylpropylsulfonyl, preferably methylsulfonyl or ethylsulfonyl, $C_3$–$C_7$-cycloalkylsulfonyl, such as cyclopropylsulfonyl, cyclobutylsulfonyl, cyclopentylsulfonyl, cyclohexylsulfonyl or cycloheptylsulfonyl, aryl, hetaryl, arylcarbonyl, hetarylcarbonyl, arylsulfonyl or hetarylsulfonyl, in particular phenyl, naphthyl, thienyl, pyridyl, phenylcarbonyl, naphthylcarbonyl, thienylcarbonyl, pyridylc arbonyl, phenylsulfonyl, naphthylsulfonyl, thienylsulfonyl or pyridylsulfonyl, where these aromatic radicals in turn may carry from one to five halogen atoms, such as fluorine, chlorine, bromine or iodine, preferably fluorine or chlorine, and/or from one to three of the following substituents:

$C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1 -methylpropoxy, 2 -methylpropoxy or 1,1 -dimethylethoxy, preferably methoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, and $R^5$ is hydrogen;

$C_1$–$C_{16}$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl or butyl, which may carry a hydroxyl or $C_1$–$C_4$-alkoxy group, such as methoxy, ethoxy, propoxy, 1-methylethoxy, butoxy, 1-methylpropoxy, 2-methylpropoxy or 1,1-dimethylethoxy, or is aryl or hetaryl, in particular phenyl, naphthyl, thienyl or pyridyl, where these aromatic radicals in turn may carry from one to five halogen atoms, such as fluorine, chlorine, bromine or iodine, preferably fluorine or chlorine, and/or from one to three of the following substituents:

$C_1$–$C_4$-alkyl, such as methyl, ethyl, propyl, 1-methylethyl, butyl, 1-methylpropyl, 2-methylpropyl or 1,1-dimethylethyl, preferably methyl, ethyl or 2-methylpropyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or 2-methylpropoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, and $R^2$ is hydrogen; cyano; nitroso, nitro;

halogen, such as fluorine, chlorine, bromine or iodine, preferably chlorine or bromine;

alkyl, such as straight-chain or branched $C_1$–$C_{16}$-alkyl, in particular straight-chain or branched $C_{51}$–$C_{16}$-alkyl; $C_1$–$C_4$-alkyl, such as methyl, ethyl, propyl, 1-methylethyl, butyl, 1-methylpropyl, 2-methylpropyl or 1,1-dimethylethyl, preferably methyl or ethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, or $C_1$–$C_4$-alkylthio, such as methylthio, ethylthio, propylthio, 1-methylethylthio, butylthio, 1-methylpropylthio, 2-methylpropylthio or 1,1-dimethylethylthio, where these groups may carry from one to five halogen atoms, such as fluorine, chlorine, bromine or iodine, preferably fluorine or chlorine, or one of the following radicals: hydroxyl, mercapto, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, aryl or hetaryl, in particular phenyl, naphthyl, thienyl or pyridyl, where the aromatic radicals in turn may carry from one to five halogen atoms, such as fluorine, chlorine, bromine or iodine, preferably fluorine or chlorine, and/or from one to three of the following substituents: $C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, aryl or hetaryl, in particular phenyl, naphthyl, thienyl or pyridyl, where these aromatic radicals in turn may carry from one to five halogen atoms, such as fluorine, chlorine, bromine or iodine, preferably fluorine or chlorine, and/or from one to three of the following substituents: $C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, —$NR^4R^5$ or —$COYR^4$, in which Y, $R^4$ and $R^5$ have in general and in particular the abovementioned meanings;

$R^3$ is hydrogen; cyano; halogen, such as fluorine, chlorine, bromine or iodine, preferably chlorine;

alkyl, such as straight-chain or branched $C_1$–$C_{16}$-alkyl, in particular straight-chain or branched $C_5$–$C_{16}$-alkyl;

$C_1$–$C_4$-alkyl, such as methyl, ethyl, propyl, 1-methylethyl, butyl, 1-methylpropyl, 2-methylpropyl or 1,1-dimethylethyl, preferably methyl, where this group may carry from one to five halogen atoms, such as fluorine, chlorine, bromine or iodine, preferably fluorine or chlorine, or one of the following radicals: hydroxyl, mercapto, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio or ethylthio, aryl or hetaryl, in particular phenyl, naphthyl, thienyl or pyridyl, where the aromatic radicals in turn may carry from one to five halogen atoms, such as fluorine, chlorine, bromine or iodine, preferably fluorine or chlorine, and/or from one to three of the following substituents: $C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2- fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or 2-methylpropoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, aryl or hetaryl, in particular phenyl, naphthyl, thienyl or pyridyl, where these aromatic radicals in turn may carry from one to five halogen atoms, such as fluorine, chlorine, bromine or iodine, and/or from one to three of the following substituents:

$C_1$–$C_4$-alkyl, such as methyl, ethyl, propyl, 1-methylethyl, butyl, 1-methylpropyl, 2-methylpropyl or 1,1-dimethylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy; $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

—$YR^4$, —$COYR^4$, —$COR^6$ or —$SO_2R^7$, in which Y and $R^4$ have in general and in particular the above-mentioned meanings;

$R^6$ is one of the following groups:
hydrogen;
$C_1$–$C_{16}$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl or butyl, $C_3$–$C_7$-cycloalkyl, such as cyclopropyl, cyclobutyl, cyclopentyl, cyclohexyl or cycloheptyl, preferably cyclopropyl or cyclohexyl, phenyl, naphthyl, thienyl or pyridyl, where these aromatic radicals in turn may carry from one to five halogen atoms, such as fluorine, chlorine, bromine or iodine, preferably fluorine or chlorine, and/or from one to three of the following substituents: $C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio, ethylthio or butylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio,
and
$R^7$ is hydrogen;
$C_1$–$C_{16}$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl or ethyl, $C_3$–$C_7$-cycloalkyl, such as cyclopropyl, cyclobutyl, cyclopentyl, cyclohexyl or cycloheptyl, phenyl, naphthyl, thienyl or pyridyl, where these aromatic radicals in turn may carry from one to five halogen atoms, such as fluorine, chlorine, bromine or iodine, preferably fluorine or chlorine, and/or from one to three of the following substituents: $C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, or —$NR^4R^5$, in which $R^4$ and $R^5$ have in general and in particular the abovementioned meanings, or one or more of the substituents are an acidic or basic group giving plant-tolerated salts with compounds I.

Particularly suitable antidotes for the novel use in herbicides are thiochromenones of the formula I which n is 1 or 2.

Other particularly suitable thiochromenones of the formula I are those in which $R^1$ has the following meanings:

hydrogen;

halogen as stated above in general and in particular;

$C_1$- or $C_2$-alkyl which may carry from one to five halogen atoms as stated above in general and in particular or one of the following radicals: $C_1$- or $C_2$-alkoxy, $C_1$- or $C_2$-alkylthio, phenyl, naphthyl, thienyl or pyridyl, where the aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio and $C_1$- or $C_2$-haloalkylthio as stated above in general and in particular;

phenyl, naphthyl, thienyl or pyridyl, where these aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular;

—$XR^4$ or —$COYR^4$, in which

X and Y are each oxygen or $NR^5$, $R^4$ is one of the following groups:

hydrogen; $C_1$–$C_6$-alkyl as stated above in general and in particular; $C_3$–$C_7$-cycloalkyl as stated above in general and in particular;

phenyl, naphthyl, thienyl or pyridyl, where these aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular, and $R^5$ is hydrogen or $C_1$–$C_6$-alkyl as stated above in general and in particular, which may carry hydroxyl or $C_1$–$C_4$-alkoxy as stated above in general and in particular.

Other preferred thiochromenones of the formula I are those in which $R^2$ has the following meanings:

hydrogen;

halogen as stated above in general and in particular;

$C_1$- or $C_2$-alkyl, $C_1$- or $C_2$-alkoxy or $C_1$- or $C_2$-alkylthio, where these groups may carry from one to five halogen atoms as stated above in general and in particular or one of the following radicals: $C_1$- or $C_2$-alkoxy, $C_1$- or $C_2$-alkylthio, phenyl, naphthyl, thienyl or pyridyl, where the aromatic radicals in turn may carry from one to five halogen atoms and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular;

phenyl, naphthyl, thienyl or pyridyl, where these aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular;

—$NR^4R^5$ or —$COYR^4$, in which

Y is oxygen or $NR^5$, $R^4$ is one of the following groups:

hydrogen;

$C_1$–$C_6$-alkyl as stated above in general and in particular;

$C_3$–$C_7$-cycloalkyl as stated above in general and in particular;

phenyl, naphthyl, thienyl or pyridyl, where these aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular, and $R^5$ is hydrogen or $C_1$–$C_6$-alkyl as stated above in general and in particular, which may carry hydroxyl or $C_1$–$C_4$-alkoxy as stated above in general and in particular.

Moreover, with regard to their use as antidotes, preferred thiochromenone derivatives of the formula I are also those in which $R^3$ has the following meanings:
hydrogen; halogen as stated above in general and in particular;

$C_1$–$C_4$-alkyl as stated above in general and in particular, where this group may carry from one to five halogen atoms as stated above in general and in particular or one of the following radicals: $C_1$- or $C_2$-alkoxy, $C_1$- or $C_2$-alkylthio, phenyl, naphthyl, thienyl or pyridyl, where the aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular;

—$YR^4$, —$COYR^4$, —$COR^6$ or —$SO_2R^7$, in which

Y is oxygen or $NR^5$, $R^4$ is one of the following groups:
hydrogen;
$C_1$–$C_6$-alkyl as stated above in general and in particular;
$C_3$–$C_7$-cycloalkyl as stated above in general and in particular;
phenyl, naphthyl, thienyl or pyridyl, where these aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular;

$R^5$ is hydrogen or
$C_1$–$C_6$-alkyl as stated above in general and in particular, which may carry hydroxyl or $C_1$–$C_4$-alkoxy as stated above in general and in particular;

$R^6$ is one of the following groups:
hydrogen;
$C_1$–$C_6$-alkyl as stated above in general and in particular;
$C_3$–$C_7$-cycloalkyl as stated above in general and in particular;
phenyl, naphthyl, thienyl or pyridyl, where these aromatic radicals in turn may carry from one to five halogen atoms as stated above in general and in particular and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular;

and $R^7$ is hydrogen;
$C_1$–$C_6$-alkyl as stated above in general and in particular;
$C_3$–$C_7$-cycloalkyl as stated above in general and in particular;
phenyl, naphthyl, thienyl or pyridyl, where these aromatic radicals in turn may carry from one to five halogen atoms as stated above in general and in particular, and/or from one to three of the following substituents: $C_1$- or $C_2$-alkyl, $C_1$- or $C_2$-haloalkyl as stated above in general and in particular, $C_1$- or $C_2$-alkoxy, $C_1$- or $C_2$-haloalkoxy as stated above in general and in particular, $C_1$- or $C_2$-alkylthio or $C_1$- or $C_2$-haloalkylthio as stated above in general and in particular; or —$NR^4R^5$ in which $R^4$ and $R^5$ have the abovementioned meanings.

Particularly preferred thiochromenones of the formula I for use in herbicides are those in which n is 1 or 2 and the substituents have the following meanings:
$R^1$ is hydrogen;
halogen as stated above in general and in particular;
$C_1$- or $C_2$-alkyl which may carry from one to five halogen atoms as stated above in general and in particular or $C_1$- or $C_2$-alkoxy;
phenyl which may carry from one to five halogen atoms as stated above in general and in particular and/or from one to three of the following substituents: $C_1$- or $C_2$-alkyl, $C_1$- or $C_2$-alkoxy or $C_1$- or $C_2$-alkylthio;
—$XR^4$ or —$COYR^4$, in which
X and Y are each oxygen or $NR^5$,
$R^4$ is one of the following groups:
hydrogen;
$C_1$–$C_6$-alkyl as stated above in general and in particular;
$C_3$–$C_7$-cycloalkyl as stated above in general and in particular;
phenyl which may carry from one to five halogen atoms as stated above in general and in particular and/or from one to three of the following substituents: $C_1$- or $C_2$-alkyl, $C_1$- or $C_2$-alkoxy or $C_1$- or $C_2$-alkylthio;
and
$R^5$ is hydrogen or $C_1$–$C_6$-alkyl as stated above in general and in particular;
$R^2$ is hydrogen;
halogen as stated above in general and in particular;
$C_1$- or $C_2$-alkyl or $C_1$- or $C_2$-alkoxy, where these groups may carry from one to five halogen atoms or a $C_1$- or $C_2$-alkoxy radical;
phenyl which may carry from one to five halogen atoms as stated above in general and in particular and/or from one to three of the following substituents: $C_1$- or $C_2$-alkyl, $C_1$- or $C_2$-alkoxy or $C_1$- or $C_2$-alkylthio;
—$NR^4R^5$ or —$COYR^4$, in which
Y, $R^4$ and $R^5$ have the abovementioned meanings;
$R^3$ is hydrogen;
halogen as stated above in general and in particular;
$C_1$–$C_4$-alkyl as stated above in general and in particular, where this group may carry from one to five halogen atoms as stated above in general and in particular or a $C_1$- or $C_2$-alkoxy radical;
—$YR^4$, —$COYR^4$, —$COR^6$ or —$SO_2R^7$, in which
Y and $R^4$ have the abovementioned meanings and $R^6$ and $R^7$ independently of one another are each $C_1$-$C_6$-alkyl as stated above in general and in particular or $C_3$-$C_7$-cycloalkyl as stated above in general and in particular;

phenyl which may carry from one to five halogen atoms as stated above in general and in particular and/or from one to three of the following substituents: $C_1$- or $C_2$-alkyl, $C_1$- or $C_2$-alkoxy or $C_1$- or $C_2$-alkylthio.

The substituted thiochromenones of the formula I are suitable as antidotes for improving the toleration of herbicidal active ingredients by crops such as millet, rice, corn, cereal species (wheat, rye, barley and oats), cotton, sugar beet, sugar cane and soybean. They have an antagonistic effect on herbicides from a very wide range of classes, such as triazines, phenylurea derivatives, carbamates, thiocarbamates, haloacetanilides, benzoic acid derivatives and in particular halophenoxyacetates, substituted phenoxyphenoxyacetates, phenoxyphenoxypropionates and cyclohexenone derivatives.

Herbicidal cyclohexenone derivatives II are disclosed in, for example, EP-A 228 598, EP-A 230 235, EP-A 238 021, EP-A 368 227, U.S. Pat. No. 4,432,786, DE-A 24 39 104 and DE-A 38 38 309. They are used predominantly for controlling undesirable grasses in dicotyledon crops and in grasses which do not belong to the Gramineae family. Depending on the substituents and the dosage of the compounds of type II and their use, these cyclohexenones can also be employed for selectively controlling undesirable grasses in gramineous crops, such as wheat and rice.

Further cyclohexenone derivatives II can be prepared in a conventional manner by synthesis methods known from the literature (cf. for example EP-A 169 521), for example by reacting triketones IX (disclosed in, for example, EP-A 80 301, EP-A 125 094, EP-A 142 741, U.S. Pat. No. 4, 249,937, EP-A 137 174 and EP-A 177 913) with hydroxylamines X (disclosed in, for example, Houben-Weyl, Methoden der Organischen Chemie, Volume 10/1, page 1181 et seq.):

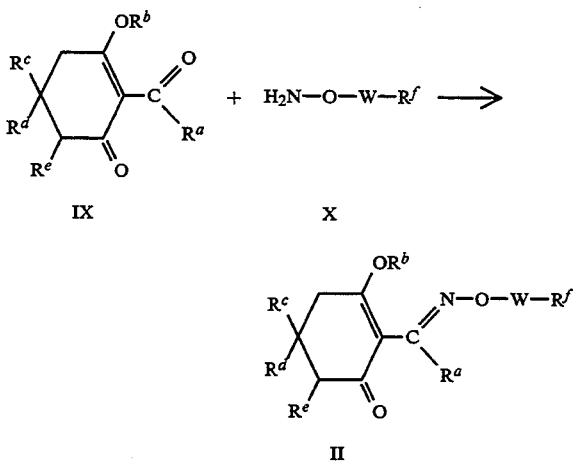

Advantageously, the reaction is carried out in the heterogeneous phase in a solvent, preferably in the presence of a base, the hydroxylamine preferably being used in the form of the ammonium salt.

Examples of suitable bases are the carbonates, bicarbonates, acetates, alcoholates and oxides of alkali metals and alkaline earth metals, such as sodium hydroxide, potassium hydroxide, magnesium oxide and calcium oxide, as well as organic bases, such as pyridine, and tertiary amines, e.g. triethylamine.

The triketone and hydroxylamine are preferably used in about stoichiometric amounts. The amount of base is not critical but is usually from about 0.5 to 2 mol equivalents, based on the amount of IX.

In general, the reaction temperature is from 0° C. to 80° C.

Examples of suitable solvents are dimethyl sulfoxide, alcohols, such as methanol, ethanol and isopropanol, aromatic hydrocarbons, such as benzene and toluene, chlorohydrocarbons, such as hexane and cyclohexane, esters, such as ethyl acetate, and ethers, such as diethyl ether, dioxane and tetrahydrofuran. The reaction is preferably carried out in methanol, using sodium bicarbonate as the base.

The reaction is complete after a few hours. The product II can be isolated, for example, by evaporating down the mixture, partitioning the residue in methylene chloride/water and distilling off the solvent under reduced pressure.

However, the free hydroxylamine base can also be used directly for this reaction, for example in the form of an aqueous solution; depending on the solvent used for the hydroxylamine X, a one-phase or two-phase reaction mixture is obtained.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

No special conditions are required with regard to the pressure; the reaction is therefore usually carried out at atmospheric pressure.

Alkali metal salts of the compounds II can be obtained by treating the 3-hydroxycompounds with sodium hydroxide, potassium hydroxide or a sodium or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts by means of ammonia or phosphonium, sulfonium or sulfoxonium hydroxides.

The compound of type IX can be prepared by known methods (Tetrahedron Lett. (1975), 2491), for example from the corresponding cyclohexane-1,3-diones of the formula XI

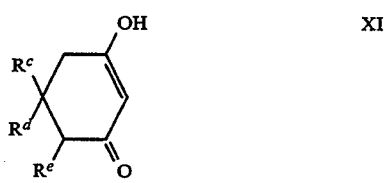

It is also possible to prepare the compounds of the formula IX via the enol ester intermediates, which are obtained in the reaction of compounds of the formula XI with acyl chlorides in the presence of bases and are then subjected to a rearrangement reaction with certain imidazole or pyridine derivatives (Japanese Preliminary Published Application 79/063 052).

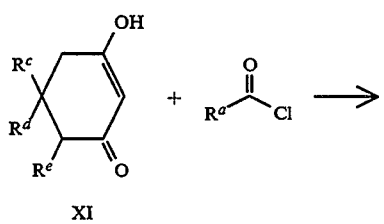

XI

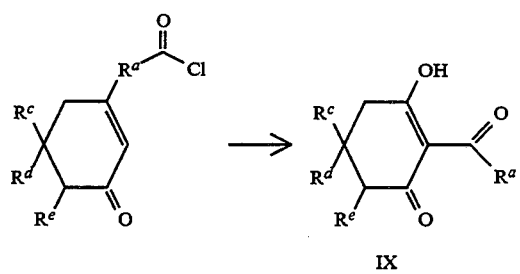

IX

The hydroxylamines of the formula X are obtained, as a rule, by a number of known process steps starting from known intermediates:

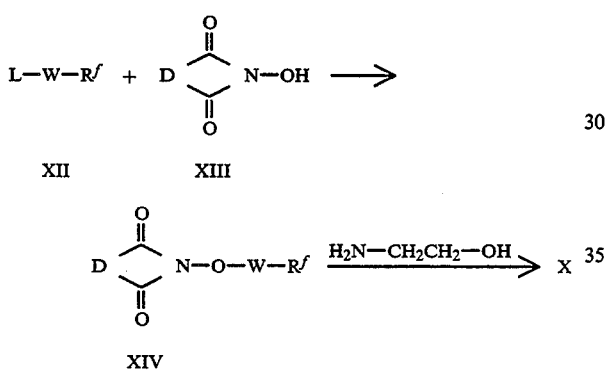

L=Hydroxyl or a leaving group, for example halogen, such as chlorine, bromine or iodine, or $CH_3SO_2$—O—.

The alkylating agents required for synthesizing the hydroxylamines X are known from the literature or can be prepared by known methods.

Syntheses of derivatives in which W is an aliphatic or olefinic chain which may be interrupted by hetero atoms are described in the following publications: DE-A 3 437 919; Tetrahedron Lett. 28 (1979), 2639; Org. Synth. Coll. 1 (1944), 436; DE-A 2 654 646; DE-A 2 714 561; J. Org. Chem. 52 (1987), 3587; DE-A 948 871; DE-A 948 872; J. Med. Chem. 26 (1983), 1570; Synthesis (1983), 675; J. Org. Chem. 48 (1983), 4970; Org. Synth. Coll. Vol. V, 249; EP 48 911; EP 143 952; U.S. Pat. No. 4,686,735.

For the preparation of compounds II in which W is an aliphatic or olefinic chain and $R^f$ is a heterocyclic structure, reference may be made to the following literature: J. Heterocycl. Chem. 14 (1976), 525; JP 55 051 004; JP 55 047 601; Houben-Weyl: Methoden der organischen Chemie Volume 4/3, page 424 et seq.; DE-A-2 821 409; Chem. Ber. 114 (1981), 3667 and 3674.

Preparation methods which start from suitable carbinols XII (L=OH) are disclosed, for example, in: Tetrahedron 35 (1979), 329; Chem. Lett. (1977), 423; Houben-Weyl, Methoden der organischen Chemie, Volume 13/9B, page.964 et seq., ibid. Volume 5/3, pages 862 and 899 et seq.; ibid. Volume 5/4, page 361 et seq.

The preparation of alkylating agents in which W is substituted or unsubstituted $C_3$-$C_6$-alkynyl can be carried out by classical methods (cf. J. Med. Chem. 29 (1986), 1389; ibid. 24 (1981), 678; EP-A 131 320; J. Chem. Ecol. 10 (1982), 1201) or by coupling 1-alkynyl derivatives to aryl or hetaryl halides in the presence of palladium catalysts (cf. for example Tetrahedron Lett. 50 (1975), 4467).

XII is coupled to a cyclic hydroxylimide XIII and the resulting protected hydroxylamine derivative XIV is cleaved to give the free hydroxylamine X, preferably with 2-aminoethanol.

When HO-W-$R^f$ is used, it is advisable to proceed according to the Mitsunobu variant (cf. Synthesis (1981), 1 and J. Med. Chem. 33 (1990) 187).

In the cyclic hydroxylimides X, D is, for example, $C_2$-$C_3$-alkylene, $C_2$-alkenylene or a 5-membered or 6-membered ring containing up to three double bonds and, if required, a nitrogen atom, for example phenylene, pyridinylene, cyclopentylene, cyclohexylene or cyclohexenylene. For example, the following substances are suitable:

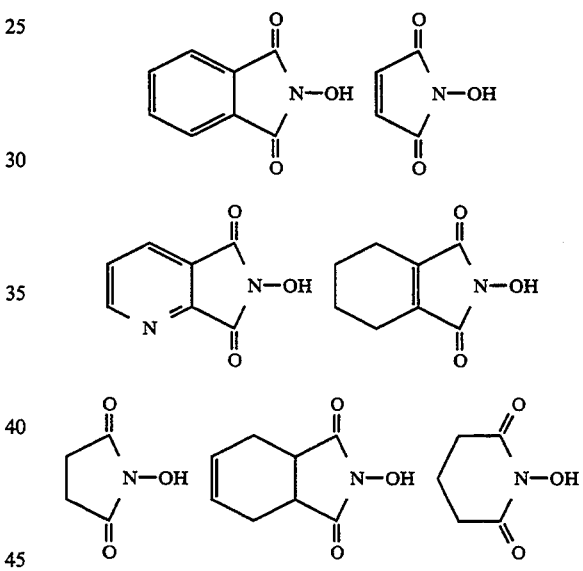

The reaction of the compounds IX with the hydroxylimides XIII is advantageously carried out in the presence of a base. Suitable bases are in principle all those which are capable of deprotonating the hydroxylimides XIII without attacking the imide system. These are in particular the nonnucleophilic bases. Examples are mineral bases, such as alkali metal and alkaline earth metal carbonates, and alkali metal and alkaline earth metal bicarbonates, and organic bases, such as aliphatic, cycloaliphatic and aromatic tertiary amines. Mixtures of these bases may also be used.

Examples of individual compounds are the following bases: sodium carbonate, potassium carbonate, magnesium carbonate, calcium carbonate, barium carbonate, the bicarbonates of these metals, trimethylamine, triethylamine, tributylamine, ethyldiisopropylamine, N,N-dimethylaniline, 4-N,N-dimethylaminopyridine, diazabicyclooctane, diazabicycloundecane, N-methylpiperidine, 1,4-dimethylpiperazine, pyridine, quinoline, bipyridine and phenanthroline. The economical bases sodium carbonate and potassium carbonate are preferred.

The base is added in general in equivalent amounts up to an excess of 5 equivalents, based on the hydroxylimide. A larger excess is possible but has no additional advantages. It is also possible to use a small amount of bases. However, from 1 to 3, in particular from 1 to 2, equivalents, based on the hydroxylimide XIII, of a base are preferably used.

It is also possible to use nucleophilic bases, for example alkali metal and alkaline earth metal hydroxides, in particular sodium hydroxide and potassium hydroxide. In this case, it is advantageous to use the base in equivalent amounts, based on the hydroxylimide XIII, in order to avoid nucleophilic attack by the hydroxyl ions on the carbonyl function of the imide group.

The starting compounds XII are advantageously reacted with the hydroxylimides XIII in a solvent which is inert under the reaction conditions. Advantageous solvents are, for example, polar aprotic solvents, such as dimethylformamide, N-methylpyrrolidone, dimethyl sulfoxide, sulfolane and cyclic ureas. The amount of solvent is in general not critical.

The reaction of the starting compounds XII with the hydroxylimides XIII can also be carried out using phase transfer catalysis. In this case, solvents which form two phases with water, preferably chlorohydrocarbons, are used. Suitable phase transfer catalysts are the quaternary ammonium and phosphonium salts, polyethylene glycol, polyethylene glycol ethers and crown ethers usually used for such purposes, as described in, for example, Dehmlow et al., Phase Transfer Catalysis, pages 37–45 and pages 86–93, Verlag Chemie, Weinheim 1980. The phase transfer catalysts are advantageously used in amounts of from 1 to 10, preferably from 3 to 5, % by volume, based on the volume of the reaction mixture.

The reaction of the starting compounds XII with the hydroxylimides XIII is carried out in general at from 0° to 140° C. preferably from 20° to 100° C., in particular from 40° to 80° C. In an advantageous procedure, the hydroxylimide XIII is initially taken together with the base in the solvent, and the starting material XII is metered into this solution. It may prove advantageous if the hydroxylimide is added at a lower temperature, for example at up to 50° C., and the reaction mixture is heated to the actual reaction temperature only after this addition.

As a rule, the reaction is carried out at atmospheric pressure or at the autogenous pressure of the solvent.

After the end of the reaction, water is advantageously added to the cooled reaction mixture, the resulting hydroxylamine derivatives XIV separating out as crystalline solids or as oils. The hydroxylamine derivatives obtained in this manner can, if desired, be further purified by recrystallization or by extraction.

The hydroxylamine derivatives XIV may be stored or immediately converted into the hydroxylamine derivatives X having a free amino group. This conversion can be carried out by conventional methods, as described in, for example, DE-A 36 15 973 and the publications cited therein. The process according to DE-A 36 15 973, in which the hydroxylamine derivatives X are liberated by means of ethanolamine, is preferably used. It is also possible to liberate the hydroxylamine derivatives X with the aid of other bases, such as aqueous mineral bases, amines, hydrazines, hydroxylamines or aqueous acids.

The hydroxylamine derivatives X can be isolated from the reaction mixtures obtained by these processes by means of conventional working up methods, for example by extraction or by crystallization. To increase the tendency of these hydroxylamine derivatives to crystallize, it may also be beneficial to convert them into their salts with mineral acids or organic acids. For this purpose, dilute solutions of these acids are generally reacted with the hydroxylamine derivatives, advantageously in equivalent amounts. As in the case of the hydroxylamine derivatives having a free amino group, the resulting hydroxylammonium salts can be further processed directly to give the herbicides of the formula II or, if desired, can be stored.

The cyclohexenone derivatives II may be obtained as isomer mixtures in the preparation, both E/Z isomer mixtures and enantiomer or diastereoisomer mixtures being possible. The isomer mixtures can, if desired, be separated by the conventional methods, for example by chromatography or by crystallization.

Suitable herbicidal active ingredients (A) are both the pure enantiomers II and racemates or diastereoisomer mixtures of cyclohexenone derivates II.

The cyclohexenone derivatives II may be represented in a plurality of tautomeric forms, all of which form the subject of the invention.

Preparation Examples (Cyclohexenone Derivatives)

EXAMPLE 1

2-[1-(3-(4-Bromophenyl)-prop-2-enyloximino)-propyl]-3-hydroxy-5-(3-tetrahydrothiopyranyl)-cyclohex-2-en-1-one

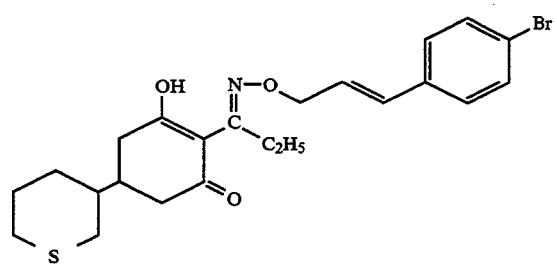

3.0 g (0.011 mol) of 2-propionyl-5-(3-tetrahydrothiopyranyl)-cyclohexane-1,3-dione and 3.0 g (0.013 mol) of 3-(4-bromophenyl)-prop-2-enyloxyamine in 100 ml of methanol were stirred at 20° C. for 16 hours. The precipitated reaction product was separated off at 0° C., washed with ice-cold methanol and petroleum ether and dried. Yield: 68.4%; mp.: 97°–99° C.

Intermediate 1.1

N-3-(4-Bromophenyl)-prop-2-enyloxyphthalimide 18.5 g (0.11 mol) of N-hydroxyphthalimide and 31.4 g (0.11 mol) of 1-bromo-3-(4-bromophenyl)-prop-2-ene were added in succession to 350 ml of dry N-methylpyrrolidone, and 12.1 g (0.12 mol) of triethylamine were then added dropwise at room temperature. The reaction mixture was stirred for four days at 20° C. and then poured onto 1.5 l of ice water, and the product was filtered off and washed with water and isopropanol. Yield: 86.8%; mp.: 161°–162° C.

Intermediate 1.2

3-(4-Bromophenyl)-prop-2-enyloxyamine 33.4 g (0.093 mol) of N-3-(4-bromophenyl)-prop-2-enyloxyphthalimide were introduced a little at a time into 50 ml of ethanolamine; the temperature increased to 30° C. during the procedure. Stirring was carried out for two hours at 60° C., after which the mixture was allowed to cool and 200 ml of dichloromethane were added to it. It was extracted by shaking with ice water. The organic phase was dried and evaporated down and the residue was crystallized from petroleum ether. Yield: 95.3%; mp.: 35°–38° C.

EXAMPLE 2

2-[1-(4-(4-Fluorophenyl)-but-3-ynyloximino)-butyl]-3-hydroxy-5-tetrahydropyran-4-ylcyclohex-2-enone

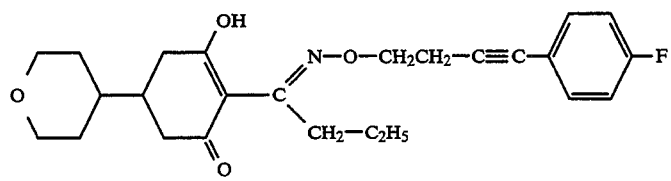

2.7 g (15 mmol) of 4-(4-fluorophenyl)-but-3ynoxyamine were added to a solution of 4 g (15 mmol) of 2-butyryl-3-hydroxy-5-tetrahydropyran-4-ylcyclohex-2-enone in 60 ml of dry methanol. Stirring was carried out for 16 hours at room temperature, after which the methanol was removed under reduced pressure from a water pump. The crude product was purified by means of chromatography over silica gel (mobile phase: methylene chloride). Yield: 81.2%.

Intermediate 2.1

4-(4-Fluorophenyl)-3-butynol 1 g of bis(triphenylphosphine)palladium(II chloride, 3.8 g of copper(I) iodide and 8.7 g of triphenylphosphine were added in succession to a solution of 100 g of 4-bromofluorobenzene in 350 ml of triethylamine. This mixture was heated to the reflux temperature, after which 43.4 g of 3-butynol were added dropwise in the course of 20 minutes at this temperature (about 100° C.). Stirring was carried out for a further 5 hours at this temperature. After cooling, the triethylamine was distilled off. The residue was taken up in methyl tertbutyl ether and water. The aqueous phase was extracted twice more with methyl tert-butyl ether, and the combined organic extracts were washed in succession with 1N hydrochloric acid and with 10% sodium bicarbonate solution and dried over sodium sulfate. After the solvent had been removed, the crude product was distilled at greatly reduced pressure. Yield: 86%.

Intermediate 2.2

N-(5-(4-Fluorophenyl)-4-pentynyloxy)-phthalimide 33.4 g (0.205 mol) of N-hydroxyphthalimide and 53.8 g (0.205 mol) of triphenylphosphine were added to a solution of 33.1 g (0.186 mol) of 5-hydroxy-1-(4-fluorophenyl)-1-pentyne in 430 ml of dry tetrahydrofuran. 35.7 g (0.205 mol) of diethyl azodicarboxylate were then added dropwise in the course of 2.5 hours with temperature control (max. 40° C.). Stirring was carried out overnight at room temperature, the mixture was evaporated down under reduced pressure and the residue was taken up with 300 ml of dichloromethane. The solution was washed twice with sodium carbonate solution and once with saturated sodium chloride solution. After drying and evaporating down, the crude product was purified by chromatography over silica gel. The eluents used were initially dichloromethane/n-hexane and subsequently pure dichloromethane. Yield: 82%; mp.: 85°–88° C. 250-MHz-$^1$H-NMR (in DMSO-d$_6$): δ[ppm]=1.9–2.1 (m, 2H); 2.68 (t, 2H); 4.342 (t, 2H); 7.18 (t, 2H); 7.4–7.6 (m, 2H); 7.85 (s, 4H).

Intermediate 2.3

5-Aminooxy-1-(4-fluorophenyl)-1-pentyne 47.7 g (0.148 mol) of the phthalimidoether prepared above were added a little at a time to a mixture of 68 ml of ethanolamine and 40 ml of dichloromethane. After stirring for 2 hours at room temperature, a clear solution had formed. This was poured into 300 ml of ice-cold, saturated sodium chloride solution. The mixture was extracted three times with 100 ml of dichloromethane, and the combined organic phases were washed once with sodium chloride solution, dried and evaporated down. Yield: 95% (oil). 250-MHz-$^1$H-NMR (in CDCl$_3$): δ[ppm]=1.8–2.0 (m, 2H); 2.47 (6, 2H); 3.8 (t, 2H); 5.4 (broad s, 2H); 6.9–7.1 (m, 2H); 7.3–7.45 (m, 2H).

EXAMPLE 3

2-[1-[[(E)-4-(2-Thienyl)-3-butenyloxy]-imino]-butyl]-3-hydroxy-5-(2H-tetrahydropyran-4-yl)-cyclohex-2-en-1-one

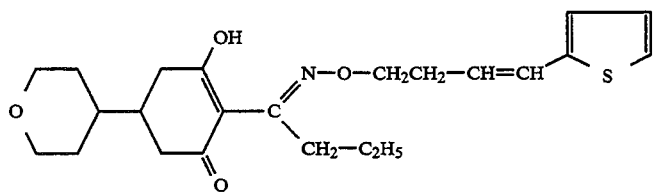

A mixture of 35 g (0.13 mol) of 2-butyryl-3-hydroxy-5-(2H-tetrahydropyran-4-yl)-2-cyclohexen-1-one and 24 g (0.14 mol) of O-[(E)-4-(2-thienyl)-3-butenyl]-hydroxylamine in 300 ml of methanol were stirred for 16 hours. The mixture was evaporated down under reduced pressure and the residue was taken up in 1000 ml of 10% strength sodium hydroxide solution. The solution was extracted with three times 200 ml of methylene chloride and the aqueous phase was brought to pH 1 with concentrated hydrochloric acid while cooling with ice. The aqueous phase was then extracted with three times 200 ml of ether, dried over magnesium sulfate and evaporated down under reduced pressure. The crude product was purified by chromatography by 100 g of silica gel in a 30×15 cm column (mobile phase: ethyl acetate). Yield: 85%. 200 MHz-$^1$H-NMR (in CDCl$_3$): δ[ppm]=0.95 (t, 3H), 1.17-1.96 (m, 9H), 2.13 (m, 1H), 2.36 (m, 1H), 2.43-2.70 (m, 3H), 2.88 (m, 2H), 3.36 (t, 2H), 4.02 (d, 2H), 4.15 (t, 2H), 6.00 (dt, 1H), 6.60 (d, 1H), 6.80-7.20 (m, 3H), 14.75 (s, 1H).

Intermediate 3.1

(E)-4-Bromo-1-(2-thienyl)-1-butene 225 g (1.46 mol) of cyclopropyl-2-thienylcarbinol were added dropwise to 972 ml of 48% strength hydrobromic acid at from 5° to 10° C. in the course of 1 hour.

After 2 hours at room temperature, the organic phase was separated off and the aqueous solution was extracted with three times 300 ml of dichloromethane. The combined organic phases were washed neutral with dilute sodium hydroxide solution and water, dried over magnesium sulfate and evaporated down under reduced pressure. 322 g (94% corrected) of crude bromide (GC: 92%) were obtained. 250 MHz-$^1$H-NMR (in CDCl$_3$): δ[ppm]=2.65-2.80 (m, 2H), 3.46 (t, 2H), 5.90-6.10 (m, 1H), 6.61 (d, 1H), 6.80-7.00 (m, 2H), 7.14 (d, 1H).

Intermediate 3.2

N-[(E)-4-(2-Thienyl)-3-butenyloxy]-phthalimide 190 ml (1.37 mol) of triethylamine were added dropwise, at from 20° to 25° C. in the course of 2.5 hours, to a mixture of 283 g (1.30 mol) of the bromide prepared above, 1300 ml of N-methyl-2-pyrrolidinone, 10 g of potassium iodide and 212 g (1.30 mol) of N-hydroxyphthalimide. After 4 hours at from 20° to 25° C., the mixture was poured into 4000 ml of ice water, and 5000 ml of 10% strength sodium hydroxide solution were added a little at a time. Extraction was then carried out with four times 500 ml of ethyl acetate. The combined ethyl acetate phases were washed neutral with dilute sodium hydroxide solution and water, dried over magnesium sulfate and evaporated down under reduced pressure. The crude product was purified by chromatography over 1000 g of silica gel in a 30×15 cm column (mobile phase: 7: 3 n-hexane/dichloromethane). Yield: 29%; mp.: 69°-71° C. (isopropanol). 250 MHz-$^1$H-NMR (in d$_6$-DMSO): δ[ppm]=2.55-2.70 (m, 2H), 4.28 (t, 2H), 6.00-6.20 (m, 1H), 6.77 (d, 1H), 7.00 (m, 2H), 7.35 (m, 1H), 7.87 (2, 4H).

Intermediate 3.3

O-[(E)-4-(2-Thienyl)-3-butenyl]-hydroxylamine

A mixture of 90.2 g (0.30 mol) of the phthalimidoether prepared above and 136 ml of ethanolamine was stirred for 3 hours at 60° C. The cold reaction mixture was poured into 200 ml of ice water. 200 ml of saturated sodium chloride solution were added and the hydrolysis product was extracted with three times 300 ml of dichloromethane. The combined organic phases were then washed with three times 100 ml of saturated sodium chloride solution, dried over magnesium sulfate and evaporated down under reduced pressure. Yield: 89%. 250 MHz-$^1$H-NMR (in CDCl$_3$): δ[ppm]=2.40-2.55 (m, 2H), 3.78 (t, 2H), 5.40 (bs, 2H), 5.95-6.20 (m, 1H), 6.57 (d, 1H), 6.80-7.15 (m, 3H).

EXAMPLE 4

2-[1-[[2-(2-Fluorobenzyloxy)-ethoxy]-imino]-butyl]-2-hydroxy-5-(2H-tetrahydropyran-4-yl)-2-cyclohexen-1-one

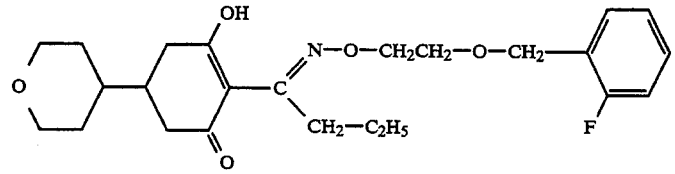

A mixture of 4.0 g (10 mmol) of 2-butyryl-3-hydroxy-5-(2H-tetrahydropyran-4-yl)-2-cyclohexen-1-one and 2.6 g (14 mmol) of O-[2-(2-fluorobenzyloxy)-ethyl]-hydroxylamine in 100 ml of methanol was stirred for 24 hours. The reaction mixture was evaporated down under reduced pressure and the crude product was chromatographed over 100 g of silica gel (30×4 cm column; mobile phase: ether). Yield: 54%. 300 MHz-$^1$H-NMR (in CDCl$_3$): δ[ppm]=0.93 (t, 3H), 1.20-1.77 (m, 7H), 1.90 (m, 1H), 2.23 (m, 2H), 2.58 (m, 2H), 2.92 (m, 2H), 3.38 (t, 2H), 3.80 (m, 2H), 4.03 (m, 2H), 4.25 (m, 2H), 4.68 (s, 2h), 6.93-7.50 (m, 4H), 14.30 (s, 1H).

Intermediate 4.1

N-[2-(2-Fluorobenzyloxy)-ethoxy]-phthalimide 108 ml of triethylamine were added dropwise to a mixture of 165 g (0.71 mol) of 1-bromo-2-(2-fluorobenzyloxy)-ethane, 116 g (0.7 mol) of N-hydroxylphthalimide and 710 ml of N-methyl-2-pyrrolidinone at from 20° to 25° C. in the course of 1 hour. After 5 hours at 60° C., the cold reaction mixture was poured into 200 ml of ice water and the precipitate was filtered off under suction, washed with water and isopropanol and dried under reduced pressure over phosphorus pentoxide.

Yield: 82%; mp.: 62°-64° C.

250 MHz-$^1$H-NMR (in d$_6$-DMS): δ[ppm]=3.85 (m, 2H), 4.35 (m, 1H), 4.54 (s, 2H), 7.10-7.40 (m, 4H), 7.88 (s, 4H).

Intermediate 4.2

O-[2-(2-Fluorobenzyloxy)-ethyl]-hydroxylamine 184 g (0.58 mol) of the phthalimidoether prepared above were introduced a little at a time in 270 ml of ethanolamine After 3 hours at 60° C. the cold reaction mixture was poured into 1000 ml of ice water. The hydrolysis product was extracted with three times 800 ml of dichloromethane. The combined organic phases were washed with 200 ml of saturated sodium chloride solution, dried over magnesium sulfate and evaporated down under reduced pressure. Yield: 91%. $^1$H-NMR (250 MHz, CDCl$_3$): δ[ppm]=3.70 (dd, 2H), 3.85 (dd, 2H), 4.54 (s, 2H), 5.50 (bs, 2H), 7.00–7.50 (m, 4H).

In view of the intended use of the novel herbicides, suitable cyclohexenone derivatives of the formula II are those in which the substituents have the following specific meanings:

$R^a$ is straight-chain or branched $C_1$-$C_6$-alkyl, such as methyl, ethyl, propyl, isopropyl, n-butyl, sec-butyl, isobutyl, tert-butyl, n-pentyl or n-hexyl, in particular ethyl or propyl;

$R^b$ is hydrogen;

one equivalent of an agriculturally suitable cation, for example an alkali metal cation, such as sodium or potassium, one equivalent of an alkaline earth metal cation, such as calcium, magnesium or barium, manganese, copper, zinc or iron cations, ammonium cations having, if desired, from one to three substituents selected from the group consisting of three $C_1$-$C_4$-alkyl radicals, three hydroxy-$C_1$-$C_4$-alkyl radicals and one phenyl or benzyl radical, such as tetraalkylammonium and benzyltrialkylammonium cations, phosphonium cations or sulfonium cations, such as trialkylsulfonium cations, or sulfoxonium cations;

$C_2$-$C_8$-alkylcarbonyloxy, such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentyl-carbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl- 1-methylpropyl-carbonyloxy or 1-ethyl-2-methylpropylcarbonyloxy;

a benzoyl group or a derivative substituted in the phenyl nucleus by from one to five halogen atoms;

straight-chain or branched $C_1$-$C_{10}$-alkylsulfonyl, in particular $C_1$-$C_6$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, benzenesulfonyl or a derivative substituted in the phenyl nucleus by from one to five halogen atoms;

straight-chain or branched $C_1$-$C_{10}$-alkylphosphonyl, in particular $C_1$-$C_6$-alkylphosphonyl, such as methylphosphonyl, ethylphosphonyl, n-propylphosphonyl, 1-methylethylphosphonyl, n-butylphosphonyl, 1-methylpropylphosphonyl, 2-methylpropylphosphonyl, 1,1-dimethylethylphosphonyl, n-pentylphosphonyl, 1-methylbutylphosphonyl, 2-methylbutylphosphonyl, 3-methylbutylphosphonyl, 1,1-dimethylpropylphosphonyl, 1,2-dimethylpropylphosphonyl, 2,2-dimethylpropylphosphonyl, 1-ethylpropylphosphonyl, hexylphosphonyl, 1-methylpentylphosphonyl, 2-methylpentylphosphonyl, 3-methylpentylphosphonyl, 4-methylpentylphosphonyl, 1,1-dimethylbutylphosphonyl, 1,2-dimethylbutylphosphonyl, 1,3-dimethylbutylphosphonyl, 2,2-dimethylbutylphosphonyl, 2,3-dimethylbutylphosphonyl, 3,3-dimethylbutylphosphonyl, 1-ethylbutylphosphonyl, 2-ethylbutylphosphonyl, 1,1,2-trimethylpropylphosphonyl, 1,2,2-trimethylpropylphosphonyl, 1-ethyl-1-methylpropylphosphonyl or 1-ethyl-2-methylpropylphosphonyl, benzenephosphyl or a derivative substituted in the phenyl nucleus by from one to five halogen atoms;

$R^c$ is hydrogen; cyano; formyl;

straight-chain or branched $C_1$-$C_6$-alkyl as stated above, in particular ethyl, n-propyl or isopropyl;

$C_1$-$C_4$-alkoxy-$C_1$-$C_4$-alkyl, such as methoxymethyl, ethoxymethyl, propoxymethyl, 1-methoxyethyl, 2-methoxyethyl, 1-ethoxyethyl, 2-ethoxyethyl, 2-propoxyethyl, 1-methoxypropyl, 2-methoxypropyl, 3-methoxypropyl, 1-ethoxypropyl, 2-ethoxypropyl, 3-ethoxypropyl, 1-methoxybutyl, 2-methoxybutyl, 3-methoxybutyl, 4-methoxybutyl, 1-ethoxybutyl, 2-ethoxybutyl, 3-ethoxybutyl, 4-ethoxybutyl, 1,3-dimethoxypropyl, preferably methoxymethyl or 2-ethoxyethyl;

$C_1$-$C_4$-alkylthio-$C_1$-$C_4$-alkyl, such as methylthiomethyl, ethylthiomethyl, 1-methylthioethyl, 2-methylthioethyl, 1-ethylthioethyl, 2-ethylthioethyl, 1-methylthiopropyl, 2-methylthiopropyl, 3-methylthiopropyl, 1-ethylthiopropyl, 2-ethylthiopropyl, 3-ethylthiopropyl, 1-methylthiobutyl, 2-methylthiobutyl, 3-methylthiobutyl, 4-methylthiobutyl, 1-ethylthiobutyl, 2-ethylthiobutyl, 3-ethylthiobutyl, 4-ethylthiobutyl, preferably 2-ethylthiopropyl;

phenoxy-$C_1$-$C_6$-alkyl, phenylthio-$C_1$-$C_6$-alkyl, pyridyloxy-$C_1$-$C_6$-alkyl or pyridylthio-$C_1$-$C_6$-alkyl, where the phenyl and pyridyl groups may furthermore carry from one to three radicals selected from the group consisting of nitro, cyano, halogen, such as fluorine, chlorine, bromine and iodine, in particular fluorine and chlorine, straight-chain and branched $C_1$-$C_4$-alkyl, such as methyl, ethyl, n-propyl, isopropyl, n-butyl and tert-butyl, partly or completely halogenated $C_1$-$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-2-chloro-2-fluoroethyl, 2-chloro-2,2-trifluoroethyl, 2,2-dichloro-2-fluoroethyl, 2,2,2-difluoroethyl, trichloroethyl and pentafluoroethyl, preferably trifluoromethyl, $C_1$-$C_4$-alkoxy, such as methoxy, ethoxy, n-propoxy, isopropoxy, n-butoxy and tert-butoxy, preferably methoxy and ethoxy, partially or completely halogenated $C_1$-$C_4$-alkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, in particular trifluoromethoxy, $C_1$–$C_4$-alkylthio, such as methylthio, ethylthio, n-propylthio, isopropylthio, n-butylthio and tert-butylthio, preferably methylthio and ethylthio, $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably prop-2-enyl or but-3-enyl, $C_3$–$C_6$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, butenyloxy, 3,3-dimethyl-2-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy, preferably prop-2-enyloxy or but-2-enyloxy, $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-3-pentynyl, 1-methyl-4-pentynyl, 2-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl preferably prop-2-ynyl, $C_3$–$C_6$-alkynyloxy such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably prop-2-ynyloxy, or —$NR^gR^h$, in which $R^h$ is hydrogen, straight-chain or branched $C_1$–$C_4$-alkyl as stated above, $C_3$–$C_6$-alkenyl as stated above or $C_3$–$C_6$-alkynyl as stated above, preferably hydrogen, and $R^g$ is hydrogen, straight-chain or branched $C_1$–$C_4$-alkyl as stated above, $C_3$–$C_6$-alkenyl as stated above, $C_3$–$C_6$-alkynyl as stated above, $C_1$–$C_6$-acyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular methylcarbonyl or 1,1-dimethylethylcarbonyl;

or benzoyl which may furthermore carry from one to three substituents selected from the group consisting of nitro, cyano, halogen as stated above, in particular fluorine and chlorine, straight-chain or branched $C_1$–$C_4$-alkyl as stated above, partially or completely halogenated $C_1$–$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably trifluoromethyl;

$C_1$–$C_4$-alkoxy as stated above and $C_1$–$C_4$-alkylthio as stated above;

particularly preferred phenoxy-$C_1$–$C_6$-alkyl, phenylthio-$C_1$–$C_6$-alkyl, pyridyloxy-$C_1$–$C_6$-alkyl or pyridylthio-$C_1$–$C_6$-alkyl groups are phenoxymethyl, phenoxyethyl, phenoxypropyl, phenoxybutyl, 4-fluorophenoxyethyl, 2-(4-fluoro-phenoxy)-propyl, 4-trifluoromethyphenoxyethyl, 2-(4-trifluoromethyl-phenoxy)-propyl, phenylthiomethyl, phenylthioethyl, phenylthiopropyl, phenylthiobutyl, 4-fluorophenylthioethyl, 2-(4-fluorophenylthio)-propyl, 4-trifluoromethylphenylthioethyl or 2-(4-trifluoromethylphenylthio)-propyl, in particular 4-fluorophenylthioethyl or 4-trifluoromethylphenylthioethyl;

$C_3$-$C_7$-cycloalkyl or $C_5$-$C_7$-cycloalkenyl, such as cyclopropyl, cyclobutyl, cyclopentyl, cyclohexyl, cycloheptyl cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl or cyclohept-4-enyl, where each of the carbocyclic radicals may furthermore carry from one to three radicals selected from the group consisting of hydroxyl, halogen as stated above, in particular fluorine and chlorine, straight-chain or branched $C_1$-$C_4$-alkyl as stated above, in particular methyl or ethyl, partially or completely halogenated $C_1$-$C_4$-alkyl as stated above, in particular trifluoromethyl, $C_1$-$C_4$-alkoxy as stated above, in particular methoxy, $C_1$-$C_4$-alkylthio as stated above, in particular methylthio and ethylthio, benzylthio, $C_1$-$C_4$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl, preferably methylsulfonyl, and $C_1$-$C_4$-alkylsulfinyl, such as methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl, preferably methylsulfinyl; among the substituted $C_3$-$C_7$-cycloalkyl and $C_5$-$C_7$-cycloalkenyl groups, 1-methylthiocyclopropyl, 1-ethylthiocyclopropyl, 4-methylcyclohexyl, 4-methylcyclohex-3-enyl, 3-ethylthio-4-hydroxy-4-methylcyclohexyl and 3,4-dihydroxycyclohexyl are preferred, in particular 1-methylthiocyclopropyl, 1-ethylthiocyclopropyl and 3,4-dihydroxycyclohexyl;

5-membered heterocycloalkyl, such as tetrahydrofuran-2-yl, tetrahydrofuran-3-yl, tetrahydrothien-2-yl, tetrahydrothien-3-yl, pyrrolidin-2-yl, pyrrolidin-3-yl, isoxazolidin-3-yl, isoxazolidin-4-yl, isoxazolidin-5-yl, isothiazolidin-3-yl, isthaizolidin-4-yl, isthaizolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl or 1,3,4-thiadiazolidin-2-yl, dioxolanyl, dithiolanyl, in particular tetrahydrofuran-2-yl, tetrahydrofuran-3-yl or dioxolanyl, where the heterocyclic radicals may each furthermore carry from one to three radicals selected from the group consisting of straight-chain or branched $C_1$-$C_4$-alkyl as stated above, in particular methyl and ethyl, partially and completely halogenated $C_1$-$C_4$-alkyl as stated above, in particular trifluoromethyl, $C_1$-$C_4$-alkoxy as stated above, in particular methoxy, and $C_1$-$C_4$-alkylthio as stated above, in particular methylthio;

a 6-membered or 7-membered heterocyclic structure, such as tetrahydrothiopyran-2-yl, tetrahydrothiopyran-3-yl, tetrahydrothiopyran-4-yl, tetrahydropyran-2-yl, tetrahydropyran-3-yl, tetrahydropyran-4-yl, 5,6-dihydro-H-thiopyran-2-yl, 5,6-dihydro-2H-thiopyran-3-yl, 5,6-dihydro-2H-thiopyran-4-yl, 5,6-dihydro-2H-thiopyran-5-yl, 5,6-dihydro-2H-thiopyran-6-yl, 5,6-dihydro-2H-pyan-2-yl, 5,6-dihydro-2H-pyran-3-yl, 5,6-dihydro-2H-pyran-4-yl, 5,6-dihydro-2H-pyran-5-yl, 5,6-dihydro-2H-pyran-6-yl or dioxepan-5-yl, in particular tetrahydrothiopyran-3-yl, tetrahydropyran-3-yl or tetrahydropyran-4-yl, where each of the heterocyclic structures may furthermore carry from one to three radicals selected from the group consisting of hydroxyl, halogen as stated above, in particular chlorine and bromine, straight-chain or branched $C_1$-$C_4$-alkyl as stated above, in particular methyl and ethyl, partially or completely halogenated $C_1$-$C_4$-alkyl as stated above, in particular trifluoromethyl, $C_1$-$C_4$-alkoxy as stated above, in particular methoxy, and $C_1$-$C_4$-alkylthio as stated above, in particular methylthio and ethylthio; a 5-membered heteroaromatic structure containing from one to three hetero atoms selected from the group consisting of one or two nitrogen atoms and one oxygen or sulfur atom, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl or 1,3,4-triazol-2-yl, in particular isoxazolyl or pyrazolyl, where the heteroaromatic structure may furthermore carry from one to three radicals selected from the group consisting of cyano, halogen as stated above, in particular fluorine and chlorine, straight-chain or branched $C_1$-$C_4$-alkyl as stated above, in particular methyl, ethyl and isopropyl, partially and completely halogenated $C_1$-$C_4$-alkyl as stated above, in particular trifluoromethyl, $C_1$-$C_4$-alkoxy as stated above, in particular methoxy, partially or completely halogenated $C_1$-$C_4$-alkoxy as stated above, in particular trifluoromethoxy, $C_1$-$C_4$-alkylthio as stated above, in particular methylthio, $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 1-methylethenyl, $C_2$-$C_6$- alkenyloxy, such as ethenyloxy, 1-propenyloxy, 2-propenyloxy, 1-methyl-ethenyloxy, 1-butenyloxy, 2-butenyloxy, 3-butenyloxy, 1-methyl-1-propenyloxy, 2-methyl-1-propenyloxy, 1-methyl-1-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-1-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-2-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy or 1-ethyl-2-methyl-2-propenyloxy, in particular prop-2-enyloxy, $C_3$–$C_6$-alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy or 1-ethyl-1-methyl-2-propynyloxy, in particular prop-2-ynyloxy, and $C_1$–$C_4$-alkoxy-$C_1$–$C_4$-alkyl, such as methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, methoxyethyl, ethoxyethyl, n-propoxyethyl, (1-methylethoxy)ethyl, n-butoxyethyl, (1-methylpropoxy)ethyl, (2-methylpropoxy)ethyl, (1,1-dimethylethoxy)ethyl, 3-(methoxy)propyl, 2-(methoxy)propyl or 2-(ethoxy)propyl, preferably methoxymethyl or ethoxyethyl, phenyl or pyridyl, each of which may furthermore carry from one to three radicals selected from the group consisting of nitro, cyano, formyl, halogen as stated above, in particular fluorine and chlorine, straight-chain or branched $C_1$–$C_4$-alkyl as stated above, in particular methyl and ethyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy, $C_1$–$C_4$-alkylthio as stated above, in particular methylthio, $C_3$–$C_6$-alkenyl as stated above, in particular $C_3$- or $C_4$-alkenyl, preferably prop-2-enyl, $C_3$–$C_6$-alkenyloxy as stated above, in particular $C_3$- or $C_4$-alkenyloxy, preferably prop-2-enyloxy, $C_3$–$C_6$-alkynyl as stated above, in particular $C_3$- or $C_4$-alkynyl, preferably prop-2-ynyl, $C_3$–$C_6$-alkynyloxy as stated above, in particular $C_3$- or $C_4$-alkynyloxy, preferably prop-2-ynyloxy, and $NR^gR^h$, in which $R^g$ and $R^h$ have the abovementioned meanings, preferably hydrogen, acetyl or benzoyl;

particularly preferred phenyl and pyridyl groups are phenyl, 4-ethylphenyl, 4-propargyloxyphenyl, 2,4,6-trimethylphenyl, 4-benzoylamino-3-fluorophenyl, 4-formylphenyl and pyridyl;

W is a $C_1$–$C_6$-alkylene, a $C_3$–$C_6$-alkenylene or a $C_3$–$C_6$-alkynylene chain, such as methylene, ethylene, propylene, butylene, pentylene, hexylene, propenylene, prop-2-enylene, butenylene, but-2-enylene, but-3-enylene, pentenylene, pent-2-enylene, pent-3-enylene, pent-4-enylene, hex-1-enylene, hex-2-enylene, hex-3-enylene, hex-4-enylene, hex-5-enylene, prop-2-ynylene, but-2-ynylene, but-3-ynylene, pent-2-ynylene, pent-3-ynylene, pent-4-ynylene, hex-2-ynylene, hex-3-ynylene, hex-4-ylylene or hex-5-ynylene, where these groups may furthermore carry from one to three radicals from the group consisting of three halogen atoms as stated above, in particular fluorine and chlorine, three $C_1$–$C_3$-alkyl substituents, such as methyl, ethyl, n-propyl and isopropyl, in particular methyl and ethyl, and one methylene substituent; in the case of the unsaturated chains, both the cis and the trans form may occur; propylene, butylene, prop-2-enylene, but-2-enylene, but-3-enylene and but-3-ynylene are particularly preferred;

$C_3$–$C_6$-alkylene or $C_4$–$C_6$-alkenylene, both of which may furthermore carry from one to three alkyl radicals and in each case a methylene group may be replaced with an oxygen or sulfur atom, a sulfoxyl or sulfonyl group or a group —$N(R^i)$— in which $R^i$ is hydrogen, straight-chain or branched $C_1$–$C_4$-alkyl as stated above, in particular methyl or ethyl, $C_3$–$C_6$-alkenyl as stated above, in particular prop-2-enyl or but-2-enyl, or $C_3$–$C_6$-alkynyl as stated above, in particular prop-2-ynyl or but-2-ynyl, for example 3-oxapropylene, 3-azapropylene, 3-thiapropylene, 3-oxo-3-thiapropylene, 3,3-dioxo-3-thiapropylene, 3-oxabutylene, 3-azabutylene, 3-thiabutylene, 3-oxo-3-thiabutylene, 3,3-dioxo-3-thiabutylene, 4-oxabutylene, 4-azabutylene, 4-thiabutylene, 4-oxo-4-thiabutylene, 4,4-dioxo-4-thiabutylene, 4-oxabut-2-enylene, 4-azabut-2-enylene, 4-thiabut-2-enylene, 3-oxapentylene, 3-azapentylene, 3-thiapentylene, 3-oxo-3-thiapentylene, 3,3-dioxo-3-thiapentylene, 4-oxapentylene, 4-azapentylene, 4-thiapentylene, 4-oxo-4-thiapentylene, 4,4-dioxo-4-thiapentylene, 5-oxapentylene, 5-azapentylene, 5-thiapentylene, 5-oxo-5-thiapentylene, 5,5-dioxo-5-thiapentylene, 5-oxapent-3-enylene, 5-azapent-3-enylene, 5-thiapent-3-enylene, 3-oxahexylene, 3-azahexylene, 3-thiahexylene, 3-oxo-3-thiahexylene, 3,3-dioxo-3-thiahexylene, 4-oxahexylene, 4-azahexylene, 4-thiahexylene, 4-oxo-4-thiahexylene, 4,4-dioxo-4-thiahexylene, 5-oxahexylene, 5-azahexylene, 5-thiahexylene, 5-oxo-5- thiahexylene, 5,5-dioxo-5-thiahexylene, 6-oxahexylene, 6-azahexylene, 6-thiahexylene, 6-oxo-6-thiahexylene, 6,6-dioxo-6-thiahexylene, 6-oxahex-4-enylene, 6-azahex-4-enylene or 6-thiahex-4-enylene.

In the case of the unsaturated chains, the double bonds may be in either the cis or the trans configuration.

3-Oxapropylene, 2-methyl-3-oxapropylene, 3-oxabutylene and 4-oxabutylene are particularly preferred.

$R^f$ is hydrogen; vinyl;

a group —CH=CH—Z, in which Z is cyano;

halogen as stated above, in particular fluorine or chlorine;

straight-chain or branched $C_1$-$C_4$-alkyl as stated above, in particular methyl or 1,1-dimethylethyl;

partially or completely halogenated $C_1$-$C_4$-alkyl as stated above, in particular difluoromethyl, trifluoromethyl, 2,2,2-trifluoroethyl or pentafluoroethyl;

$C_3$-$C_6$-cycloalkyl, such as cyclopropyl, cyclobutyl, cyclopentyl or cyclohexyl, which in turn may furthermore carry from one to three substituents selected from the group consisting of hydroxyl, halogen as stated above, in particular fluorine or chlorine, straight-chain or branched $C_1$-$C_4$-alkyl as stated above, in particular methyl or isopropyl, partially or completely halogenated $C_1$-$C_4$-alkyl as stated above, in particular trifluoromethyl, and $C_1$-$C_4$-alkoxy as stated above, in particular methoxy;

carboxyl;

$C_1$-$C_8$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-ethylbutoxycarbonyl, 2,2-dimethylpropoxycarbonyl, 1-ethylpropoxycarbonyl, n-hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl;

benzyloxycarbonyl;

phenyl, thienyl or pyridyl, where these radicals may each furthermore carry from one to three substituents selected from the group consisting of nitro, cyano, halogen as stated above, in particular fluorine and chlorine, straight-chain or branched $C_1$-$C_4$-alkyl as stated above, in particular methyl, ethyl and 1-methylethyl, partially or completely halogenated $C_1$-$C_4$-alkyl as stated above, in particular trifluoromethyl, $C_1$-$C_4$-alkoxy as stated above, in particular methoxy and ethoxy, partially or completely halogenated $C_1$-$C_4$-alkoxy as stated above, in particular difluoromethoxy and trifluoromethoxy, $C_1$-$C_4$-alkylthio as stated above, in particular methylthio, and $C_3$-$C_6$-cycloalkyl as stated above, where the cycloalkyl substituent in turn may furthermore carry from one to three radicals selected from the group consisting of halogen as stated above, in particular fluorine and chlorine, straight-chain or branched $C_1$-$C_4$-alkyl as stated above, in particular methyl, partially or completely halogenated $C_1$-$C_4$-alkyl as stated above, in particular trifluoromethyl and $C_1$-$C_4$-alkoxy as stated above, in particular methoxy; ethynyl which may carry one of the following radicals: straight-chain or branched $C_1$-$C_4$-alkyl as stated above, in particular methyl and ethyl, where the alkyl radical in turn may furthermore carry from one to three substituents selected from the group consisting of hydroxyl, halogen as stated above, in particular fluorine and chlorine, straight-chain or branched $C_1$-$C_4$-alkyl as stated above, in particular methyl or ethyl, partially or completely halogenated $C_1$-$C_4$-alkyl as stated above, in particular trifluoromethyl, and $C_1$-$C_4$-alkoxy as stated above, in particular methoxy;

$C_3$-$C_6$-cycloalkyl, such as cyclopropyl, cyclobutyl, cyclopentyl or cyclohexyl, where the cycloalkyl radical in turn may furthermore carry from one to three substituents selected from the group consisting of hydroxyl, halogen as stated above, in particular fluorine and chlorine, straight-chain or branched $C_1$-$C_4$-alkyl as stated above, in particular methyl and ethyl, partially or completely halogenated $C_1$-$C_4$-alkyl as stated above, in particular trifluoromethyl, and $C_1$-$C_4$-alkoxy as stated above, in particular methoxy;

phenyl, thienyl or pyridyl, where each of these three aromatic radicals may furthermore carry from one to three substituents selected from the group consisting of nitro, cyano, halogen as stated above, in particular fluorine and chlorine, straight-chain or branched $C_1$-$C_4$-alkyl as stated above, in particular methyl and ethyl, partially or completely halogenated $C_1$-$C_4$-alkyl as stated above, in particular trifluoromethyl, $C_1$-$C_4$-alkoxy as stated above, in particular methoxy, partially or completely halogenated $C_1$-$C_4$-alkoxy as stated above, in particular trifluoromethoxy, and $C_1$-$C_4$-alkylthio as stated above, in particular methylthio;

phenyl; halophenyl, such as fluorophenyl, chlorophenyl or bromophenyl; dihalophenyl, such as difluorophenyl, dichlorophenyl, dibromophenyl, fluorochlorophenyl, fluorobromophenyl or chlorobromophenyl;

a 5-membered heteroaromatic group having from one to three hetero atoms selected from the group consisting of from one to three nitrogen atoms and one oxygen or sulfur atom, such as furanyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl,, 1,3,4-oxadiazolyl, 1,3,4-thiadiazolyl or 1,3,4-triazolyl, in particular furanyl or thienyl;

a 6-membered heteroaromatic group having from one to four nitrogen atoms as hetero atoms, such as pyridyl, pyrimidyl, pyrazyl, pyridazinyl, triazyl or tetrazyl, in particular pyridyl or pyrimidyl, where the phenyl and hetaryl groups may furthermore carry from one to three of the following radicals, but, in the case of the hetaryl radicals, not more radicals than the number of substitutable carbon atoms present:

nitro;

$C_1$-$C_4$-alkoxy as stated above, in particular methoxy;

$C_1$-$C_4$-alkylthio as stated above, in particular methylthio; partially or completely halogenated $C_1$-$C_4$-alkoxy, in particular $C_1$- or $C_2$-haloalkoxy as stated above, preferably trifluoromethoxy;

Z and —$NR^kR^l$, in which $R^k$ is hydrogen, straight-chain or branched $C_1$-$C_4$-alkyl as stated above, in particular methyl or ethyl, $C_3$-$C_6$- alkenyl as stated above, in particular prop-2-en-1-yl, or $C_3$-$C_6$alkynyl as stated above, in particular prop-2-yn-1-yl, and $R^j$ is hydrogen, straight-chain or branched $C_1$-$C_4$-alkyl as stated above, in particular methyl or ethyl, $C_3$-$C_6$-alkenyl as stated above, in particular prop-2-en-1-yl, $C_3$-$C_6$-alkynyl as stated above, in particular prop-2-yn-1-yl, straight-chain or branched $C_1$-$C_6$-acyl, such as acetyl, propionyl or butyryl, or benzoyl which may furthermore carry from one to three substituents selected from the group consisting of nitro, cyano, halogen as stated above, in particular fluorine and chlorine, straight-chain or branched $C_1$-$C_4$-alkyl as stated above, in particular methyl, partially or completely halogenated $C_1$-$C_4$-alkyl as stated above, in particular trifluoromethyl, $C_1$-$C_4$-alkoxy as stated above, in particular methoxy and ethoxy, and $C_1$-$C_4$-alkylthio as stated above, in particular methylthio.

In the case of a plurality of radicals Z, the substituents may be identical or different.

Very particularly preferred cyclohexenone derivatives of the formula II whose tolerance by crops can be improved by means of substituted thiochromenones I are shown in Tables 1 to 9 below:

TABLE 1

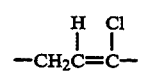

($R^b$, $R^d$, $R^e$ = H)

| No. | $R^a$ | $R^c$ | W | $R^f$ | Literature |
|---|---|---|---|---|---|
| A.001 | n-$C_3H_7$ | 2-(Ethylthio)propyl | —$CH_2CH_2$— | H | DE-A 2 822 304 |
| A.002 | $C_2H_5$ | 2-(Ethylthio)propyl | —$CH_2CH$=CCl— | H | US-A 4 440 566 |
| A.003 | n-$C_3H_7$ | 2-(Ethylthio)propyl | —$CH_2CH$=CCl— | H | US-A 4 440 566 |
| A.004 | n-$C_3H_7$ | Tetrahydrothiopyran-3-yl | —$CH_2CH_2$— | H | EP-A 71 707 |
| A.005 | $C_2H_5$ | Tetrahydrothiopyran-3-yl | —$CH_2CH_2$— | H | EP-A 71 707 |
| A.006 | $CH_3$ | Tetrahydrothiopyran-3-yl | —$CH_2CH$=$CCH_3$— | H | EP-A 71 707 |
| A.007 | n-$C_3H_7$ | Tetrahydropyran-3-yl | —$CH_2CH_2$— | H | EP-A 71 707 |
| A.008 | $C_2H_5$ | Tetrahydropyran-4-yl | —$CH_2CH$=CCl— | H | EP-A 142 741 |
| A.009 | n-$C_3H_7$ | Pyridin-3-yl | —$CH_2CH_2$— | H | EP-A 66 195 |
| A.010 | $C_2H_5$ | 4-$CH_3$-phenyl | —$CH_2CH_2$— | H | DE-A 24 39 104 |
| A.011 | $C_2H_5$ | 4-$C_2H_5$-phenyl | —$CH_2CH$=$CCH_3$— | H | DE-A 38 08 072 |
| A.012 | $C_2H_5$ | 2,4,6-$(CH_3)_3$-phenyl | —$CH_2CH_2$— | H | EP-A 88 301 |
| A.013 | n-$C_3H_7$ | 4-$CH_3$-cyclohexyl | —$CH_2CH$=CCl— | H | EP-A 88 299 |
| A.014 | n-$C_3H_7$ | 4-$CH_3$-cyclohexyl | —$CH_2CH$=$CCH_3$— | H | EP-A 88 299 |
| A.015 | $C_2H_5$ | 3-Isopropyl-isoxazol-5-yl | —$CH_2CH$=$CCH_3$— | H | EP-A 238 021 |
| A.016 | n-$C_3H_7$ | 3-Isopropyl-isoxazol-5-yl | —$CH_2CH$=$CCH_3$— | H | EP-A 238 021 |
| A.017 | $C_2H_5$ | 4-(HC≡C—$CH_2O$)-phenyl | —$CH_2CH$=CCl— | H | EP-A 137 174 |
| A.018 | n-$C_3H_7$ | 4-$C_2H_5OCH_2$-phenyl | —$CH_2CH_2$— | H | EP-A 2 137 200 |
| A.019 | n-$C_3H_7$ | 3,4-$Br_2$-tetrahydropyran-3-yl | —$CH_2CH_2$— | H | EP-A 230 235 |
| A.020 | n-$C_3H_7$ | 3,4-$Br_2$-tetrahydropyran-3-yl | —$CH_2CH$=CCl— | H | EP-A 230 235 |
| A.021 | n-$C_3H_7$ | 2,6,6-$(CH_3)_3$-cyclohex-1-enyl | —$CH_2CH$=CCl— | H | EP-A 46 860 |
| A.022 | n-$C_3H_7$ | Cyclohexyl | —$CH_2CH_2$— | H | JP-A 540 191 945 |
| A.023 | n-$C_3H_7$ | Cyclohex-1-enyl | —$CH_2CH_2$— | H | EP-A 46 860 |
| A.024 | $CH_3$ | 4-$CH_3$-3-cyclohexyl | —$CH_2CH$=CCl— | H | EP-A 88 299 |
| A.025 | n-$C_3H_7$ | 4-$CF_3$-phenyl | —$CH_2CH_2$— | H | EP-A 137 174 |
| A.026 | $C_2H_5$ | 2,6,6-$(CH_3)_3$-cyclohex-1-enyl | —$CH_2CH$=CCl— | H | EP-A 46 860 |
| A.027 | n-$C_3H_7$ | 2-$CH_3$-thiazol-4-yl | —$CH_2CH$=$CCH_3$— | H | EP-A 125 094 |
| A.028 | n-$C_3H_7$ | 2-$CH_3$-thiazol-4-yl | —$CH_2CH$=CCl— | H | EP-A 125 094 |
| A.029 | n-$C_3H_7$ | 2,4,6-$(CH_3)_3$-cyclohexyl | —$CH_2CH_2$— | H | EP-A 88 299 |
| A.030 | n-$C_3H_7$ | 3-$C_2H_5$S-4-OH-4-$CH_3$-cyclohexyl | —$CH_2CH$=CH— | H | EP-A 228 598 |
| A.031 | $C_2H_5$ | 3,4-$(OH)_2$-cyclohexyl | —$CH_2CH_2$— | H | EP-A 228 598 |
| A.032 | n-$C_3H_7$ | 1-$CH_3$-pyrazol-3-yl | —$CH_2CH_2$— | H | EP-A 66 195 |
| A.033 | n-$C_3H_7$ | 1-$CH_3$-pyrazol-3-yl | —$CH_2CH$=CCl— | H | EP-A 66 195 |
| A.034 | n-$C_3H_7$ | 2-$CH_3$-thiazol-4-yl | —$CH_2CH$=CH— | H | EP-A 125 094 |
| A.035 | n-$C_3H_7$ | $(CH_3CH_2S)_2$-methyl | —$CH_2CH_2CH_2$— | H | EP-A 230 260 |
| A.036 | n-$C_3H_7$ | 1-Oxo-tetrahydrothiopyran-3-yl | —$CH_2CH_2$— | H | EP-A 115 808 |
| A.037 | n-$C_3H_7$ | 1,1-Dioxo-tetrahydrothiopyran-3-yl | $CH_2CH_2$— | H | EP-A 115 808 |
| A.038 | n-$C_3H_7$ | 1,1-Dioxo-tetrahydrothiopyran-3-yl | —$CH_2CH$=CH— | H | Proceedings Brit. Crop-Protection Conference-weeds 1985 Vol. 1 P. 93-98 |
| A.039 | $CH_3$ | 4-F-phenyl-thioethyl | —$CH_2CH_2$— | H | EP-A 254 514 |
| A.040 | $C_2H_5$ | 4-F-phenyl-thioethyl | —$CH_2CH_2$— | H | EP-A 254 514 |
| A.041 | $C_2H_5$ | 4-F-phenyl-thioethyl | —$CH_2CH$=CH— | H | EP-A 254 514 |
| A.042 | $C_2H_5$ | 4-F-phenyl-thioethyl | —$CH_2CH$=$CHCH_2$— | H | EP-A 254 514 |
| A.043 | n-$C_3H_7$ | 4-F-phenyl-thioethyl | —$CH_2CH$=CH— | H | EP-A 254 514 |
| A.044 | n-$C_3H_7$ | Formyl | —$CH_2CH_2$— | H | EP-A 319 835 |
| A.045 | n-$C_3H_7$ | 1-$CH_3$S-cyclopropyl | —$CH_2CH_2$— | H | EP-A 243 313 |
| A.046 | n-$C_3H_7$ | 1-$CH_3$S-cyclopropyl | $\begin{array}{cc} H & Cl \\ \vert & \vert \\ \end{array}$ —$CH_2C$=C— | H | EP-A 243 313 |

TABLE 1-continued

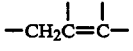

(R$^b$, R$^d$, R$^e$ = H)

| No. | R$^a$ | R$^c$ | W | R$^f$ | Literature |
|---|---|---|---|---|---|
| A.047 | C$_2$H$_5$ | 1-CH$_3$S-cyclopropyl | —CH$_2$C(H)=C(Cl)— | H | EP-A 243 313 |
| A.048 | C$_2$H$_5$ | 1-CH$_3$S-cyclopropyl | —CH$_2$C(H)=C(Cl)— | H | EP-A 243 313 |
| A.049 | C$_2$H$_5$ | 1-C$_2$H$_5$S-cyclopropyl | —CH$_2$C(H)=C(Cl)— | H | EP-A 243 313 |
| A.050 | n-C$_3$H$_7$ | 1-C$_2$H$_5$S-cyclopropyl | —CH$_2$C(H)=C(Cl)— | H | EP-A 243 313 |
| A.051 | C$_2$H$_5$ | Tetrahydrothiopyran-3-yl | —CH$_2$CH=CHCH$_2$— | 4-Cl-phenyl | EP-A 368 227 |
| A.052 | C$_2$H$_5$ | Tetrahydrothiopyran-3-yl | —CH$_2$CH$_2$CH=CH— | 4-Cl-phenyl | EP-A 368 227 |
| A.053 | C$_2$H$_5$ | Tetrahydrothiopyran-3-yl | —CH$_2$CH$_2$CH=CH— | 4-F-phenyl | EP-A 368 227 |
| A.054 | n-C$_3$H$_7$ | Tetrahydrothiopyran-3-yl | —CH$_2$CH$_2$CH=CH— | 4-F-phenyl | EP-A 368 227 |
| A.055 | C$_2$H$_5$ | Tetrahydrothiopyran-3-yl | —CH$_2$CH=CHCH$_2$— | Phenyl | EP-A 368 227 |
| A.056 | n-C$_3$H$_7$ | Tetrahydrothiopyran-3-yl | —CH$_2$— | 5-Cl-thien-2-yl | EP-A 177 913 |
| A.057 | C$_2$H$_5$ | Tetrahydrothiopyran-3-yl | —CH$_2$— | 5-Cl-thien-2-yl | EP-A 177 913 |
| A.058 | C$_2$H$_5$ | Tetrahydropyran-3-yl | —CH$_2$— | 5-Cl-thien-2-yl | EP-A 177 913 |
| A.059 | n-C$_3$H$_7$ | Tetrahydropyran-4-yl | —CH$_2$— | 5-Cl-thien-2-yl | EP-A 177 913 |
| A.060 | n-C$_3$H$_7$ | Tetrahydrothiopyran-3-yl | —CH$_2$— | Thien-2-yl | EP-A 177 913 |
| A.061 | CH$_3$ | Tetrahydropyran-3-yl | —CH$_2$— | Thien-2-yl | EP-A 177 913 |
| A.062 | C$_2$H$_5$ | Tetrahydropyran-4-yl | —CH$_2$— | Thien-2-yl | EP-A 177 913 |
| A.063 | C$_2$H$_5$ | Tetrahydropyran-3-yl | —(CH$_2$)$_4$— | 4-F-phenyl | DE-A 38 38 309 |
| A.064 | n-C$_3$H$_7$ | Tetrahydropyran-3-yl | —(CH$_2$)$_4$— | 4-F-phenyl | DE-A 38 38 309 |
| A.065 | C$_2$H$_5$ | Tetrahydrothiopyran-3-yl | —(CH$_2$)$_4$— | 4-F-phenyl | DE-A 38 38 309 |
| A.066 | n-C$_3$H$_7$ | Tetrahydrothiopyran-3-yl | —(CH$_2$)$_4$— | 4-F-phenyl | DE-A 38 38 309 |
| A.067 | C$_2$H$_5$ | Tetrahydropyran-3-yl | —(CH$_2$)$_4$— | 4-F-phenyl | DE-A 38 38 309 |
| A.068 | n-C$_3$H$_7$ | Tetrahydropyran-3-yl | —(CH$_2$)$_4$— | 4-F-phenyl | DE-A 38 38 309 |
| A.069 | C$_2$H$_5$ | Tetrahydropyran-3-yl | —(CH$_2$)$_4$— | 4-Cl-phenyl | DE-A 38 38 309 |
| A.070 | n-C$_3$H$_7$ | Tetrahydropyran-3-yl | —(CH$_2$)$_4$— | 4-Cl-phenyl | DE-A 38 38 309 |
| A.071 | C$_2$H$_5$ | Tetrahydropyran-4-yl | —(CH$_2$)$_4$— | 4-Cl-phenyl | DE-A 38 38 309 |
| A.072 | n-C$_3$H$_7$ | Tetrahydropyran-4-yl | —(CH$_2$)$_4$— | 4-Cl-phenyl | DE-A 38 38 309 |
| A.073 | C$_2$H$_5$ | Tetrahydrothiopyran-3-yl | —(CH$_2$)$_4$— | 4-Cl-phenyl | DE-A 38 38 309 |
| A.074 | n-C$_3$H$_7$ | Tetrahydrothiopyran-3-yl | —(CH$_2$)$_4$— | 4-Cl-phenyl | DE-A 38 38 309 |

TABLE 2

The following cyclohexenone derivatives of the formula II are known from EP-A 456 069

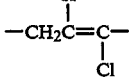

(R$^b$, R$^d$, R$^e$ = H)
(R$^c$ = Tetrahydrothiopyran-3-yl)

| Ex. | R$^a$ | W | R$^f$ |
|---|---|---|---|
| A.075 | C$_2$H$_5$ | —CH$_2$—CH=CH— | Phenyl |
| A.076 | n-C$_3$H$_7$ | —CH$_2$—CH=CH— | Phenyl |
| A.077 | C$_2$H$_5$ | —CH$_2$—CH=CH— | 4-Cl-phenyl |
| A.078 | n-C$_3$H$_7$ | —CH$_2$—CH=CH— | 4-Cl-phenyl |
| A.079 | C$_2$H$_5$ | —CH$_2$—CH=CH— | 4-F-phenyl |
| A.080 | n-C$_3$H$_7$ | —CH$_2$—CH=CH— | 4-F-phenyl |
| A.081 | C$_2$H$_5$ | —CH$_2$—CH=CH— | 2,4-Cl$_2$-phenyl |
| A.082 | n-C$_3$H$_7$ | —CH$_2$—CH=CH— | 2,4-Cl$_2$-phenyl |
| A.083 | C$_2$H$_5$ | —(CH$_2$)$_3$CH=CH— | Phenyl |
| A.084 | n-C$_3$H$_7$ | —(CH$_2$)$_3$CH=CH— | Phenyl |
| A.085 | C$_2$H$_5$ | —(CH$_2$)$_3$CH=CH— | 4-Cl-phenyl |
| A.086 | n-C$_3$H$_7$ | —(CH$_2$)$_3$CH=CH— | 4-Cl-phenyl |
| A.087 | C$_2$H$_5$ | —(CH$_2$)$_3$— | Phenyl |
| A.088 | n-C$_3$H$_7$ | —(CH$_2$)$_3$— | Phenyl |
| A.089 | C$_2$H$_5$ | —CH$_2$C(=CH$_2$)—CH$_2$— | Phenyl |

TABLE 2-continued

The following cyclohexenone derivatives of the formula II are known from EP-A 456 069

($R^b$, $R^d$, $R^e$ = H)
($R^c$ = Tetrahydrothiopyran-3-yl)

| Ex. | $R^a$ | W | $R^f$ |
|---|---|---|---|
| A.090 | n-$C_3H_7$ | —$CH_2C(=CH_2)CH_2$— | Phenyl |
| A.091 | $C_2H_5$ | —$CH_2CH=CH$— | 4-Br-phenyl |
| A.092 | n-$C_3H_7$ | —$CH_2CH=CH$— | 4-Br-phenyl |
| A.093 | $C_2H_5$ | —$CH_2CH=CH$— | 4-$CH_3$-phenyl |
| A.094 | n-$C_3H_7$ | —$CH_2CH=CH$— | 4-$CH_3$-phenyl |
| A.095 | $C_2H_5$ | —$CH_2CH=CH$— | 4-$CF_3$-phenyl |
| A.096 | n-$C_3H_7$ | —$CH_2CH=CH$— | 4-$CF_3$-phenyl |
| A.097 | $C_2H_5$ | —$CH_2CH=CH$— | 4-$C_6H_5$O-phenyl |
| A.098 | n-$C_3H_7$ | —$CH_2CH=CH$— | 4-$C_6H_5$O-phenyl |
| A.099 | $C_2H_5$ | —$CH_2CH=C(CH_3)$— | Phenyl |
| A.100 | n-$C_3H_7$ | —$CH_2CH=C(CH_3)$— | Phenyl |
| A.101 | $C_2H_5$ | —$CH_2CH=CH$— | 2-Cl-phenyl |
| A.102 | n-$C_3H_7$ | —$CH_2CH=CH$— | 2-Cl-phenyl |
| A.103 | $C_2H_5$ | —$(CH_2)_3$— | 4-F-phenyl |
| A.104 | n-$C_3H_7$ | —$(CH_2)_3$— | 4-F-phenyl |
| A.105 | $C_2H_5$ | —$(CH_2)_3$— | 2,4-$Cl_2$-phenyl |
| A.106 | n-$C_3H_7$ | —$(CH_2)_3$— | 2,4-$Cl_2$-phenyl |
| A.107 | $C_2H_5$ | —$(CH_2)_3$— | 4-Br-phenyl |
| A.108 | n-$C_3H_7$ | —$(CH_2)_3$— | 4-Br-phenyl |
| A.109 | $C_2H_5$ | —$(CH_2)_3$— | 2-Cl-phenyl |
| A.110 | n-$C_3H_7$ | —$(CH_2)_3$— | 2-Cl-phenyl |
| A.111 | $C_2H_5$ | —$(CH_2)_3$— | 4-Cl-phenyl |
| A.112 | n-$C_3H_7$ | —$(CH_2)_3$— | 4-Cl-phenyl |
| A.113 | $C_2H_5$ | —$CH_2CH=CH$— | 3,5-$Cl_2$-phenyl |
| A.114 | n-$C_3H_7$ | —$CH_2CH=CH$— | 3,5-$Cl_2$-phenyl |
| A.115 | $C_2H_5$ | —$CH_2CH_2CH(CH_3)$— | Phenyl |
| A.116 | n-$C_3H_7$ | —$CH_2CH_2CH(CH_3)$— | Phenyl |
| A.117 | $C_2H_5$ | —$(CH_2)_3$— | 3,5-$Cl_2$-phenyl |
| A.118 | n-$C_3H_7$ | —$(CH_2)_3$— | 3,5-$Cl_2$-phenyl |
| A.119 | $C_2H_5$ | —$CH_2CH_2C(=CH_2)$— | Phenyl |
| A.120 | n-$C_3H_7$ | —$CH_2CH_2C(=CH_2)$— | Phenyl |
| A.121 | $CH_3$ | —$CH_2CH=CH$— | 2,4-$Cl_2$-phenyl |
| A.122 | $CH_3$ | —$CH_2CH=CH$— | 4-Cl-phenyl |
| A.123 | $C_2H_5$ | —$(CH_2)_5$— | 4-Cl-phenyl |
| A.124 | n-$C_3H_7$ | —$(CH_2)_5$— | 4-Cl-phenyl |
| A.125 | $C_2H_5$ | —$CH_2CH=CH$— | 3,4-$Cl_2$-phenyl |
| A.126 | n-$C_3H_7$ | —$CH_2CH=CH$— | 3,4-$Cl_2$-phenyl |
| A.127 | $C_2H_5$ | —$CH_2CH(CH_3)CH_2$— | Phenyl |
| A.128 | n-$C_3H_7$ | —$CH_2CH(CH_3)CH_2$— | Phenyl |
| A.129 | $C_2H_5$ | —$(CH_2)_3$— | 3,4-$Cl_2$-phenyl |
| A.130 | n-$C_3H_7$ | —$(CH_2)_3$— | 3,4-$Cl_2$-phenyl |
| A.131 | $C_2H_5$ | —$CH_2CH(CH_3)CH_2$— | 4-F-phenyl |
| A.132 | n-$C_3H_7$ | —$CH_2CH(CH_3)CH_2$— | 4-F-phenyl |
| A.133 | $C_2H_5$ | —$CH_2CH(CH_3)CH_2$— | 4-Cl-phenyl |
| A.134 | n-$C_3H_7$ | —$CH_2CH(CH_3)CH_2$— | 4-Cl-phenyl |
| A.135 | $C_2H_5$ | —$CH_2CH_2C(CH_3)_2$— | 4-F-phenyl |
| A.136 | n-$C_3H_7$ | —$CH_2CH_2C(CH_3)_2$— | 4-F-phenyl |
| A.137 | $C_2H_5$ | —$CH_2CH_2C(CH_3)_2$— | 4-Cl-phenyl |
| A.138 | n-$C_3H_7$ | —$CH_2CH_2C(CH_3)_2$— | 4-Cl-phenyl |
| A.139 | $C_2H_5$ | —$(CH_2)_6$— | 4-Cl-phenyl |
| A.140 | n-$C_3H_7$ | —$(CH_2)_6$— | 4-Cl-phenyl |
| A.141 | $C_2H_5$ | —$(CH_2)_6$— | 4-F-phenyl |
| A.142 | n-$C_3H_7$ | —$(CH_2)_6$— | 4-F-phenyl |
| A.143 | $C_2H_5$ | —$(CH_2)_5$— | 4-F-phenyl |
| A.144 | n-$C_3H_7$ | —$(CH_2)_5$— | 4-F-phenyl |
| A.145 | $C_2H_5$ | —$CH_2CH(CH_3)$—$(CH_2)_3$— | 2-$CH_3$-phenyl |
| A.146 | n-$C_3H_7$ | —$CH_2CH(CH_3)$—$(CH_2)_3$— | 2-$CH_3$-phenyl |
| A.147 | $C_2H_5$ | —$CH_2CH=CH$— | 3-Br-phenyl |
| A.148 | n-$C_3H_7$ | —$CH_2CH=CH$— | 3-Br-phenyl |
| A.149 | $C_2H_5$ | —$CH_2CH=CH$— | 3-Cl-phenyl |
| A.150 | n-$C_3H_7$ | —$CH_2CH=CH$— | 3-Cl-phenyl |
| A.151 | $C_2H_5$ | —$CH_2CH=CH$— | 3-F-phenyl |
| A.152 | n-$C_3H_7$ | —$CH_2CH=CH$— | 3-F-phenyl |

TABLE 3

The following cyclohexenone derivatives of the formula II are known from EP-A 456 069

($R^b$, $R^d$, $R^e$ = H)
($R^c$ = Tetrahydropyran-3-yl)

| Ex. | $R^a$ | W | $R^f$ |
|---|---|---|---|
| A.153 | $C_2H_5$ | —$CH_2CH=CH$— | Phenyl |
| A.154 | n-$C_3H_7$ | —$CH_2CH=CH$— | Phenyl |
| A.155 | $C_2H_5$ | —$CH_2CH=CH$— | 4-Cl-phenyl |
| A.156 | n-$C_3H_7$ | —$CH_2CH=CH$— | 4-Cl-phenyl |
| A.157 | $C_2H_5$ | —$CH_2CH=CH$— | 4-F-phenyl |
| A.158 | n-$C_3H_7$ | —$CH_2CH=CH$— | 4-F-phenyl |
| A.159 | $C_2H_5$ | —$CH_2CH=CH$— | 2,4-$Cl_2$-phenyl |
| A.160 | n-$C_3H_7$ | —$CH_2CH=CH$— | 2,4-$Cl_2$-phenyl |
| A.161 | $C_2H_5$ | —$(CH_2)_3CH=CH$— | Phenyl |
| A.162 | n-$C_3H_7$ | —$(CH_2)_3CH=CH$— | Phenyl |
| A.163 | $C_2H_5$ | —$(CH_2)_3CH=CH$— | 4-Cl-phenyl |
| A.164 | n-$C_3H_7$ | —$(CH_2)_3CH=CH$— | 4-Cl-phenyl |
| A.165 | $C_2H_5$ | —$(CH_2)_3$— | Phenyl |
| A.166 | n-$C_3H_7$ | —$(CH_2)_3$— | Phenyl |

TABLE 3-continued

The following cyclohexenone derivatives of the formula II are known from EP-A 456 069

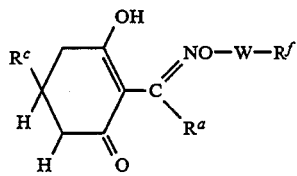

($R^b$, $R^d$, $R^e$ = H)
($R^c$ = Tetrahydropyran-3-yl)

| Ex. | $R^a$ | W | $R^f$ |
|---|---|---|---|
| A.167 | $C_2H_5$ | —CH$_2$C(=CH$_2$)—CH$_2$— | Phenyl |
| A.168 | n-$C_3H_7$ | —CH$_2$C(=CH$_2$)—CH$_2$— | Phenyl |
| A.170 | n-$C_3H_7$ | —CH$_2$CH=CH— | 4-Br-phenyl |
| A.171 | $C_2H_5$ | —CH$_2$CH=CH— | 4-CH$_3$-phenyl |
| A.172 | n-$C_3H_7$ | —CH$_2$CH=CH— | 4-CH$_3$-phenyl |
| A.173 | $C_2H_5$ | —CH$_2$CH=CH— | 4-CF$_3$-phenyl |
| A.174 | n-$C_3H_7$ | —CH$_2$CH=CH— | 4-CF$_3$-phenyl |
| A.175 | $C_2H_5$ | —CH$_2$CH=CH— | 4-$C_6H_5$O-phenyl |
| A.176 | n-$C_3H_7$ | —CH$_2$CH=CH— | 4-$C_6H_5$O-phenyl |
| A.177 | $C_2H_5$ | —CH$_2$CH=C(CH$_3$)— | Phenyl |
| A.178 | n-$C_3H_7$ | —CH$_2$CHC(CH$_3$)— | Phenyl |
| A.179 | $C_2H_5$ | —CH$_2$CH=CH— | 2-Cl-phenyl |
| A.180 | n-$C_3H_7$ | —CH$_2$CH=CH— | 2-Cl-phenyl |
| A.181 | $C_2H_5$ | —(CH$_2$)$_3$— | 4-F-phenyl |
| A.182 | n-$C_3H_7$ | —(CH$_2$)$_3$— | 4-F-phenyl |
| A.183 | $C_2H_5$ | —(CH$_2$)$_3$— | 2,4-Cl$_2$-phenyl |
| A.184 | n-$C_3H_7$ | —(CH$_2$)$_3$— | 2,4-Cl$_2$-phenyl |
| A.185 | $C_2H_5$ | —(CH$_2$)$_3$— | 2-Cl-phenyl |
| A.186 | n-$C_3H_7$ | —(CH$_2$)$_3$— | 2-Cl-phenyl |
| A.187 | $C_2H_5$ | —(CH$_2$)$_3$— | 4-Cl-phenyl |
| A.188 | n-$C_3H_7$ | —(CH$_2$)$_3$— | 4-Cl-phenyl |
| A.189 | $C_2H_5$ | —CH$_2$CH=CH$_2$— | 3,5-Cl$_2$-phenyl |
| A.190 | n-$C_3H_7$ | —CH$_2$CH=CH$_2$— | 3,5-Cl$_2$-phenyl |
| A.191 | $C_2H_5$ | —(CH$_2$)$_3$— | 3,5-Cl$_2$-phenyl |
| A.192 | n-$C_3H_7$ | —(CH$_2$)$_3$— | 3,5-Cl$_2$-phenyl |
| A.193 | $C_2H_5$ | —CH$_2$CH$_2$C(=CH$_2$)— | Phenyl |
| A.194 | n-$C_3H_7$ | —CH$_2$CH$_2$C(=CH$_2$)— | Phenyl |
| A.195 | CH$_3$ | —CH$_2$CH=CH$_2$— | 4-Br-phenyl |
| A.196 | $C_2H_5$ | —(CH$_2$)$_5$— | 4-Cl-phenyl |
| A.197 | n-$C_3H_7$ | —(CH$_2$)$_5$— | 4-Cl-phenyl |
| A.198 | $C_2H_5$ | —CH$_2$C(CH$_3$)—CH$_2$— | Phenyl |
| A.199 | n-$C_3H_7$ | —CH$_2$C(CH$_3$)—CH$_2$— | Phenyl |
| A.200 | $C_2H_5$ | —CH$_2$CH=CH$_2$— | 3,4-Cl$_2$-phenyl |
| A.201 | n-$C_3H_7$ | —CH$_2$CH=CH$_2$— | 3,4-Cl$_2$-phenyl |
| A.202 | $C_2H_5$ | —CH$_2$C(CH$_3$)—CH$_2$— | 4-F-phenyl |
| A.203 | n-$C_3H_7$ | —CH$_2$C(CH$_3$)—CH$_2$— | 4-F-phenyl |
| A.204 | $C_2H_5$ | —CH$_2$C(CH$_3$)—CH$_2$— | 4-Cl-phenyl |
| A.205 | n-$C_3H_7$ | —CH$_2$C(CH$_3$)—CH$_2$— | 4-Cl-phenyl |
| A.206 | $C_2H_5$ | —CH$_2$CH$_2$C(CH$_3$)$_2$— | 4-F-phenyl |
| A.207 | n-$C_3H_7$ | —CH$_2$CH$_2$C(CH$_3$)$_2$— | 4-F-phenyl |
| A.208 | $C_2H_5$ | —CH$_2$CH$_2$C(CH$_3$)$_2$— | 4-Cl-phenyl |
| A.209 | n-$C_3H_7$ | —CH$_2$CH$_2$C(CH$_3$)$_2$— | 4-Cl-phenyl |
| A.210 | $C_2H_5$ | —(CH$_2$)$_5$— | 4-F-phenyl |
| A.211 | n-$C_3H_7$ | —(CH$_2$)$_5$— | 4-F-phenyl |
| A.212 | $C_2H_5$ | —CH$_2$CH=CH— | 3-Br-phenyl |
| A.213 | n-$C_3H_7$ | —CH$_2$CH=CH— | 3-Br-phenyl |
| A.214 | $C_2H_5$ | —CH$_2$CH=CH— | 3-Cl-phenyl |
| A.215 | n-$C_3H_7$ | —CH$_2$CH=CH— | 3-Cl-phenyl |
| A.216 | $C_2H_5$ | —CH$_2$CH=CH— | 3-F-phenyl |
| A.217 | n-$C_3H_7$ | —CH$_2$CH=CH— | 3-F-phenyl |

TABLE 4

The following cyclohexenone derivatives of the formula II are known from EP-A 456 069

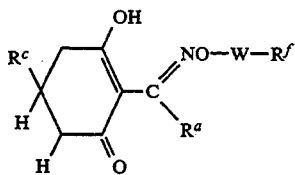

($R^b$, $R^d$, $R^e$ = H)
($R^c$ = Tetrahydropyran-4-yl)

| Ex. | $R^a$ | W | $R^f$ |
|---|---|---|---|
| A.218 | $C_2H_5$ | —$CH_2$—CH=CH— | Phenyl |
| A.219 | n-$C_3H_7$ | —$CH_2$—CH=CH— | Phenyl |
| A.220 | $C_2H_5$ | —$CH_2$—CH=CH— | 4-Cl-phenyl |
| A.221 | n-$C_3H_7$ | —$CH_2$—CH=CH— | 4-Cl-phenyl |
| A.222 | $C_2H_5$ | —$CH_2$—CH=CH— | 4-F-phenyl |
| A.223 | n-$C_3H_7$ | —$CH_2$—CH=CH— | 4-F-phenyl |
| A.224 | $C_2H_5$ | —$CH_2$—CH=CH— | 2,4-$Cl_2$-phenyl |
| A.225 | n-$C_3H_7$ | —$CH_2$—CH=CH— | 2,4-$Cl_2$-phenyl |
| A.226 | $C_2H_5$ | —$(CH_2)_3$CH=CH— | Phenyl |
| A.227 | n-$C_3H_7$ | —$(CH_2)_3$CH=CH— | Phenyl |
| A.228 | $C_2H_5$ | —$(CH_2)_3$CH=CH— | 4-Cl-phenyl |
| A.229 | n-$C_3H_7$ | —$(CH_2)_3$CH=CH— | 4-Cl-phenyl |
| A.230 | $C_2H_5$ | —$(CH_2)_3$— | Phenyl |
| A.231 | n-$C_3H_7$ | —$(CH_2)_3$— | Phenyl |
| A.232 | $C_2H_5$ | —$CH_2C(=CH_2)$—$CH_2$— | Phenyl |
| A.233 | n-$C_3H_7$ | —$CH_2C(=CH_2)$—$CH_2$— | Phenyl |
| A.234 | $C_2H_5$ | —$CH_2$CH=CH | 4-Br-phenyl |
| A.235 | n-$C_3H_7$ | —$CH_2$CH=CH | 4-Br-phenyl |
| A.236 | $C_2H_5$ | —$CH_2$CH=CH | 4-$CH_3$-phenyl |
| A.237 | n-$C_3H_7$ | —$CH_2$CH=CH | 4-$CH_3$-phenyl |
| A.238 | $C_2H_5$ | —$CH_2$CH=CH | 4-$CF_3$-phenyl |
| A.239 | n-$C_3H_7$ | —$CH_2$CH=CH | 4-$CF_3$-phenyl |
| A.240 | $C_2H_5$ | —$CH_2$CH=CH | 4-$C_6H_5$O-phenyl |
| A.241 | n-$C_3H_7$ | —$CH_2$CH=CH | 4-$C_6H_5$O-phenyl |
| A.242 | $C_2H_5$ | —$CH_2$CH=C($CH_3$)— | Phenyl |
| A.243 | n-$C_3H_7$ | —$CH_2$CH=C($CH_3$)— | Phenyl |
| A.244 | $C_2H_5$ | —$CH_2$CH=CH— | 2-Cl-phenyl |
| A.245 | n-$C_3H_7$ | —$CH_2$CH=CH— | 2-Cl-phenyl |
| A.246 | $C_2H_5$ | —$(CH_2)_3$— | 4-F-phenyl |
| A.247 | n-$C_3H_7$ | —$(CH_2)_3$— | 4-F-phenyl |
| A.248 | $C_2H_5$ | —$(CH_2)_3$— | 2,4-$Cl_2$-phenyl |
| A.249 | n-$C_3H_7$ | —$(CH_2)_3$— | 2,4-$Cl_2$-phenyl |
| A.250 | $C_2H_5$ | —$(CH_2)_3$— | 4-Br-phenyl |
| A.251 | $C_2H_5$ | —$(CH_2)_3$— | 2-Cl-phenyl |
| A.252 | n-$C_3H_7$ | —$(CH_2)_3$— | 2-Cl-phenyl |
| A.253 | $C_2H_5$ | —$(CH_2)_3$— | 4-Cl-phenyl |
| A.254 | n-$C_3H_7$ | —$(CH_2)_3$— | 4-Cl-phenyl |
| A.255 | $C_2H_5$ | —$CH_2$CH=CH— | 3,5-$Cl_2$-phenyl |
| A.256 | n-$C_3H_7$ | —$CH_2$CH=CH— | 3,5-$Cl_2$-phenyl |
| A.257 | $C_2H_5$ | —$CH_2CH_2$CH($CH_3$)— | Phenyl |
| A.258 | n-$C_3H_7$ | —$CH_2CH_2$CH($CH_3$)— | Phenyl |
| A.259 | $C_2H_5$ | —$(CH_2)_3$— | 3,5-$Cl_2$-phenyl |
| A.260 | n-$C_3H_7$ | —$(CH_2)_3$— | 3,5-$Cl_2$-phenyl |
| A.261 | $C_2H_5$ | —$CH_2CH_2$C(=$CH_2$)— | Phenyl |
| A.262 | n-$C_3H_7$ | —$CH_2CH_2$C(=$CH_2$)— | Phenyl |
| A.263 | $C_2H_5$ | —$(CH_2)_5$— | 4-Cl-phenyl |
| A.264 | n-$C_3H_7$ | —$(CH_2)_5$— | 4-Cl-phenyl |
| A.265 | $C_2H_5$ | —$CH_2$C($CH_3$)—$CH_2$— | Phenyl |
| A.266 | n-$C_3H_7$ | —$CH_2$C($CH_3$)—$CH_2$— | Phenyl |
| A.267 | $C_2H_5$ | —$CH_2$CH=CH— | 3,4-$Cl_2$-phenyl |
| A.268 | n-$C_3H_7$ | —$CH_2$CH=CH— | 3,4-$Cl_2$-phenyl |
| A.269 | $C_2H_5$ | —$(CH_2)_3$— | 3,4-$Cl_2$-phenyl |
| A.270 | $C_2H_5$ | —$CH_2$C($CH_3$)—$CH_2$— | 4-F-phenyl |
| A.271 | n-$C_3H_7$ | —$CH_2$C($CH_3$)—$CH_2$— | 4-F-phenyl |
| A.272 | $C_2H_5$ | —$CH_2$C($CH_3$)—$CH_2$— | 4-Cl-phenyl |
| A.273 | n-$C_3H_7$ | —$CH_2$C($CH_3$)—$CH_2$— | 4-Cl-phenyl |
| A.274 | $C_2H_5$ | —$CH_2CH_2$C($CH_3$)$_2$— | 4-F-phenyl |
| A.275 | n-$C_3H_7$ | —$CH_2CH_2$C($CH_3$)$_2$— | 4-F-phenyl |
| A.276 | $C_2H_5$ | —$CH_2CH_2$C($CH_3$)$_2$— | 4-Cl-phenyl |
| A.277 | n-$C_3H_7$ | —$CH_2CH_2$C($CH_3$)$_2$— | 4-Cl-phenyl |

TABLE 4-continued

The following cyclohexenone derivatives of the formula II are known from EP-A 456 069

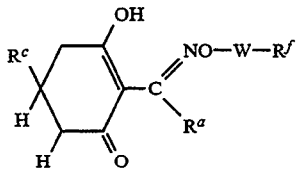

($R^b$, $R^d$, $R^e$ = H)
($R^c$ = Tetrahydropyran-4-yl)

| Ex. | $R^a$ | W | $R^f$ |
|---|---|---|---|
| A.278 | $C_2H_5$ | —(CH$_2$)$_6$— | 4-Cl-phenyl |
| A.279 | n-$C_3H_7$ | —(CH$_2$)$_6$— | 4-Cl-phenyl |
| A.280 | $C_2H_5$ | —(CH$_2$)$_6$— | 4-F-phenyl |
| A.281 | n-$C_3H_7$ | —(CH$_2$)$_6$— | 4-F-phenyl |
| A.282 | $C_2H_5$ | —(CH$_2$)$_5$— | 4-F-phenyl |
| A.283 | n-$C_3H_7$ | —(CH$_2$)$_5$— | 4-F-phenyl |
| A.284 | $C_2H_5$ | —CH$_2$CH(CH$_3$)—CH$_2$CH$_2$CH$_2$— | 2-CH$_3$-phenyl |
| A.285 | n-$C_3H_7$ | —CH$_2$CH(CH$_3$)—CH$_2$CH$_2$CH$_2$— | 2-CH$_3$-phenyl |
| A.286 | n-$C_3H_7$ | —CH$_2$CH=CH— | 3-F-phenyl |
| A.287 | $C_2H_5$ | —CH$_2$CH=CH— | 3-Br-phenyl |
| A.288 | n-$C_3H_7$ | —CH$_2$CH=CH— | 3-Br-phenyl |
| A.289 | $C_2H_5$ | —CH$_2$CH=CH— | 3-Cl-phenyl |
| A.290 | n-$C_3H_7$ | —CH$_2$CH=CH— | 3-Cl-phenyl |
| A.291 | $C_2H_5$ | —CH$_2$CH=CH— | 3-F-phenyl |

TABLE 5

The following cyclohexenone derivatives of the formula II are known from EP-A 456 069

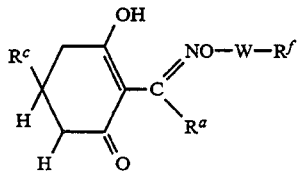

($R^b$, $R^d$, $R^e$ = H)

| Ex. | $R^c$ | $R^a$ | W | $R^f$ |
|---|---|---|---|---|
| A.292 | 2-Ethylthiopropyl | n-$C_3H_7$ | —(CH$_2$)$_3$— | Phenyl |
| A.293 | 2,4,6-Trimethyl-phenyl | $C_2H_5$ | —CH$_2$CH=CH— | 2,4-Cl$_2$-phenyl |
| A.294 | 2,4,6-Trimethyl-phenyl | $C_2H_5$ | —CH$_2$CH=CH— | 4-F-phenyl |
| A.295 | Phenyl | n-$C_3H_7$ | —CH$_2$CH=CH— | 4-F-phenyl |
| A.296 | 4-(Benzoylamino)-phenyl | n-$C_3H_7$ | —CH$_2$CH=CH— | 4-F-phenyl |
| A.297 | 5,6-Dihydrothio-pyran-3-yl | $C_2H_5$ | —CH$_2$CH=CH— | 4-F-phenyl |
| A.298 | Cyclohexyl | n-$C_3H_7$ | —CH$_2$CH=CH— | 4-F-phenyl |
| A.299 | 3-Isopropyl-isoxazol-5-yl | n-$C_3H_7$ | —CH$_2$CH=CH— | 4-F-phenyl |
| A.300 | 5,6-Dihydrothio-pyran-3-yl | $C_2H_5$ | —CH$_2$CH=CH— | 2,4-Cl$_2$-phenyl |
| A.301 | Cyclohex-3-enyl | n-$C_3H_7$ | —CH$_2$CH=CH— | 2,4-Cl$_2$-phenyl |
| A.302 | 3-Isopropyl-isoxazol-5-yl | n-$C_3H_7$ | —CH$_2$CH=CH— | 2,4-Cl$_2$-phenyl |
| A.303 | 3-Isopropyl-isothiazol-5-yl | $C_2H_5$ | —CH$_2$CH=CH— | 2,4-Cl$_2$-phenyl |
| A.304 | 4-Ethylphenyl | $C_2H_5$ | —CH$_2$CH=CH— | 2,4-Cl$_2$-phenyl |
| A.305 | 3-Isopropyl-isothiazol-5-yl | $C_2H_5$ | —CH$_2$CH=CH— | 4-F-phenyl |
| A.306 | N-Isopropyl-pyrrol-3-yl | n-$C_3H_7$ | —CH$_2$CH=CH— | 4-F-phenyl |
| A.307 | 3-Nitro-4-fluoro-phenyl | n-$C_3H_7$ | —CH$_2$CH=CH— | 4-Br-phenyl |
| A.308 | Cyclohex-3-enyl | n-$C_3H_7$ | —CH$_2$CH=CH— | 4-Br-phenyl |
| A.309 | Thien-3-yl | n-$C_3H_7$ | —CH$_2$CH=CH— | 4-Br-phenyl |
| A.310 | 4-(Prop-2-ynoxy)-phenyl | $C_2H_5$ | —CH$_2$CH=CH— | 4-Br-phenyl |
| A.311 | 2-Ethylthiopropyl | $C_2H_5$ | —CH$_2$CH=CH— | 2,4-Cl$_2$-phenyl |
| A.312 | 3-Isopropyl-isoxazol-5-yl | CH$_3$ | —CH$_2$CH=CH— | 4-Cl-phenyl |

TABLE 5-continued

The following cyclohexenone derivatives of the formula II are known from EP-A 456 069

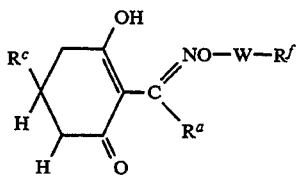

($R^b$, $R^d$, $R^e$ = H)

| Ex. | $R^c$ | $R^a$ | W | $R^f$ |
|---|---|---|---|---|
| A.313 | Ethoxycarbonyl | n-$C_3H_7$ | —$CH_2CH=CH$— | 4-Cl-phenyl |
| A.314 | 4-Ethylphenyl | $C_2H_5$ | —$CH_2CH=CH$— | 4-Cl-phenyl |
| A.315 | (dioxolane) | $C_2H_5$ | —$CH_2CH=CH$— | 4-Cl-phenyl |
| A.316 | Cyclohex-1-enyl | n-$C_3H_7$ | —$CH_2CH=CH$— | 4-Cl-phenyl |
| A.317 | 4-(Benzoylamino)-phenyl | n-$C_3H_7$ | —$CH_2CH=CH$— | 4-Cl-phenyl |
| A.318 | 4-(Prop-2-ynoxy)-phenyl | $C_2H_5$ | —$CH_2CH=CH$— | 4-Cl-phenyl |
| A.319 | 2-Ethylthiophenyl | n-$C_3H_7$ | —$(CH_2)_6$— | 4-Cl-phenyl |
| A.320 | 2,4,6-Trimethyl-phenyl | $C_2H_5$ | —$(CH_2)_6$— | 4-Cl-phenyl |
| A.321 | 2,4,6-Trimethyl-phenyl | $C_2H_5$ | —$(CH_2)_6$— | 4-F-phenyl |
| A.322 | 2-Ethylthiopropyl | n-$C_3H_7$ | —$(CH_2)_6$— | 4-F-phenyl |

TABLE 6

The following cyclohexenone derivatives of the formula II are known from EP-A 456 068 or are disclosed in P 40 33 193.8

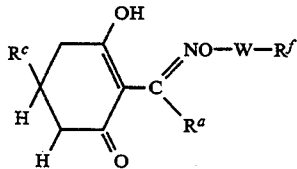

($R^b$, $R^d$, $R^3$ = H)

| Comp. no. | $R^c$ | $R^a$ | W | $R^f$ |
|---|---|---|---|---|
| A.323 | Tetrahydrothiopyran-3-yl | n-$C_3H_7$ | —$CH_2$—C≡C— | Phenyl |
| A.324 | Tetrahydrothiopyran-3-yl | n-$C_3H_7$ | —$CH_2$—C≡C—$CH_2$— | Phenyl |
| A.325 | Tetrahydrothiopyran-3-yl | $C_2H_5$ | —$CH_2$—C≡C—$CH_2$— | Phenyl |
| A.326 | Tetrahydropyran-3-yl | n-$C_3H_7$ | —$CH_2$—C≡C—$CH_2$— | Phenyl |
| A.327 | 2-Ethylthiopropyl | n-$C_3H_7$ | —$CH_2$—C≡C— | Phenyl |
| A.328 | 2-Ethylthiopropyl | n-$C_3H_7$ | —$CH_2$—C≡C—$CH_2$— | Phenyl |
| A.329 | Tetrahydropyran-4-yl | $C_2H_5$ | —$CH_2$—C≡C—$CH_2$— | Phenyl |
| A.330 | Tetrahydropyran-4-yl | n-$C_3H_7$ | —$CH_2$—C≡C—$CH_2$— | Phenyl |
| A.331 | Tetrahydropyran-4-yl | n-$C_3H_7$ | —$(CH_2)_3$—C≡C— | 4-F-phenyl |
| A.332 | Tetrahydropyran-4-yl | $C_2H_5$ | —$(CH_2)_3$—C≡C— | 4-F-phenyl |
| A.333 | Tetrahydrothiopyran-3-yl | $C_2H_5$ | —$(CH_2)_3$—C≡C— | 4-F-phenyl |
| A.334 | Tetrahydrothiopyran-3-yl | n-$C_3H_7$ | —$(CH_2)_3$—C≡C— | 4-F-phenyl |
| A.335 | Tetrahydropyran-3-yl | $C_2H_5$ | —$(CH_2)_3$—C≡C— | 4-F-phenyl |
| A.336 | Tetrahydropyran-3-yl | n-$C_3H_7$ | —$(CH_2)_3$—C≡C— | 4-F-phenyl |
| A.337 | Tetrahydrothiopyran-3-yl | $C_2H_5$ | —$CH_2CH_2$—C≡C— | 4-F-phenyl |
| A.338 | Tetrahydrothiopyran-3-yl | n-$C_3H_7$ | —$CH_2CH_2$—C≡C— | 4-F-phenyl |
| A.339 | Tetrahydropyran-3-yl | $C_2H_5$ | —$CH_2CH_2$—C≡C— | 4-F-phenyl |
| A.340 | Tetrahydropyran-3-yl | n-$C_3H_7$ | —$CH_2CH_2$—C≡C— | 4-F-phenyl |
| A.341 | Tetrahydropyran-4-yl | $C_2H_5$ | —$CH_2CH_2$—C≡C— | 4-F-phenyl |
| A.342 | Tetrahydropyran-4-yl | n-$C_3H_7$ | —$CH_2CH_2$—C≡C— | 4-F-phenyl |
| A.343 | 3-Isopropylisoxazol-5-yl | n-$C_3H_7$ | —$CH_2CH_2$—C≡C— | 4-F-phenyl |
| A.344 | 4-Methylphenyl | n-$C_3H_7$ | —$CH_2CH_2$—C≡C— | 4-F-phenyl |
| A.345 | 3,4-Dibromotetrahydro-pyran-3-yl | n-$C_3H_7$ | —$CH_2CH_2$—C≡C— | 4-F-phenyl |
| A.346 | Tetrahydrothiopyran-3-yl | n-$C_3H_7$ | —$CH_2CH_2$—C≡C— | 4-Cl-phenyl |
| A.347 | Tetrahydrothiopyran-3-yl | $C_2H_5$ | —$CH_2CH_2$—C≡C— | 4-Cl-phenyl |
| A.348 | Tetrahydropyran-3-yl | $C_2H_5$ | —$CH_2CH_2$—C≡C— | 4-Cl-phenyl |
| A.349 | Tetrahydropyran-3-yl | n-$C_3H_7$ | —$CH_2CH_2$—C≡C— | 4-Cl-phenyl |

TABLE 6-continued

The following cyclohexenone derivatives of the formula II are known from
EP-A 456 068 or are disclosed in P 40 33 193.8

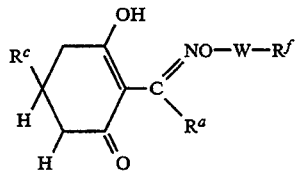

($R^b$, $R^d$, $R^3$ = H)

| Comp. no. | $R^c$ | $R^a$ | W | $R^f$ |
|---|---|---|---|---|
| A.350 | Tetrahydropyran-4-yl | $C_2H_5$ | —$CH_2CH_2$—C≡C— | 4-Cl-phenyl |
| A.351 | Tetrahydropyran-4-yl | n-$C_3H_7$ | —$CH_2CH_2$—C≡C— | 4-Cl-phenyl |
| A.352 | 3-Isopropylisoxazol-5-yl | n-$C_3H_7$ | —$CH_2CH_2$—C≡C— | 4-Cl-phenyl |
| A.353 | 4-Methylphenyl | n-$C_3H_7$ | —$CH_2CH_2$—C≡C— | 4-Cl-phenyl |
| A.354 | 3,4-Dibromotetrahydro-pyran-3-yl | n-$C_3H_7$ | —$CH_2CH_2$—C≡C— | 4-Cl-phenyl |
| A.355 | Tetrahydrothiopyran-3-yl | $C_2H_5$ | —$(CH_2)_3$—C≡C— | 4-Cl-phenyl |
| A.356 | Tetrahydrothiopyran-3-yl | n-$C_3H_7$ | —$(CH_2)_3$—C≡C— | 4-Cl-phenyl |
| A.357 | Tetrahydropyran-3-yl | $C_2H_5$ | —$(CH_2)_3$—C≡C— | 4-Cl-phenyl |
| A.358 | Tetrahydropyran-3-yl | n-$C_3H_7$ | —$(CH_2)_3$—C≡C— | 4-Cl-phenyl |
| A.359 | Tetrahydropyran-4-yl | $C_2H_5$ | —$(CH_2)_3$—C≡C— | 4-Cl-phenyl |
| A.360 | Tetrahydropyran-4-yl | n-$C_3H_7$ | —$(CH_2)_3$—C≡C— | 4-Cl-phenyl |
| A.361 | Tetrahydrothiopyran-3-yl | $C_2H_5$ | —$CH_2$—$CH_2$—C≡C— | 2-Thienyl |
| A.362 | Tetrahydrothiopyran-3-yl | n-$C_3H_7$ | —$CH_2$—$CH_2$—C≡C— | 2-Thienyl |
| A.363 | Tetrahydropyran-3-yl | $C_2H_5$ | —$CH_2$—$CH_2$—C≡C— | 2-Thienyl |
| A.364 | Tetrahydropyran-3-yl | n-$C_3H_7$ | —$CH_2$—$CH_2$—C≡C— | 2-Thienyl |
| A.365 | Tetrahydropyran-4-yl | $C_2H_5$ | —$CH_2$—$CH_2$—C≡C— | 2-Thienyl |
| A.366 | Tetrahydropyran-4-yl | n-$C_3H_7$ | —$CH_2$—$CH_2$—C≡C— | 2-Thienyl |
| A.367 | Tetrahydrothiopyran-3-yl | $C_2H_5$ | —$CH_2CH=C(CH_3)$—C≡C—**) | 4-Cl-phenyl |
| A.368 | Tetrahydrothiopyran-3-yl | n-$C_3H_7$ | —$CH_2CH=C(CH_3)$—C≡C—**) | 4-Cl-phenyl |
| A.369 | Tetrahydropyran-4-yl | $C_2H_5$ | —$CH_2CH=C(CH_3)$—C≡C—**) | 4-Cl-phenyl |
| A.370 | Tetrahydropyran-4-yl | n-$C_3H_7$ | —$CH_2CH=C(CH_3)$—C≡C—**) | 4-Cl-phenyl |
| A.371 | 2-Ethylthiopropyl | n-$C_3H_7$ | —$CH_2CH=C(CH_3)$—C≡C—**) | 4-Cl-phenyl |
| A.372 | 2,4,6-Trimethylphenyl | $C_2H_5$ | —$CH_2CH=C(CH_3)$—C≡C—**) | 4-Cl-phenyl |
| A.373 | Tetrahydrothiopropan-3-yl | $C_2H_5$ | —$CH_2CH=C(CH_3)$—C≡C—**) | 4-F-phenyl |
| A.374 | Tetrahydrothiopropan-3-yl | n-$C_3H_7$ | —$CH_2CH=C(CH_3)$—C≡C—**) | 4-F-phenyl |
| A.375 | Tetrahydropyran-4-yl | n-$C_3H_7$ | —$CH_2CH=C(CH_3)$—C≡C—**) | 4-F-phenyl |
| A.376 | Tetrahydropyran-4-yl | $C_2H_5$ | —$CH_2CH=C(CH_3)$—C≡C—**) | 4-F-phenyl |
| A.377 | 2-Ethylthiopropyl | n-$C_3H_7$ | —$CH_2CH=C(CH_3)$—C≡C—**) | 4-F-phenyl |

**) Z configuration at the double bond

TABLE 7

The following cyclohexenone derivatives of the formula II are
known from EP-A 456 118

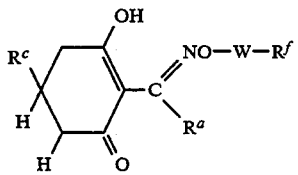

($R^b$, $R^d$, $R^e$ = H)

| No. | $R^a$ | $R^c$ | W | $R^f$ |
|---|---|---|---|---|
| A.378 | $C_2H_5$ | Tetrahydropyran-3-yl | —$(CH_2)_2$— | Furan-2-yl |
| A.379 | n-$C_3H_7$ | Tetrahydropyran-3-yl | —$(CH_2)_2$— | Furan-2-yl |
| A.380 | $C_2H_5$ | Tetrahydropyran-4-yl | —$(CH_2)_2$— | Furan-2-yl |
| A.381 | n-$C_3H_7$ | Tetrahydropyran-4-yl | —$(CH_2)_2$— | Furan-2-yl |
| A.382 | $C_2H_5$ | Tetrahydrothiopyran-3-yl | —$(CH_2)_2$— | Furan-2-yl |
| A.383 | n-$C_3H_7$ | Tetrahydrothiopyran-3-yl | —$(CH_2)_2$— | Furan-2-yl |
| A.384 | $C_2H_5$ | Tetrahydropyran-3-yl | —$(CH_2)_2$— | Thien-2-yl |
| A.385 | n-$C_3H_7$ | Tetrahydropyran-3-yl | —$(CH_2)_2$— | Thien-2-yl |
| A.386 | $C_2H_5$ | Tetrahydropyran-4-yl | —$(CH_2)_2$— | Thien-2-yl |
| A.387 | n-$C_3H_7$ | Tetrahydropyran-4-yl | —$(CH_2)_2$— | Thien-2-yl |
| A.388 | $C_2H_5$ | Tetrahydrothiopyran-3-yl | —$(CH_2)_2$— | Thien-2-yl |
| A.389 | n-$C_3H_7$ | Tetrahydrothiopyran-3-yl | —$(CH_2)_2$— | Thien-2-yl |
| A.390 | $C_2H_5$ | Tetrahydropyran-3-yl | —$(CH_2)_2$— | Pyrid-2-yl |
| A.391 | n-$C_3H_7$ | Tetrahydropyran-3-yl | —$(CH_2)_2$— | Pyrid-2-yl |
| A.392 | $C_2H_5$ | Tetrahydropyran-4-yl | —$(CH_2)_2$— | Pyrid-2-yl |
| A.393 | n-$C_3H_7$ | Tetrahydropyran-4-yl | —$(CH_2)_2$— | Pyrid-2-yl |
| A.394 | $C_2H_5$ | Tetrahydrothiopyran-3-yl | —$(CH_2)_2$— | Pyrid-2-yl |
| A.395 | n-$C_3H_7$ | Tetrahydrothiopyran-3-yl | —$(CH_2)_2$— | Pyrid-2-yl |

TABLE 7-continued

The following cyclohexenone derivatives of the formula II are known from EP-A 456 118

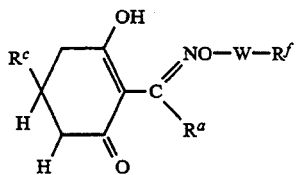

($R^b$, $R^d$, $R^e$ = H)

| No. | $R^a$ | $R^c$ | W | $R^f$ |
|---|---|---|---|---|
| A.396 | $C_2H_5$ | Tetrahydropyran-3-yl | —$(CH_2)_3$— | Furan-2-yl |
| A.397 | n-$C_3H_7$ | Tetrahydropyran-3-yl | —$(CH_2)_3$— | Furan-2-yl |
| A.398 | $C_2H_5$ | Tetrahydropyran-4-yl | —$(CH_2)_3$— | Furan-2-yl |
| A.399 | n-$C_3H_7$ | Tetrahydropyran-4-yl | —$(CH_2)_3$— | Furan-2-yl |
| A.400 | $C_2H_5$ | Tetrahydrothiopyran-3-yl | —$(CH_2)_3$— | Furan-2-yl |
| A.401 | n-$C_3H_7$ | Tetrahydrothiopyran-3-yl | —$(CH_2)_3$— | Furan-2-yl |
| A.402 | $C_2H_5$ | Tetrahydropyran-3-yl | —$(CH_2)_3$— | Thien-2-yl |
| A.403 | n-$C_3H_7$ | Tetrahydropyran-3-yl | —$(CH_2)_3$— | Thien-2-yl |
| A.404 | $C_2H_5$ | Tetrahydropyran-4-yl | —$(CH_2)_3$— | Thien-2-yl |
| A.405 | n-$C_3H_7$ | Tetrahydropyran-4-yl | —$(CH_2)_3$— | Thien-2-yl |
| A.406 | $C_2H_5$ | Tetrahydrothiopyran-3-yl | —$(CH_2)_3$— | Thien-2-yl |
| A.407 | n-$C_3H_7$ | Tetrahydrothiopyran-3-yl | —$(CH_2)_3$— | Thien-2-yl |
| A.408 | $C_2H_5$ | Tetrahydropyran-3-yl | —$(CH_2)_3$— | Thien-3-yl |
| A.409 | n-$C_3H_7$ | Tetrahydropyran-3-yl | —$(CH_2)_3$— | Thien-3-yl |
| A.410 | $C_2H_5$ | Tetrahydropyran-4-yl | —$(CH_2)_3$— | Thien-3-yl |
| A.411 | n-$C_3H_7$ | Tetrahydropyran-4-yl | —$(CH_2)_3$— | Thien-3-yl |
| A.412 | $C_2H_5$ | Tetrahydrothiopyran-3-yl | —$(CH_2)_3$— | Thien-3-yl |
| A.413 | n-$C_3H_7$ | Tetrahydrothiopyran-3-yl | —$(CH_2)_3$— | Thien-3-yl |
| A.414 | $C_2H_5$ | Tetrahydropyran-3-yl | —$(CH_2)_3$— | 1-$CH_3$-pyrrol-2-yl |
| A.415 | n-$C_3H_7$ | Tetrahydropyran-3-yl | —$(CH_2)_3$— | 1-$CH_3$-pyrrol-2-yl |
| A.416 | $C_2H_5$ | Tetrahydropyran-4-yl | —$(CH_2)_3$— | 1-$CH_3$-pyrrol-2-yl |
| A.417 | n-$C_3H_7$ | Tetrahydropyran-4-yl | —$(CH_2)_3$— | 1-$CH_3$-pyrrol-2-yl |
| A.418 | $C_2H_5$ | Tetrahydrothiopyran-3-yl | —$(CH_2)_3$— | 1-$CH_3$-pyrrol-2-yl |
| A.419 | n-$C_3H_7$ | Tetrahydrothiopyran-3-yl | —$(CH_2)_3$— | 1-$CH_3$-pyrrol-2-yl |
| A.420 | $C_2H_5$ | Tetrahydropyran-3-yl | —$CH_2CH(CH_3)$—$CH_2$— | Thien-2-yl |
| A.421 | n-$C_3H_7$ | Tetrahydropyran-3-yl | —$CH_2CH(CH_3)$—$CH_2$— | Thien-2-yl |
| A.422 | $C_2H_5$ | Tetrahydropyran-4-yl | —$CH_2CH(CH_3)$—$CH_2$— | Thien-2-yl |
| A.423 | n-$C_3H_7$ | Tetrahydropyran-4-yl | —$CH_2CH(CH_3)$—$CH_2$— | Thien-2-yl |
| A.424 | $C_2H_5$ | Tetrahydrothiopyran-3-yl | —$CH_2CH(CH_3)$—$CH_2$— | Thien-2-yl |
| A.425 | n-$C_3H_7$ | Tetrahydrothiopyran-3-yl | —$CH_2CH(CH_3)$—$CH_2$— | Thien-2-yl |
| A.426 | $C_2H_5$ | Tetrahydropyran-3-yl | —$CH_2CH(CH_3)$—$CH_2$— | Thien-3-yl |
| A.427 | n-$C_3H_7$ | Tetrahydropyran-3-yl | —$CH_2CH(CH_3)$—$CH_2$— | Thien-3-yl |
| A.428 | $C_2H_5$ | Tetrahydropyran-4-yl | —$CH_2CH(CH_3)$—$CH_2$— | Thien-3-yl |
| A.429 | n-$C_3H_7$ | Tetrahydropyran-4-yl | —$CH_2CH(CH_3)$—$CH_2$— | Thien-3-yl |
| A.430 | $C_2H_5$ | Tetrahydrothiopyran-3-yl | —$CH_2CH(CH_3)$—$CH_2$— | Thien-3-yl |
| A.431 | n-$C_3H_7$ | Tetrahydrothiopyran-3-yl | —$CH_2CH(CH_3)$—$CH_2$— | Thien-3-yl |
| A.432 | $C_2H_5$ | Tetrahydropyran-3-yl | —$CH_2CH(CH_3)$—$CH_2$— | 5-$CH_3$-thien-2-yl |
| A.433 | n-$C_3H_7$ | Tetrahydropyran-3-yl | —$CH_2CH(CH_3)$—$CH_2$— | 5-$CH_3$-thien-2-yl |
| A.434 | $C_2H_5$ | Tetrahydropyran-4-yl | —$CH_2CH(CH_3)$—$CH_2$— | 5-$CH_3$-thien-2-yl |
| A.435 | n-$C_3H_7$ | Tetrahydropyran-4-yl | —$CH_2CH(CH_3)$—$CH_2$— | 5-$CH_3$-thien-2-yl |
| A.436 | $C_2H_5$ | Tetrahydrothiopyran-3-yl | —$CH_2CH(CH_3)$—$CH_2$— | 5-$CH_3$-thien-2-yl |
| A.437 | n-$C_3H_7$ | Tetrahydrothiopyran-3-yl | —$CH_2CH(CH_3)$—$CH_2$— | 5-$CH_3$-thien-2-yl |
| A.438 | $C_2H_5$ | Tetrahydropyran-3-yl | —$CH_2CH=CH$— | Furan-2-yl |
| A.439 | n-$C_3H_7$ | Tetrahydropyran-3-yl | —$CH_2CH=CH$— | Furan-2-yl |
| A.440 | $C_2H_5$ | Tetrahydropyran-4-yl | —$CH_2CH=CH$— | Furan-2-yl |
| A.441 | n-$C_3H_7$ | Tetrahydropyran-4-yl | —$CH_2CH=CH$— | Furan-2-yl |
| A.442 | $C_2H_5$ | Tetrahydrothiopyran-3-yl | —$CH_2CH=CH$— | Furan-2-yl |
| A.443 | n-$C_3H_7$ | Tetrahydrothiopyran-3-yl | —$CH_2CH=CH$— | Furan-2-yl |
| A.444 | $C_2H_5$ | Tetrahydrothiopyran-3-yl | —$CH_2CH=CH$— | 5-Cl-thien-2-yl |
| A.445 | n-$C_3H_7$ | Tetrahydrothiopyran-3-yl | —$CH_2CH=CH$— | 5-Cl-thien-2-yl |
| A.446 | $C_2H_5$ | Tetrahydropyran-3-yl | —$CH_2CH=CH$— | Thien-2-yl |
| A.447 | n-$C_3H_7$ | Tetrahydropyran-3-yl | —$CH_2CH=CH$— | Thien-2-yl |
| A.448 | $C_2H_5$ | Tetrahydropyran-4-yl | —$CH_2CH=CH$— | Thien-2-yl |
| A.449 | n-$C_3H_7$ | Tetrahydropyran-4-yl | —$CH_2CH=CH$— | Thien-2-yl |
| A.450 | $C_2H_5$ | Tetrahydrothiopyran-3-yl | —$CH_2CH=CH$— | Thien-2-yl |
| A.451 | n-$C_3H_7$ | Tetrahydrothiopyran-3-yl | —$CH_2CH=CH$— | Thien-2-yl |
| A.452 | $C_2H_5$ | 2,4,6-Trimethylphenyl | —$CH_2CH=CH$— | Thien-2-yl |
| A.453 | $C_2H_5$ | Tetrahydropyran-3-yl | —$CH_2CH=CH$— | Thien-3-yl |
| A.454 | n-$C_3H_7$ | Tetrahydropyran-3-yl | —$CH_2CH=CH$— | Thien-3-yl |
| A.455 | $C_2H_5$ | Tetrahydropyran-4-yl | —$CH_2CH=CH$— | Thien-3-yl |
| A.456 | n-$C_3H_7$ | Tetrahydropyran-4-yl | —$CH_2CH=CH$— | Thien-3-yl |
| A.457 | $C_2H_5$ | Tetrahydrothiopyran-3-yl | —$CH_2CH=CH$— | Thien-3-yl |
| A.458 | n-$C_3H_7$ | Tetrahydrothiopyran-3-yl | —$CH_2CH=CH$— | Thien-3-yl |
| A.459 | $C_2H_5$ | Tetrahydropyran-3-yl | —$CH_2CH=CH$— | 5-$CH_3$-thien-2-yl |
| A.460 | n-$C_3H_7$ | Tetrahydropyran-3-yl | —$CH_2CH=CH$— | 5-$CH_3$-thien-2-yl |
| A.461 | $C_2H_5$ | Tetrahydropyran-4-yl | —$CH_2CH=CH$— | 5-$CH_3$-thien-2-yl |
| A.462 | n-$C_3H_7$ | Tetrahydropyran-4-yl | —$CH_2CH=CH$— | 5-$CH_3$-thien-2-yl |
| A.463 | $C_2H_5$ | Tetrahydrothiopyran-3-yl | —$CH_2CH=CH$— | 5-$CH_3$-thien-2-yl |

TABLE 7-continued

The following cyclohexenone derivatives of the formula II are known from EP-A 456 118

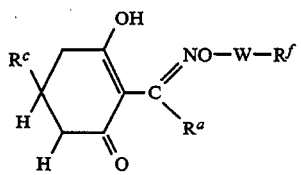

($R^b$, $R^d$, $R^e$ = H)

| No. | $R^a$ | $R^c$ | W | $R^f$ |
|---|---|---|---|---|
| A.464 | n-$C_3H_7$ | Tetrahydrothiopyran-3-yl | —$CH_2CH$=$CH$— | 5-$CH_3$-thien-2-yl |
| A.465 | $C_2H_5$ | Tetrahydropyran-3-yl | —$CH_2CH$=$CH$— | 4-Br-thien-2-yl |
| A.466 | n-$C_3H_7$ | Tetrahydropyran-3-yl | —$CH_2CH$=$CH$— | 4-Br-thien-2-yl |
| A.467 | $C_2H_5$ | Tetrahydropyran-4-yl | —$CH_2CH$=$CH$— | 4-Br-thien-2-yl |
| A.468 | n-$C_3H_7$ | Tetrahydropyran-4-yl | —$CH_2CH$=$CH$— | 4-Br-thien-2-yl |
| A.469 | $C_2H_5$ | Tetrahydrothiopyran-3-yl | —$CH_2CH$=$CH$— | 4-Br-thien-2-yl |
| A.470 | n-$C_3H_7$ | Tetrahydrothiopyran-3-yl | —$CH_2CH$=$CH$— | 4-Br-thien-2-yl |
| A.471 | $C_2H_5$ | Tetrahydropyran-3-yl | —$CH_2CH$=$CH$— | Pyrid-3-yl |
| A.472 | n-$C_3H_7$ | Tetrahydropyran-3-yl | —$CH_2CH$=$CH$— | Pyrid-3-yl |
| A.473 | $C_2H_5$ | Tetrahydropyran-4-yl | —$CH_2CH$=$CH$— | Pyrid-3-yl |
| A.474 | n-$C_3H_7$ | Tetrahydropyran-4-yl | —$CH_2CH$=$CH$— | Pyrid-3-yl |
| A.475 | $C_2H_5$ | Tetrahydrothiopyran-3-yl | —$CH_2CH$=$CH$— | Pyrid-3-yl |
| A.476 | n-$C_3H_7$ | Tetrahydrothiopyran-3-yl | —$CH_2CH$=$CH$— | Pyrid-3-yl |
| A.477 | $C_2H_5$ | Tetrahydropyran-3-yl | —$CH_2C(CH_3)$=$CH$— | Thien-2-yl |
| A.478 | n-$C_3H_7$ | Tetrahydropyran-3-yl | —$CH_2C(CH_3)$=$CH$— | Thien-2-yl |
| A.479 | $C_2H_5$ | Tetrahydropyran-4-yl | —$CH_2C(CH_3)$=$CH$— | Thien-2-yl |
| A.480 | n-$C_3H_7$ | Tetrahydropyran-4-yl | —$CH_2C(CH_3)$=$CH$— | Thien-2-yl |
| A.481 | $C_2H_5$ | Tetrahydrothiopyran-3-yl | —$CH_2C(CH_3)$=$CH$— | Thien-2-yl |
| A.482 | n-$C_3H_7$ | Tetrahydrothiopyran-3-yl | —$CH_2C(CH_3)$=$CH$— | Thien-2-yl |
| A.483 | $C_2H_5$ | Tetrahydropyran-3-yl | —$CH_2C(CH_3)$=$CH$— | Thien-3-yl |
| A.484 | n-$C_3H_7$ | Tetrahydropyran-3-yl | —$CH_2C(CH_3)$=$CH$— | Thien-3-yl |
| A.485 | $C_2H_5$ | Tetrahydropyran-4-yl | —$CH_2C(CH_3)$=$CH$— | Thien-3-yl |
| A.486 | n-$C_3H_7$ | Tetrahydropyran-4-yl | —$CH_2C(CH_3)$=$CH$— | Thien-3-yl |
| A.487 | $C_2H_5$ | Tetrahydrothiopyran-3-yl | —$CH_2C(CH_3)$=$CH$— | Thien-3-yl |
| A.488 | n-$C_3H_7$ | Tetrahydrothiopyran-3-yl | —$CH_2C(CH_3)$=$CH$— | Thien-3-yl |
| A.489 | $C_2H_5$ | Tetrahydropyran-3-yl | —$CH_2C(CH_3)$=$CH$— | 5-$CH_3$-thien-2-yl |
| A.490 | n-$C_3H_7$ | Tetrahydropyran-3-yl | —$CH_2C(CH_3)$=$CH$— | 5-$CH_3$-thien-2-yl |
| A.491 | $C_2H_5$ | Tetrahydropyran-4-yl | —$CH_2C(CH_3)$=$CH$— | 5-$CH_3$-thien-2-yl |
| A.492 | n-$C_3H_7$ | Tetrahydropyran-4-yl | —$CH_2C(CH_3)$=$CH$— | 5-$CH_3$-thien-2-yl |
| A.493 | $C_2H_5$ | Tetrahydrothiopyran-3-yl | —$CH_2C(CH_3)$=$CH$— | 5-$CH_3$-thien-2-yl |
| A.494 | n-$C_3H_7$ | Tetrahydrothiopyran-3-yl | —$CH_2C(CH_3)$=$CH$— | 5-$CH_3$-thien-2-yl |
| A.495 | $C_2H_5$ | Tetrahydropyran-3-yl | —$CH_2C(CH_3)$=$CH$— | 5-Cl-thien-2-yl |
| A.496 | n-$C_3H_7$ | Tetrahydropyran-3-yl | —$CH_2C(CH_3)$=$CH$— | 5-Cl-thien-2-yl |
| A.497 | $C_2H_5$ | Tetrahydropyran-4-yl | —$CH_2C(CH_3)$=$CH$— | 5-Cl-thien-2-yl |
| A.498 | n-$C_3H_7$ | Tetrahydropyran-4-yl | —$CH_2C(CH_3)$=$CH$— | 5-Cl-thien-2-yl |
| A.499 | $C_2H_5$ | Tetrahydrothiopyran-3-yl | —$CH_2C(CH_3)$=$CH$— | 5-Cl-thien-2-yl |
| A.500 | n-$C_3H_7$ | Tetrahydrothiopyran-3-yl | —$CH_2C(CH_3)$=$CH$— | 5-Cl-thien-2-yl |
| A.501 | $C_2H_5$ | Tetrahydropyran-3-yl | —$(CH_2)_4$— | Furan-2-yl |
| A.502 | n-$C_3H_7$ | Tetrahydropyran-3-yl | —$(CH_2)_4$— | Furan-2-yl |
| A.503 | $C_2H_5$ | Tetrahydropyran-4-yl | —$(CH_2)_4$— | Furan-2-yl |
| A.504 | n-$C_3H_7$ | Tetrahydropyran-4-yl | —$(CH_2)_4$— | Furan-2-yl |
| A.505 | $C_2H_5$ | Tetrahydrothiopyran-3-yl | —$(CH_2)_4$— | Furan-2-yl |
| A.506 | n-$C_3H_7$ | Tetrahydrothiopyran-3-yl | —$(CH_2)_4$— | Furan-2-yl |
| A.507 | $C_2H_5$ | Tetrahydropyran-3-yl | —$(CH_2)_4$— | 5-$CH_3$-furan-2-yl |
| A.508 | n-$C_3H_7$ | Tetrahydropyran-3-yl | —$(CH_2)_4$— | 5-$CH_3$-furan-2-yl |
| A.509 | $C_2H_5$ | Tetrahydropyran-4-yl | —$(CH_2)_4$— | 5-$CH_3$-furan-2-yl |
| A.510 | n-$C_3H_7$ | Tetrahydropyran-4-yl | —$(CH_2)_4$— | 5-$CH_3$-furan-2-yl |
| A.511 | $C_2H_5$ | Tetrahydrothiopyran-3-yl | —$(CH_2)_4$— | 5-$CH_3$-furan-2-yl |
| A.512 | n-$C_3H_7$ | Tetrahydrothiopyran-3-yl | —$(CH_2)_4$— | 5-$CH_3$-furan-2-yl |
| A.513 | $C_2H_5$ | Tetrahydropyran-3-yl | —$(CH_2)_4$— | Thien-2-yl |
| A.514 | n-$C_3H_7$ | Tetrahydropyran-3-yl | —$(CH_2)_4$— | Thien-2-yl |
| A.515 | $C_2H_5$ | Tetrahydropyran-4-yl | —$(CH_2)_4$— | Thien-2-yl |
| A.516 | n-$C_3H_7$ | Tetrahydropyran-4-yl | —$(CH_2)_4$— | Thien-2-yl |
| A.517 | $C_2H_5$ | Tetrahydrothiopyran-3-yl | —$(CH_2)_4$— | Thien-2-yl |
| A.518 | n-$C_3H_7$ | Tetrahydrothiopyran-3-yl | —$(CH_2)_4$— | Thien-2-yl |
| A.519 | $C_2H_5$ | Tetrahydropyran-3-yl | —$(CH_2)_4$— | 5-$CH_3$-thien-2-yl |
| A.520 | n-$C_3H_7$ | Tetrahydropyran-3-yl | —$(CH_2)_4$— | 5-$CH_3$-thien-2-yl |
| A.521 | $C_2H_5$ | Tetrahydropyran-4-yl | —$(CH_2)_4$— | 5-$CH_3$-thien-2-yl |
| A.522 | n-$C_3H_7$ | Tetrahydropyran-4-yl | —$(CH_2)_4$— | 5-$CH_3$-thien-2-yl |
| A.523 | $C_2H_5$ | Tetrahydrothiopyran-3-yl | —$(CH_2)_4$— | 5-$CH_3$-thien-2-yl |
| A.524 | n-$C_3H_7$ | Tetrahydrothiopyran-3-yl | —$(CH_2)_4$— | 5-$CH_3$-thien-2-yl |
| A.525 | $C_2H_5$ | Tetrahydropyran-3-yl | —$(CH_2)_4$— | 5-Cl-thien-2-yl |
| A.526 | n-$C_3H_7$ | Tetrahydropyran-3-yl | —$(CH_2)_4$— | 5-Cl-thien-2-yl |
| A.527 | $C_2H_5$ | Tetrahydropyran-4-yl | —$(CH_2)_4$— | 5-Cl-thien-2-yl |
| A.528 | n-$C_3H_7$ | Tetrahydropyran-4-yl | —$(CH_2)_4$— | 5-Cl-thien-2-yl |
| A.529 | $C_2H_5$ | Tetrahydrothiopyran-3-yl | —$(CH_2)_4$— | 5-Cl-thien-2-yl |
| A.530 | n-$C_3H_7$ | Tetrahydrothiopyran-3-yl | —$(CH_2)_4$— | 5-Cl-thien-2-yl |
| A.531 | $C_2H_5$ | Tetrahydropyran-3-yl | —$(CH_2)_4$— | 5-$C_2H_5$-thien-2-yl |

TABLE 7-continued

The following cyclohexenone derivatives of the formula II are known from EP-A 456 118

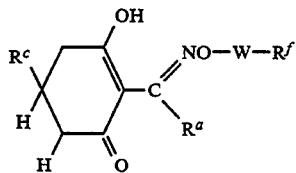

($R^b$, $R^d$, $R^e$ = H)

| No. | $R^a$ | $R^c$ | W | $R^f$ |
|---|---|---|---|---|
| A.532 | n-C$_3$H$_7$ | Tetrahydropyran-3-yl | —(CH$_2$)$_4$— | 5-C$_2$H$_5$-thien-2-yl |
| A.533 | C$_2$H$_5$ | Tetrahydropyran-4-yl | —(CH$_2$)$_4$— | 5-C$_2$H$_5$-thien-2-yl |
| A.534 | n-C$_3$H$_7$ | Tetrahydropyran-4-yl | —(CH$_2$)$_4$— | 5-C$_2$H$_5$-thien-2-yl |
| A.535 | C$_2$H$_5$ | Tetrahydrothiopyran-3-yl | —(CH$_2$)$_4$— | 5-C$_2$H$_5$-thien-2-yl |
| A.536 | n-C$_3$H$_7$ | Tetrahydrothiopyran-3-yl | —(CH$_2$)$_4$— | 5-C$_2$H$_5$-thien-2-yl |
| A.537 | C$_2$H$_5$ | Tetrahydropyran-3-yl | —(CH$_2$)$_4$— | 1-CH$_3$-pyrrol-2-yl |
| A.538 | n-C$_3$H$_7$ | Tetrahydropyran-3-yl | —(CH$_2$)$_4$— | 1-CH$_3$-pyrrol-2-yl |
| A.539 | C$_2$H$_5$ | Tetrahydropyran-4-yl | —(CH$_2$)$_4$— | 1-CH$_3$-pyrrol-2-yl |
| A.540 | n-C$_3$H$_7$ | Tetrahydropyran-4-yl | —(CH$_2$)$_4$— | 1-CH$_3$-pyrrol-2-yl |
| A.541 | C$_2$H$_5$ | Tetrahydrothiopyran-3-yl | —(CH$_2$)$_4$— | 1-CH$_3$-pyrrol-2-yl |
| A.542 | n-C$_3$H$_7$ | Tetrahydrothiopyran-3-yl | —(CH$_2$)$_4$— | 1-CH$_3$-pyrrol-2-yl |
| A.543 | C$_2$H$_5$ | Tetrahydropyran-4-yl | —CH$_2$CH$_2$CH=CH— | Furan-2-yl |
| A.544 | C$_2$H$_5$ | Tetrahydropyran-3-yl | —CH$_2$CH$_2$CH=CH— | Furan-3-yl |
| A.545 | C$_2$H$_5$ | Tetrahydropyran-4-yl | —CH$_2$CH$_2$CH=CH— | Furan-3-yl |
| A.546 | C$_2$H$_5$ | Tetrahydrothiopyran-3-yl | —CH$_2$CH$_2$CH=CH— | Furan-3-yl |
| A.547 | C$_2$H$_5$ | Tetrahydropyran-3-yl | —CH$_2$CH$_2$CH=CH— | Thien-2-yl |
| A.548 | n-C$_3$H$_7$ | Tetrahydropyran-3-yl | —CH$_2$CH$_2$CH=CH— | Thien-2-yl |
| A.549 | C$_2$H$_5$ | Tetrahydropyran-4-yl | —CH$_2$CH$_2$—CH=CH— | Thien-2-yl |
| A.550 | n-C$_3$H$_7$ | Tetrahydropyran-4-yl | —CH$_2$CH$_2$—CH=CH— | Thien-2-yl |
| A.551 | C$_2$H$_5$ | Tetrahydrothiopyran-3-yl | —CH$_2$CH$_2$—CH=CH— | Thien-2-yl |
| A.552 | n-C$_3$H$_7$ | Tetrahydrothiopyran-3-yl | —CH$_2$CH$_2$—CH=CH— | Thien-2-yl |
| A.553 | C$_2$H$_5$ | 2,4,6-Trimethylphenyl | —CH$_2$CH$_2$—CH=CH— | Thien-2-yl |
| A.554 | C$_2$H$_5$ | Tetrahydropyran-3-yl | —CH$_2$CH$_2$—CH=CH— | 5-CH$_3$-thien-2-yl |
| A.555 | n-C$_3$H$_7$ | Tetrahydropyran-3-yl | —CH$_2$CH$_2$—CH=CH— | 5-CH$_3$-thien-2-yl |
| A.556 | C$_2$H$_5$ | Tetrahydropyran-4-yl | —CH$_2$CH$_2$—CH=CH— | 5-CH$_3$-thien-2-yl |
| A.557 | n-C$_3$H$_7$ | Tetrahydropyran-4-yl | —CH$_2$CH$_2$—CH=CH— | 5-CH$_3$-thien-2-yl |
| A.558 | C$_2$H$_5$ | Tetrahydrothiopyran-3-yl | —CH$_2$CH$_2$—CH=CH— | 5-CH$_3$-thien-2-yl |
| A.559 | n-C$_3$H$_7$ | Tetrahydrothiopyran-3-yl | —CH$_2$CH$_2$—CH=CH— | 5-CH$_3$-thien-2-yl |
| A.560 | C$_2$H$_5$ | Tetrahydropyran-3-yl | —CH$_2$CH$_2$—CH=CH— | 5-Cl-thien-2-yl |
| A.561 | n-C$_3$H$_7$ | Tetrahydropyran-3-yl | —CH$_2$CH$_2$—CH=CH— | 5-Cl-thien-2-yl |
| A.562 | C$_2$H$_5$ | Tetrahydropyran-4-yl | —CH$_2$CH$_2$—CH=CH— | 5-Cl-thien-2-yl |
| A.563 | n-C$_3$H$_7$ | Tetrahydropyran-4-yl | —CH$_2$CH$_2$—CH=CH— | 5-Cl-thien-2-yl |
| A.564 | C$_2$H$_5$ | Tetrahydrothiopyran-3-yl | —CH$_2$CH$_2$—CH=CH— | 5-Cl-thien-2-yl |
| A.565 | n-C$_3$H$_7$ | Tetrahydrothiopyran-3-yl | —CH$_2$CH$_2$—CH=CH— | 5-Cl-thien-2-yl |
| A.566 | C$_2$H$_5$ | Tetrahydropyran-3-yl | —CH$_2$CH$_2$—CH=CH— | Thien-3-yl |
| A.567 | n-C$_3$H$_7$ | Tetrahydropyran-3-yl | —CH$_2$CH$_2$—CH=CH— | Thien-3-yl |
| A.568 | C$_2$H$_5$ | Tetrahydropyran-4-yl | —CH$_2$CH$_2$—CH=CH— | Thien-3-yl |
| A.569 | n-C$_3$H$_7$ | Tetrahydropyran-4-yl | —CH$_2$CH$_2$—CH=CH— | Thien-3-yl |
| A.570 | C$_2$H$_5$ | Tetrahydrothiopyran-3-yl | —CH$_2$CH$_2$—CH=CH— | Thien-3-yl |
| A.571 | n-C$_3$H$_7$ | Tetrahydrothiopyran-3-yl | —CH$_2$CH$_2$—CH=CH— | Thien-3-yl |
| A.572 | C$_2$H$_5$ | Tetrahydropyran-3-yl | —CH$_2$CH$_2$—CH=CH— | 2-Cl-thien-3-yl |
| A.573 | n-C$_3$H$_7$ | Tetrahydropyran-3-yl | —CH$_2$CH$_2$—CH=CH— | 2-Cl-thien-3-yl |
| A.574 | C$_2$H$_5$ | Tetrahydropyran-4-yl | —CH$_2$CH$_2$—CH=CH— | 2-Cl-thien-3-yl |
| A.575 | n-C$_3$H$_7$ | Tetrahydropyran-4-yl | —CH$_2$CH$_2$—CH=CH— | 2-Cl-thien-3-yl |
| A.576 | C$_2$H$_5$ | Tetrahydrothiopyran-3-yl | —CH$_2$CH$_2$—CH=CH— | 2-Cl-thien-3-yl |
| A.577 | n-C$_3$H$_7$ | Tetrahydrothiopyran-3-yl | —CH$_2$CH$_2$—CH=CH— | 2-Cl-thien-3-yl |
| A.578 | C$_2$H$_5$ | Tetrahydropyran-3-yl | —CH$_2$CH$_2$—CH=CH— | 5-Cl-thien-3-yl |
| A.579 | n-C$_3$H$_7$ | Tetrahydropyran-3-yl | —CH$_2$CH$_2$—CH=CH— | 5-Cl-thien-3-yl |
| A.580 | C$_2$H$_5$ | Tetrahydropyran-4-yl | —CH$_2$CH$_2$—CH=CH— | 5-Cl-thien-3-yl |
| A.581 | n-C$_3$H$_7$ | Tetrahydropyran-4-yl | —CH$_2$CH$_2$—CH=CH— | 5-Cl-thien-3-yl |
| A.582 | C$_2$H$_5$ | Tetrahydrothiopyran-3-yl | —CH$_2$CH$_2$—CH=CH— | 5-Cl-thien-3-yl |
| A.583 | n-C$_3$H$_7$ | Tetrahydrothiopyran-3-yl | —CH$_2$CH$_2$—CH=CH— | 5-Cl-thien-3-yl |
| A.584 | C$_2$H$_5$ | Tetrahydropyran-3-yl | —CH$_2$CH$_2$CH=CHCH$_3$— | Thien-2-yl |
| A.585 | n-C$_3$H$_7$ | Tetrahydropyran-3-yl | —CH$_2$CH$_2$CH=CHCH$_3$— | Thien-2-yl |
| A.586 | C$_2$H$_5$ | Tetrahydropyran-4-yl | —CH$_2$CH$_2$CH=CHCH$_3$— | Thien-2-yl |
| A.587 | n-C$_3$H$_7$ | Tetrahydropyran-4-yl | —CH$_2$CH$_2$CH=CHCH$_3$— | Thien-2-yl |
| A.588 | C$_2$H$_5$ | Tetrahydrothiopyran-3-yl | —CH$_2$CH$_2$CH=CHCH$_3$— | Thien-2-yl |
| A.589 | n-C$_3$H$_7$ | Tetrahydrothiopyran-3-yl | —CH$_2$CH$_2$CH=CHCH$_3$— | Thien-2-yl |
| A.590 | C$_2$H$_5$ | Tetrahydropyran-3-yl | —(CH$_2$)$_5$— | Furan-2-yl |
| A.591 | n-C$_3$H$_7$ | Tetrahydropyran-3-yl | —(CH$_2$)$_5$— | Furan-2-yl |
| A.592 | C$_2$H$_5$ | Tetrahydropyran-4-yl | —(CH$_2$)$_5$— | Furan-2-yl |
| A.593 | n-C$_3$H$_7$ | Tetrahydropyran-4-yl | —(CH$_2$)$_5$— | Furan-2-yl |
| A.594 | C$_2$H$_5$ | Tetrahydrothiopyran-3-yl | —(CH$_2$)$_5$— | Furan-2-yl |
| A.595 | n-C$_3$H$_7$ | Tetrahydrothiopyran-3-yl | —(CH$_2$)$_5$— | Furan-2-yl |
| A.596 | C$_2$H$_5$ | Tetrahydropyran-3-yl | —(CH$_2$)$_5$— | Thien-2-yl |
| A.597 | n-C$_3$H$_7$ | Tetrahydropyran-3-yl | —(CH$_2$)$_5$— | Thien-2-yl |
| A.598 | C$_2$H$_5$ | Tetrahydropyran-4-yl | —(CH$_2$)$_5$— | Thien-2-yl |
| A.599 | n-C$_3$H$_7$ | Tetrahydropyran-4-yl | —(CH$_2$)$_5$— | Thien-2-yl |

TABLE 7-continued

The following cyclohexenone derivatives of the formula II are known from EP-A 456 118

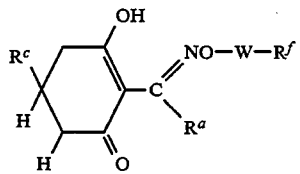

($R^b$, $R^d$, $R^e$ = H)

| No. | $R^a$ | $R^c$ | W | $R^f$ |
|---|---|---|---|---|
| A.600 | $C_2H_5$ | Tetrahydrothiopyran-3-yl | —(CH$_2$)$_5$— | Thien-2-yl |
| A.601 | n-$C_3H_7$ | Tetrahydrothiopyran-3-yl | —(CH$_2$)$_5$— | Thien-2-yl |
| A.602 | $C_2H_5$ | Tetrahydropyran-3-yl | —(CH$_2$)$_5$— | 1-CH$_3$-pyrrol-2-yl |
| A.603 | n-$C_3H_7$ | Tetrahydropyran-3-yl | —(CH$_2$)$_5$— | 1-CH$_3$-pyrrol-2-yl |
| A.604 | $C_2H_5$ | Tetrahydropyran-4-yl | —(CH$_2$)$_5$— | 1-CH$_3$-pyrrol-2-yl |
| A.605 | n-$C_3H_7$ | Tetrahydropyran-4-yl | —(CH$_2$)$_5$— | 1-CH$_3$-pyrrol-2-yl |
| A.606 | $C_2H_5$ | Tetrahydrothiopyran-3-yl | —(CH$_2$)$_5$— | 1-CH$_3$-pyrrol-2-yl |
| A.607 | n-$C_3H_7$ | Tetrahydrothiopyran-3-yl | —(CH$_2$)$_5$— | 1-CH$_3$-pyrrol-2-yl |
| A.608 | $C_2H_5$ | Tetrahydropyran-3-yl | —(CH$_2$)$_6$— | Furan-2-yl |
| A.609 | n-$C_3H_7$ | Tetrahydropyran-3-yl | —(CH$_2$)$_6$— | Furan-2-yl |
| A.610 | $C_2H_5$ | Tetrahydropyran-4-yl | —(CH$_2$)$_6$— | Furan-2-yl |
| A.611 | n-$C_3H_7$ | Tetrahydropyran-4-yl | —(CH$_2$)$_6$— | Furan-2-yl |
| A.612 | $C_2H_5$ | Tetrahydrothiopyran-3-yl | —(CH$_2$)$_6$— | Furan-2-yl |
| A.613 | n-$C_3H_7$ | Tetrahydrothiopyran-3-yl | —(CH$_2$)$_6$— | Furan-2-yl |
| A.614 | $C_2H_5$ | Tetrahydropyran-3-yl | —(CH$_2$)$_6$— | Thien-2-yl |
| A.615 | n-$C_3H_7$ | Tetrahydropyran-3-yl | —(CH$_2$)$_6$— | Thien-2-yl |
| A.616 | $C_2H_5$ | Tetrahydropyran-4-yl | —(CH$_2$)$_6$— | Thien-2-yl |
| A.617 | n-$C_3H_7$ | Tetrahydropyran-4-yl | —(CH$_2$)$_6$— | Thien-2-yl |
| A.618 | $C_2H_5$ | Tetrahydrothiopyran-3-yl | —(CH$_2$)$_6$— | Thien-2-yl |
| A.619 | n-$C_3H_7$ | Tetrahydrothiopyran-3-yl | —(CH$_2$)$_6$— | Thien-2-yl |
| A.620 | $C_2H_5$ | Tetrahydropyran-3-yl | —(CH$_2$)$_6$— | 1-CH$_3$-pyrrol-2-yl |
| A.621 | n-$C_3H_7$ | Tetrahydropyran-3-yl | —(CH$_2$)$_6$— | 1-CH$_3$-pyrrol-2-yl |
| A.622 | $C_2H_5$ | Tetrahydropyran-4-yl | —(CH$_2$)$_6$— | 1-CH$_3$-pyrrol-2-yl |
| A.623 | n-$C_3H_7$ | Tetrahydropyran-4-yl | —(CH$_2$)$_6$— | 1-CH$_3$-pyrrol-2-yl |
| A.624 | $C_2H_5$ | Tetrahydrothiopyran-3-yl | —(CH$_2$)$_6$— | 1-CH$_3$-pyrrol-2-yl |
| A.625 | n-$C_3H_7$ | Tetrahydrothiopyran-3-yl | —(CH$_2$)$_6$— | 1-CH$_3$-pyrrol-2-yl |

TABLE 8

The following cyclohexenone derivatives of the formula II are known from EP-A 456 112

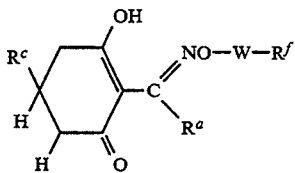

($R^b$, $R^d$, $R^e$ = H)

| No. | $R^a$ | $R^c$ | W | $R^f$ |
|---|---|---|---|---|
| A.626 | $C_2H_5$ | Tetrahydropyran-3-yl | —CH$_2$CH$_2$—O— | Phenyl |
| A.627 | n-$C_3H_7$ | Tetrahydropyran-3-yl | —CH$_2$CH$_2$—O— | Phenyl |
| A.628 | $C_2H_5$ | Tetrahydropyran-4-yl | —CH$_2$CH$_2$—O— | Phenyl |
| A.629 | n-$C_3H_7$ | Tetrahydropyran-4-yl | —CH$_2$CH$_2$—O— | Phenyl |
| A.630 | $C_2H_5$ | Tetrahydrothiopyran-3-yl | —CH$_2$CH$_2$—O— | Phenyl |
| A.631 | n-$C_3H_7$ | Tetrahydrothiopyran-3-yl | —CH$_2$CH$_2$—O— | Phenyl |
| A.632 | $C_2H_5$ | Tetrahydropyran-3-yl | —CH$_2$CH$_2$—O— | 2-F-phenyl |
| A.633 | n-$C_3H_7$ | Tetrahydropyran-3-yl | —CH$_2$CH$_2$—O— | 2-F-phenyl |
| A.634 | $C_2H_5$ | Tetrahydropyran-4-yl | —CH$_2$CH$_2$—O— | 2-F-phenyl |
| A.635 | n-$C_3H_7$ | Tetrahydropyran-4-yl | —CH$_2$CH$_2$—O— | 2-F-phenyl |
| A.636 | $C_2H_5$ | Tetrahydrothiopyran-3-yl | —CH$_2$CH$_2$—O— | 2-F-phenyl |
| A.637 | n-$C_3H_7$ | Tetrahydrothiopyran-3-yl | —CH$_2$CH$_2$—O— | 2-F-phenyl |
| A.638 | $C_2H_5$ | Tetrahydropyran-3-yl | —CH$_2$CH$_2$—O— | 3-F-phenyl |
| A.639 | n-$C_3H_7$ | Tetrahydropyran-3-yl | —CH$_2$CH$_2$—O— | 3-F-phenyl |
| A.640 | $C_2H_5$ | Tetrahydropyran-4-yl | —CH$_2$CH$_2$—O— | 3-F-phenyl |
| A.641 | n-$C_3H_7$ | Tetrahydropyran-4-yl | —CH$_2$CH$_2$—O— | 3-F-phenyl |
| A.642 | $C''H_5$ | Tetrahydrothiopyran-3-yl | —CH$_2$CH$_2$—O— | 3-F-phenyl |
| A.643 | n-$C_3H_7$ | Tetrahydrothiopyran-3-yl | —CH$_2$CH$_2$—O— | 3-F-phenyl |
| A.644 | $C_2H_5$ | Tetrahydropyran-3-yl | —CH$_2$CH$_2$—O— | 4-F-phenyl |
| A.645 | n-$C_3H_7$ | Tetrahydropyran-3-yl | —CH$_2$CH$_2$—O— | 4-F-phenyl |
| A.646 | $C_2H_5$ | Tetrahydropyran-4-yl | —CH$_2$CH$_2$—O— | 4-F-phenyl |
| A.647 | n-$C_3H_7$ | Tetrahydropyran-4-yl | —CH$_2$CH$_2$—O— | 4-F-phenyl |
| A.648 | $C_2H_5$ | Tetrahydrothiopyran-3-yl | —CH$_2$CH$_2$—O— | 4-F-phenyl |

TABLE 8-continued

The following cyclohexenone derivatives of the formula II are known from EP-A 456 112

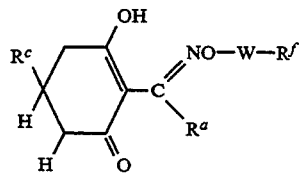

($R^b$, $R^d$, $R^e$ = H)

| No. | $R^a$ | $R^c$ | W | $R^f$ |
|---|---|---|---|---|
| A.649 | n-$C_3H_7$ | Tetrahydrothiopyran-3-yl | —$CH_2CH_2$—O— | 4-F-phenyl |
| A.650 | $C_2H_5$ | Tetrahydropyran-3-yl | —$CH_2CH_2$—O— | 2-Cl-phenyl |
| A.651 | n-$C_3H_7$ | Tetrahydropyran-3-yl | —$CH_2CH_2$—O— | 2-Cl-phenyl |
| A.652 | $C_2H_5$ | Tetrahydropyran-4-yl | —$CH_2CH_2$—O— | 2-Cl-phenyl |
| A.653 | n-$C_3H_7$ | Tetrahydropyran-4-yl | —$CH_2CH_2$—O— | 2-Cl-phenyl |
| A.654 | $C_2H_5$ | Tetrahydrothiopyran-3-yl | —$CH_2CH_2$—O— | 2-Cl-phenyl |
| A.655 | n-$C_3H_7$ | Tetrahydrothiopyran-3-yl | —$CH_2CH_2$—O— | 2-Cl-phenyl |
| A.656 | $C_2H_5$ | Tetrahydropyran-3-yl | —$CH_2CH_2$—O— | 3-Cl-phenyl |
| A.657 | n-$C_3H_7$ | Tetrahydropyran-3-yl | —$CH_2CH_2$—O— | 3-Cl-phenyl |
| A.658 | $C_2H_5$ | Tetrahydropyran-4-yl | —$CH_2CH_2$—O— | 3-Cl-phenyl |
| A.659 | n-$C_3H_7$ | Tetrahydropyran-4-yl | —$CH_2CH_2$—O— | 3-Cl-phenyl |
| A.660 | $C_2H_5$ | Tetrahydrothiopyran-3-yl | —$CH_2CH_2$—O— | 3-Cl-phenyl |
| A.661 | n-$C_3H_7$ | Tetrahydrothiopyran-3-yl | —$CH_2CH_2$—O— | 3-Cl-phenyl |
| A.662 | $C"H_5$ | Tetrahydropyran-3-yl | —$CH_2CH_2$—O— | 4-Cl-phenyl |
| A.663 | n-$C_3H_7$ | Tetrahydropyran-3-yl | —$CH_2CH_2$—O— | 4-Cl-phenyl |
| A.664 | $C_2H_5$ | Tetrahydropyran-4-yl | —$CH_2CH_2$—O— | 4-Cl-phenyl |
| A.665 | n-$C_3H_7$ | Tetrahydropyran-4-yl | —$CH_2CH_2$—O— | 4-Cl-phenyl |
| A.666 | $C_2H_5$ | Tetrahydrothiopyran-3-yl | —$CH_2CH_2$—O— | 4-Cl-phenyl |
| A.667 | n-$C_3H_7$ | Tetrahydrothiopyran-3-yl | —$CH_2CH_2$—O— | 4-Cl-phenyl |
| A.668 | $C_2H_5$ | Tetrahydropyran-3-yl | —$CH_2CH_2$—O— | 2-$CF_3$-phenyl |
| A.669 | n-$C_3H_7$ | Tetrahydropyran-3-yl | —$CH_2CH_2$—O— | 2-$CF_3$-phenyl |
| A.670 | $C_2H_5$ | Tetrahydropyran-4-yl | —$CH_2CH_2$—O— | 2-$CF_3$-phenyl |
| A.671 | n-$C_3H_7$ | Tetrahydropyran-4-yl | —$CH_2CH_2$—O— | 2-$CF_3$-phenyl |
| A.672 | $C_2H_5$ | Tetrahydrothiopyran-3-yl | —$CH_2CH_2$—O— | 2-$CF_3$-phenyl |
| A.673 | n-$C_3H_7$ | Tetrahydrothiopyran-3-yl | —$CH_2CH_2$—O— | 2-$CF_3$-phenyl |
| A.674 | $C_2H_5$ | Tetrahydropyran-3-yl | —$CH_2CH_2$—O— | 3-$CF_3$-phenyl |
| A.675 | n-$C_3H_7$ | Tetrahydropyran-3-yl | —$CH_2CH_2$—O— | 3-$CF_3$-phenyl |
| A.676 | $C_2H_5$ | Tetrahydropyran-4-yl | —$CH_2CH_2$—O— | 3-$CF_3$-phenyl |
| A.677 | n-$C_3H_7$ | Tetrahydropyran-4-yl | —$CH_2CH_2$—O— | 3-$CF_3$-phenyl |
| A.678 | $C_2H_5$ | Tetrahydrothiopyran-3-yl | —$CH_2CH_2$—O— | 3-$CF_3$-phenyl |
| A.679 | n-$C_3H_7$ | Tetrahydrothiopyran-3-yl | —$CH_2CH_2$—O— | 3-$CF_3$-phenyl |
| A.680 | $C_2H_5$ | Tetrahydropyran-3-yl | —$CH_2CH_2$—O— | 4-$CF_3$-phenyl |
| A.681 | n-$C§H_7$ | Tetrahydropyran-3-yl | —$CH_2CH_2$—O— | 4-$CF_3$-phenyl |
| A.682 | $C_2H_5$ | Tetrahydropyran-4-yl | —$CH_2CH_2$—O— | 4-$CF_3$-phenyl |
| A.683 | n-$C_3H_7$ | Tetrahydropyran-4-yl | —$CH_2CH_2$—O— | 4-$CF_3$-phenyl |
| A.684 | $C_2H_5$ | Tetrahydrothiopyran-3-yl | —$CH_2CH_2$—O— | 4-$CF_3$-phenyl |
| A.685 | n-$C_3H_7$ | Tetrahydrothiopyran-3-yl | —$CH_2CH_2$—O— | 4-$CF_3$-phenyl |
| A.686 | $C_2H_5$ | Tetrahydropyran-3-yl | —$CH_2CH_2$—O— | 2,4-$Cl_2$-phenyl |
| A.687 | n-$C_3H_7$ | Tetrahydropyran-3-yl | —$CH_2CH_2$—O— | 2,4-$Cl_2$-phenyl |
| A.688 | $C_2H_5$ | Tetrahydropyran-4-yl | —$CH_2CH_2$—O— | 2,4-$Cl_2$-phenyl |
| A.689 | n-$C_3H_7$ | Tetrahydropyran-4-yl | —$CH_2CH_2$—O— | 2,4-$Cl_2$-phenyl |
| A.690 | $C_2H_5$ | Tetrahydrothiopyran-3-yl | —$CH_2CH_2$—O— | 2,4-$Cl_2$-phenyl |
| A.691 | n-$C_3H_7$ | Tetrahydrothiopyran-3-yl | —$CH_2CH_2$—O— | 2,4-$Cl_2$-phenyl |
| A.692 | $C_2H_5$ | Tetrahydropyran-3-yl | —$CH_2CH_2$—O— | 2,4,6-$Cl_3$-phenyl |
| A.693 | n-$C_3H_7$ | Tetrahydropyran-3-yl | —$CH_2CH_2$—O— | 2,4,6-$Cl_3$-phenyl |
| A.694 | $C_2H_5$ | Tetrahydropyran-4-yl | —$CH_2CH_2$—O— | 2,4,6-$Cl_3$-phenyl |
| A.695 | n-$C_3H_7$ | Tetrahydropyran-4-yl | —$CH_2CH_2$—O— | 2,4,6-$Cl_3$-phenyl |
| A.696 | $C_2H_5$ | Tetrahydrothiopyran-3-yl | —$CH_2CH_2$—O— | 2,4,6-$Cl_3$-phenyl |
| A.697 | n-$C_3H_7$ | Tetrahydrothiopyran-3-yl | —$CH_2CH_2$—O— | 2,4,6-$Cl_3$-phenyl |
| A.698 | $C_2H_5$ | Tetrahydropyran-3-yl | —$CH_2CH_2$—O— | 4-$NO_2$-phenyl |
| A.699 | n-$C_3H_7$ | Tetrahydropyran-3-yl | —$CH_2CH_2$—O— | 4-$NO_2$-phenyl |
| A.700 | $C"H_5$ | Tetrahydropyran-4-yl | —$CH_2CH_2$—O— | 4-$NO_2$-phenyl |
| A.701 | n-$C_3H_7$ | Tetrahydropyran-4-yl | —$CH_2CH_2$—O— | 4-$NO_2$-phenyl |
| A.702 | $C_2H_5$ | Tetrahydrothiopyran-3-yl | —$CH_2CH_2$—O— | 4-$NO_2$-phenyl |
| A.703 | n-$C_3H_7$ | Tetrahydrothiopyran-3-yl | —$CH_2CH_2$—O— | 4-$NO_2$-phenyl |
| A.704 | $C_2H_5$ | Tetrahydropyran-3-yl | —$CH_2CH(CH_3)$—O— | Phenyl |
| A.705 | n-$C_3H_7$ | Tetrahydropyran-3-yl | —$CH_2CH(CH_3)$—O— | Phenyl |
| A.706 | $C_2H_5$ | Tetrahydropyran-4-yl | —$CH_2CH(CH_3)$—O— | Phenyl |
| A.707 | n-$C_3H_7$ | Tetrahydropyran-4-yl | —$CH_2CH(CH_3)$—O— | Phenyl |
| A.708 | $C_2H_5$ | Tetrahydrothiopyran-3-yl | —$CH_2CH(CH_3)$—O— | Phenyl |
| A.709 | n-$C_3H_7$ | Tetrahydrothiopyran-3-yl | —$CH_2CH(CH_3)$—O— | Phenyl |
| A.710 | $C_2H_5$ | Tetrahydropyran-3-yl | —$CH_2CH(CH_3)$—O— | 4-F-phenyl |
| A.711 | n-$C_3H_7$ | Tetrahydropyran-3-yl | —$CH_2CH(CH_3)$—O— | 4-F-phenyl |
| A.712 | $C_2H_5$ | Tetrahydropyran-4-yl | —$CH_2CH(CH_3)$—O— | 4-F-phenyl |
| A.713 | n-$C_3H_7$ | Tetrahydropyran-4-yl | —$CH_2CH(CH_3)$—O— | 4-F-phenyl |
| A.714 | $C_2H_5$ | Tetrahydrothiopyran-3-yl | —$CH_2CH(CH_3)$—O— | 4-F-phenyl |
| A.715 | n-$C_3H_7$ | Tetrahydrothiopyran-3-yl | —$CH_2CH(CH_3)$—O— | 4-F-phenyl |
| A.716 | $C_2H_5$ | Tetrahydropyran-3-yl | —$CH_2CH(CH_3)$—O— | 4-Cl-phenyl |

TABLE 8-continued

The following cyclohexenone derivatives of the formula II are known from EP-A 456 112

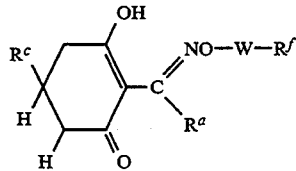

($R^b$, $R^d$, $R^e$ = H)

| No. | $R^a$ | $R^c$ | W | $R^f$ |
|---|---|---|---|---|
| A.717 | n-$C_3H_7$ | Tetrahydropyran-3-yl | —$CH_2CH(CH_3)$—O— | 4-Cl-phenyl |
| A.718 | $C_2H_5$ | Tetrahydropyran-4-yl | —$CH_2CH(CH_3)$—O— | 4-Cl-phenyl |
| A.719 | n-$C_3H_7$ | Tetrahydropyran-4-yl | —$CH_2CH(CH_3)$—O— | 4-Cl-phenyl |
| A.720 | $C''H_5$ | Tetrahydrothiopyran-3-yl | —$CH_2CH(CH_3)$—O— | 4-Cl-phenyl |
| A.721 | n-$C_3H_7$ | Tetrahydrothiopyran-3-yl | —$CH_2CH(CH_3)$—O— | 4-Cl-phenyl |
| A.722 | $C_2H_5$ | Tetrahydropyran-3-yl | —$CH_2CH_2$—S— | Phenyl |
| A.723 | n-$C_3H_7$ | Tetrahydropyran-3-yl | —$CH_2CH_2$—S— | Phenyl |
| A.724 | $C_2H_5$ | Tetrahydropyran-4-yl | —$CH_2CH_2$—S— | Phenyl |
| A.725 | n-$C_3H_7$ | Tetrahydropyran-4-yl | —$CH_2CH_2$—S— | Phenyl |
| A.726 | $C_2H_5$ | Tetrahydrothiopyran-3-yl | —$CH_2CH_2$—S— | Phenyl |
| A.727 | n-$C_3H_7$ | Tetrahydrothiopyran-3-yl | —$CH_2CH_2$—S— | Phenyl |
| A.728 | $C_2H_5$ | Tetrahydropyran-3-yl | —$CH_2CH_2$—S— | 4-F-phenyl |
| A.729 | n-$C_3H_7$ | Tetrahydropyran-3-yl | —$CH_2CH_2$—S— | 4-F-phenyl |
| A.730 | $C_2H_5$ | Tetrahydropyran-4-yl | —$CH_2CH_2$—S— | 4-F-phenyl |
| A.731 | n-$C_3H_7$ | Tetrahydropyran-4-yl | —$CH_2CH_2$—S— | 4-F-phenyl |
| A.732 | $C_2H_5$ | Tetrahydrothiopyran-3-yl | —$CH_2CH_2$—S— | 4-F-phenyl |
| A.733 | n-$C_3H_7$ | Tetrahydrothiopyran-3-yl | —$CH_2CH_2$—S— | 4-F-phenyl |
| A.734 | $C_2H_5$ | Tetrahydropyran-3-yl | —$CH_2CH_2$—S— | 4-Cl-phenyl |
| A.735 | n-$C_3H_7$ | Tetrahydropyran-3-yl | —$CH_2CH_2$—S— | 4-Cl-phenyl |
| A.736 | $C_2H_5$ | Tetrahydropyran-4-yl | —$CH_2CH_2$—S— | 4-Cl-phenyl |
| A.737 | n-$C_3H_7$ | Tetrahydropyran-4-yl | —$CH_2CH_2$—S— | 4-Cl-phenyl |
| A.738 | $C_2H_5$ | Tetrahydrothiopyran-3-yl | —$CH_2CH_2$—S— | 4-Cl-phenyl |
| A.739 | n-$C_3H_7$ | Tetrahydrothiopyran-3-yl | —$CH_2CH_2$—S— | 4-Cl-phenyl |
| A.740 | $C_2H_5$ | Tetrahydropyran-3-yl | —$CH_2CH_2$—S— | 2-Cl-phenyl |
| A.741 | n-$C_3H_7$ | Tetrahydropyran-3-yl | —$CH_2CH_2$—S— | 2-Cl-phenyl |
| A.742 | $C_2H_5$ | Tetrahydropyran-4-yl | —$CH_2CH_2$—S— | 2-Cl-phenyl |
| A.743 | n-$C_3H_7$ | Tetrahydropyran-4-yl | —$CH_2CH_2$—S— | 2-Cl-phenyl |
| A.744 | $C_2H_5$ | Tetrahydrothiopyran-3-yl | —$CH_2CH_2$—S— | 2-Cl-phenyl |
| A.745 | n-$C_3H_7$ | Tetrahydrothiopyran-3-yl | —$CH_2CH_2$—S— | 2-Cl-phenyl |
| A.746 | $C_2H_5$ | Tetrahydropyran-3-yl | —$CH_2CH_2$—S— | 2,6-$Cl_2$-phenyl |
| A.747 | n-$C_3H_7$ | Tetrahydropyran-3-yl | —$CH_2CH_2$—S— | 2,6-$Cl_2$-phenyl |
| A.748 | $C_2H_5$ | Tetrahydropyran-4-yl | —$CH_2CH_2$—S— | 2,6-$Cl_2$-phenyl |
| A.749 | n-$C_3H_7$ | Tetrahydropyran-4-yl | —$CH_2CH_2$—S— | 2,6-$Cl_2$-phenyl |
| A.750 | $C_2H_5$ | Tetrahydrothiopyran-3-yl | —$CH_2CH_2$—S— | 2,6-$Cl_2$-phenyl |
| A.751 | n-$C_3H_7$ | Tetrahydrothiopyran-3-yl | —$CH_2CH_2$—S— | 2,6-$Cl_2$-phenyl |
| A.752 | $C_2H_5$ | Tetrahydropyran-3-yl | —$(CH_2)_3$—O— | Phenyl |
| A.753 | n-$C_3H_7$ | Tetrahydropyran-3-yl | —$(CH_2)_3$—O— | Phenyl |
| A.754 | $C_2H_5$ | Tetrahydropyran-4-yl | —$(CH_2)_3$—O— | Phenyl |
| A.755 | n-$C_3H_7$ | Tetrahydropyran-4-yl | —$(CH_2)_3$—O— | Phenyl |
| A.756 | $C_2H_5$ | Tetrahydrothiopyran-3-yl | —$(CH_2)_3$—O— | Phenyl |
| A.757 | n-$C_3H_7$ | Tetrahydrothiopyran-3-yl | —$(CH_2)_3$—O— | Phenyl |
| A.758 | $C_2H_5$ | Tetrahydropyran-3-yl | —$(CH_2)_3$—O— | 2-F-phenyl |
| A.759 | n-$C_3H_7$ | Tetrahydropyran-3-yl | —$(CH_2)_3$—O— | 2-F-phenyl |
| A.760 | $C''H_5$ | Tetrahydropyran-4-yl | —$(CH_2)_3$—O— | 2-F-phenyl |
| A.761 | n-$C_3H_7$ | Tetrahydropyran-4-yl | —$(CH_2)_3$—O— | 2-F-phenyl |
| A.762 | $C_2H_5$ | Tetrahydrothiopyran-3-yl | —$(CH_2)_3$—O— | 2-F-phenyl |
| A.763 | n-$C_3H_7$ | Tetrahydrothiopyran-3-yl | —$(CH_2)_3$—O— | 2-F-phenyl |
| A.764 | $C_2H_5$ | Tetrahydropyran-3-yl | —$(CH_2)_3$—O— | 3-F-phenyl |
| A.765 | n-$C_3H_7$ | Tetrahydropyran-3-yl | —$(CH_2)_3$—O— | 3-F-phenyl |
| A.766 | $C_2H_5$ | Tetrahydropyran-4-yl | —$(CH_2)_3$—O— | 3-F-phenyl |
| A.767 | n-$C_3H_7$ | Tetrahydropyran-4-yl | —$(CH_2)_3$—O— | 3-F-phenyl |
| A.768 | $C_2H_5$ | Tetrahydrothiopyran-3-yl | —$(CH_2)_3$—O— | 3-F-phenyl |
| A.769 | n-$C_3H_7$ | Tetrahydrothiopyran-3-yl | —$(CH_2)_3$—O— | 3-F-phenyl |
| A.770 | $C_2H_5$ | Tetrahydropyran-3-yl | —$(CH_2)_3$—O— | 4-F-phenyl |
| A.771 | n-$C_3H_7$ | Tetrahydropyran-3-yl | —$(CH_2)_3$—O— | 4-F-phenyl |
| A.772 | $C_2H_5$ | Tetrahydropyran-4-yl | —$(CH_2)_3$—O— | 4-F-phenyl |
| A.773 | n-$C_3H_7$ | Tetrahydropyran-4-yl | —$(CH_2)_3$—O— | 4-F-phenyl |
| A.774 | $C_2H_5$ | Tetrahydrothiopyran-3-yl | —$(CH_2)_3$—O— | 4-F-phenyl |
| A.775 | n-$C_3H_7$ | Tetrahydrothiopyran-3-yl | —$(CH_2)_3$—O— | 4-F-phenyl |
| A.776 | $C_2H_5$ | Tetrahydropyran-3-yl | —$(CH_2)_3$—O— | 2-Cl-phenyl |
| A.777 | n-$C_3H_7$ | Tetrahydropyran-3-yl | —$(CH_2)_3$—O— | 2-Cl-phenyl |
| A.778 | $C_2H_5$ | Tetrahydropyran-4-yl | —$(CH_2)_3$—O— | 2-Cl-phenyl |
| A.779 | n-$C_3H_7$ | Tetrahydropyran-4-yl | —$(CH_2)_3$—O— | 2-Cl-phenyl |
| A.780 | $C''H_5$ | Tetrahydrothiopyran-3-yl | —$(CH_2)_3$—O— | 2-Cl-phenyl |
| A.781 | n-$C_3H_7$ | Tetrahydrothiopyran-3-yl | —$(CH_2)_3$—O— | 2-Cl-phenyl |
| A.782 | $C_2H_5$ | Tetrahydropyran-3-yl | —$(CH_2)_3$—O— | 3-Cl-phenyl |
| A.783 | n-$C_3H_7$ | Tetrahydropyran-3-yl | —$(CH_2)_3$—O— | 3-Cl-phenyl |
| A.784 | $C_2H_5$ | Tetrahydropyran-4-yl | —$(CH_2)_3$—O— | 3-Cl-phenyl |

TABLE 8-continued

The following cyclohexenone derivatives of the formula II are known from EP-A 456 112

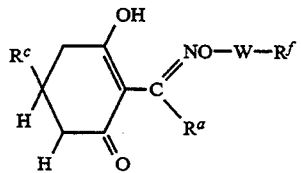

($R^b$, $R^d$, $R^e$ = H)

| No. | $R^a$ | $R^c$ | W | $R^f$ |
|---|---|---|---|---|
| A.785 | n-$C_3H_7$ | Tetrahydropyran-4-yl | —$(CH_2)_3$—O— | 3-Cl-phenyl |
| A.786 | $C_2H_5$ | Tetrahydrothiopyran-3-yl | —$(CH_2)_3$—O— | 3-Cl-phenyl |
| A.787 | n-$C_3H_7$ | Tetrahydrothiopyran-3-yl | —$(CH_2)_3$—O— | 3-Cl-phenyl |
| A.788 | $C_2H_5$ | Tetrahydropyran-3-yl | —$(CH_2)_3$—O— | 4-Cl-phenyl |
| A.789 | n-$C_3H_7$ | Tetrahydropyran-3-yl | —$(CH_2)_3$—O— | 4-Cl-phenyl |
| A.790 | $C_2H_5$ | Tetrahydropyran-4-yl | —$(CH_2)_3$—O— | 4-Cl-phenyl |
| A.791 | n-$C_3H_7$ | Tetrahydropyran-4-yl | —$(CH_2)_3$—O— | 4-Cl-phenyl |
| A.792 | $C_2H_5$ | Tetrahydrothiopyran-3-yl | —$(CH_2)_3$—O— | 4-Cl-phenyl |
| A.793 | n-$C_3H_7$ | Tetrahydrothiopyran-3-yl | —$(CH_2)_3$—O— | 4-Cl-phenyl |
| A.794 | $C_2H_5$ | Tetrahydropyran-3-yl | —$(CH_2)_3$—O— | 4-$NO_2$-phenyl |
| A.795 | n-$C_3H_7$ | Tetrahydropyran-3-yl | —$(CH_2)_3$—O— | 4-$NO_2$-phenyl |
| A.796 | $C_2H_5$ | Tetrahydropyran-4-yl | —$(CH_2)_3$—O— | 4-$NO_2$-phenyl |
| A.797 | n-$C_3H_7$ | Tetrahydropyran-4-yl | —$(CH_2)_3$—O— | 4-$NO_2$-phenyl |
| A.798 | $C_2H_5$ | Tetrahydrothiopyran-3-yl | —$(CH_2)_3$—O— | 4-$NO_2$-phenyl |
| A.799 | n-$C_3H_7$ | Tetrahydrothiopyran-3-yl | —$(CH_2)_3$—O— | 4-$NO_2$-phenyl |
| A.800 | $C''H_5$ | Tetrahydropyran-3-yl | —$(CH_2)_3$—O— | 4-Br-phenyl |
| A.801 | n-$C_3H_7$ | Tetrahydropyran-3-yl | —$(CH_2)_3$—O— | 4-Br-phenyl |
| A.802 | $C_2H_5$ | Tetrahydropyran-4-yl | —$(CH_2)_3$—O— | 4-Br-phenyl |
| A.803 | n-$C_3H_7$ | Tetrahydropyran-4-yl | —$(CH_2)_3$—O— | 4-Br-phenyl |
| A.804 | $C_2H_5$ | Tetrahydrothiopyran-4-yl | —$(CH_2)_3$—O— | 4-Br-phenyl |
| A.805 | n-$C_3H_7$ | Tetrahydrothiopyran-4-yl | —$(CH_2)_3$—O— | 4-Br-phenyl |
| A.806 | $C_2H_5$ | Tetrahydropyran-3-yl | —$(CH_2)_3$—S— | Phenyl |
| A.807 | n-$C_3H_7$ | Tetrahydropyran-3-yl | —$(CH_2)_3$—S— | Phenyl |
| A.808 | $C_2H_5$ | Tetrahydropyran-4-yl | —$(CH_2)_3$—S— | Phenyl |
| A.809 | n-$C_3H_7$ | Tetrahydropyran-4-yl | —$(CH_2)_3$—S— | Phenyl |
| A.810 | $C_2H_5$ | Tetrahydrothiopyran-3-yl | —$(CH_2)_3$—S— | Phenyl |
| A.811 | n-$C_3H_7$ | Tetrahydrothiopyran-3-yl | —$(CH_2)_3$—S— | Phenyl |
| A.812 | $C_2H_5$ | Tetrahydropyran-3-yl | —$(CH_2)_3$—S— | 4-F-phenyl |
| A.813 | n-$C_3H_7$ | Tetrahydropyran-3-yl | —$(CH_2)_3$—S— | 4-F-phenyl |
| A.814 | $C_2H_5$ | Tetrahydropyran-4-yl | —$(CH_2)_3$—S— | 4-F-phenyl |
| A.815 | n-$C_3H_7$ | Tetrahydropyran-4-yl | —$(CH_2)_3$—S— | 4-F-phenyl |
| A.816 | $C_2H_5$ | Tetrahydrothiopyran-3-yl | —$(CH_2)_3$—S— | 4-F-phenyl |
| A.817 | n-$C_3H_7$ | Tetrahydrothiopyran-3-yl | —$(CH_2)_3$—S— | 4-F-phenyl |
| A.818 | $C_2H_5$ | Tetrahydropyran-3-yl | —$(CH_2)_3$—S— | 4-Cl-phenyl |
| A.819 | n-$C_3H_7$ | Tetrahydropyran-3-yl | —$(CH_2)_3$—S— | 4-Cl-phenyl |
| A.820 | $C''H_5$ | Tetrahydropyran-4-yl | —$(CH_2)_3$—S— | 4-Cl-phenyl |
| A.821 | n-$C_3H_7$ | Tetrahydropyran-4-yl | —$(CH_2)_3$—S— | 4-Cl-phenyl |
| A.822 | $C_2H_5$ | Tetrahydrothiopyran-3-yl | —$(CH_2)_3$—S— | 4-Cl-phenyl |
| A.823 | n-$C_3H_7$ | Tetrahydrothiopyran-3-yl | —$(CH_2)_3$—S— | 4-Cl-phenyl |
| A.824 | $C_2H_5$ | Tetrahydropyran-3-yl | —$(CH_2)_3$—S— | 2-Cl-phenyl |
| A.825 | n-$C_3H_7$ | Tetrahydropyran-3-yl | —$(CH_2)_3$—S— | 2-Cl-phenyl |
| A.826 | $C_2H_5$ | Tetrahydropyran-4-yl | —$(CH_2)_3$—S— | 2-Cl-phenyl |
| A.827 | n-$C_3H_7$ | Tetrahydropyran-4-yl | —$(CH_2)_3$—S— | 2-Cl-phenyl |
| A.828 | $C_2H_5$ | Tetrahydrothiopyran-3-yl | —$(CH_2)_3$—S— | 2-Cl-phenyl |
| A.829 | n-$C_3H_7$ | Tetrahydrothiopyran-3-yl | —$(CH_2)_3$—S— | 2-Cl-phenyl |
| A.830 | $C_2H_5$ | Tetrahydropyran-3-yl | —$(CH_2)_3$—S— | 3-Cl-phenyl |
| A.831 | n-$C_3H_7$ | Tetrahydropyran-3-yl | —$(CH_2)_3$—S— | 3-Cl-phenyl |
| A.832 | $C_2H_5$ | Tetrahydropyran-4-yl | —$(CH_2)_3$—S— | 3-Cl-phenyl |
| A.833 | n-$C_3H_7$ | Tetrahydropyran-4-yl | —$(CH_2)_3$—S— | 3-Cl-phenyl |
| A.834 | $C_2H_5$ | Tetrahydrothiopyran-3-yl | —$(CH_2)_3$—S— | 3-Cl-phenyl |
| A.835 | n-$C_3H_7$ | Tetrahydrothiopyran-3-yl | —$(CH_2)_3$—S— | 3-Cl-phenyl |
| A.836 | $C_2H_5$ | Tetrahydropyran-3-yl | —$(CH_2)_3$—S— | 2,5-$Cl_2$-phenyl |
| A.837 | n-$C_3H_7$ | Tetrahydropyran-3-yl | —$(CH_2)_3$—S— | 2,5-$Cl_2$-phenyl |
| A.838 | $C_2H_5$ | Tetrahydropyran-4-yl | —$(CH_2)_3$—S— | 2,5-$Cl_2$-phenyl |
| A.839 | n-$C_3H_7$ | Tetrahydropyran-4-yl | —$(CH_2)_3$—S— | 2,5-$Cl_2$-phenyl |
| A.840 | $C_2H_5$ | Tetrahydrothiopyran-3-yl | —$(CH_2)_3$—S— | 2,5-$Cl_2$-phenyl |
| A.841 | n-$C_3H_7$ | Tetrahydrothiopyran-3-yl | —$(CH_2)_3$—S— | 2,5-$Cl_2$-phenyl |
| A.842 | $C_2H_5$ | Tetrahydropyran-3-yl | —$(CH_2)_3$—S— | 2,6-$Cl_2$-phenyl |
| A.843 | n-$C_3H_7$ | Tetrahydropyran-3-yl | —$(CH_2)_3$—S— | 2,6-$Cl_2$-phenyl |
| A.844 | $C_2H_5$ | Tetrahydropyran-4-yl | —$(CH_2)_3$—S— | 2,6-$Cl_2$-phenyl |
| A.845 | n-$C_3H_7$ | Tetrahydropyran-4-yl | —$(CH_2)_3$—S— | 2,6-$Cl_2$-phenyl |
| A.846 | $C_2H_5$ | Tetrahydrothiopyran-3-yl | —$(CH_2)_3$—S— | 2,6-$Cl_2$-phenyl |
| A.847 | n-$C_3H_7$ | Tetrahydrothiopyran-3-yl | —$(CH_2)_3$—S— | 2,6-$Cl_2$-phenyl |
| A.848 | $C_2H_5$ | Tetrahydropyran-3-yl | —$CH_2CH_2OCH_2$— | Phenyl |
| A.849 | n-$C_3H_7$ | Tetrahydropyran-3-yl | —$CH_2CH_2OCH_2$— | Phenyl |
| A.850 | $C_2H_5$ | Tetrahydropyran-4-yl | —$CH_2CH_2OCH_2$— | Phenyl |
| A.851 | n-$C_3H_7$ | Tetrahydropyran-4-yl | —$CH_2CH_2OCH_2$— | Phenyl |
| A.852 | $C_2H_5$ | Tetrahydrothiopyran-3-yl | —$CH_2CH_2OCH_2$— | Phenyl |

TABLE 8-continued

The following cyclohexenone derivatives of the formula II are known from EP-A 456 112

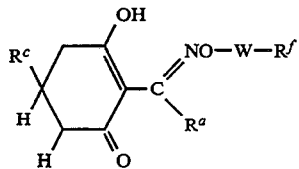

($R^b$, $R^d$, $R^e$ = H)

| No. | $R^a$ | $R^c$ | W | $R^f$ |
|---|---|---|---|---|
| A.853 | n-$C_3H_7$ | Tetrahydrothiopyran-3-yl | —$CH_2CH_2OCH_2$— | Phenyl |
| A.854 | $C_2H_5$ | Tetrahydropyran-3-yl | —$CH_2CH_2OCH_2$— | 2-F-phenyl |
| A.855 | n-$C_3H_7$ | Tetrahydropyran-3-yl | —$CH_2CH_2OCH_2$— | 2-F-phenyl |
| A.856 | $C_2H_5$ | Tetrahydropyran-4-yl | —$CH_2CH_2OCH_2$— | 2-F-phenyl |
| A.857 | n-$C_3H_7$ | Tetrahydropyran-4-yl | —$CH_2CH_2OCH_2$— | 2-F-phenyl |
| A.858 | $C_2H_5$ | Tetrahydrothiopyran-3-yl | —$CH_2CH_2OCH_2$— | 2-F-phenyl |
| A.859 | n-$C_3H_7$ | Tetrahydrothiopyran-3-yl | —$CH_2CH_2OCH_2$— | 2-F-phenyl |
| A.860 | $C''H_5$ | Tetrahydropyran-3-yl | —$CH_2CH_2OCH_2$— | 3-F-phenyl |
| A.861 | n-$C_3H_7$ | Tetrahydropyran-3-yl | —$CH_2CH_2OCH_2$— | 3-F-phenyl |
| A.862 | $C_2H_5$ | Tetrahydropyran-4-yl | —$CH_2CH_2OCH_2$— | 3-F-phenyl |
| A.863 | n-$C_3H_7$ | Tetrahydropyran-4-yl | —$CH_2CH_2OCH_2$— | 3-F-phenyl |
| A.864 | $C_2H_5$ | Tetrahydrothiopyran-3-yl | —$CH_2CH_2OCH_2$— | 3-F-phenyl |
| A.865 | n-$C_3H_7$ | Tetrahydrothiopyran-3-yl | —$CH_2CH_2OCH_2$— | 3-F-phenyl |
| A.866 | $C_2H_5$ | Tetrahydropyran-3-yl | —$CH_2CH_2OCH_2$— | 4-F-phenyl |
| A.867 | n-$C_3H_7$ | Tetrahydropyran-3-yl | —$CH_2CH_2OCH_2$— | 4-F-phenyl |
| A.868 | $C_2H_5$ | Tetrahydropyran-4-yl | —$CH_2CH_2OCH_2$— | 4-F-phenyl |
| A.869 | n-$C_3H_7$ | Tetrahydropyran-4-yl | —$CH_2CH_2OCH_2$— | 4-F-phenyl |
| A.870 | $C_2H_5$ | Tetrahydrothiopyran-3-yl | —$CH_2CH_2OCH_2$— | 4-F-phenyl |
| A.871 | n-$C_3H_7$ | Tetrahydrothiopyran-3-yl | —$CH_2CH_2OCH_2$— | 4-F-phenyl |
| A.872 | $C_2H_5$ | Tetrahydropyran-3-yl | —$CH_2CH_2OCH_2$— | 2-Cl-phenyl |
| A.873 | n-$C_3H_7$ | Tetrahydropyran-3-yl | —$CH_2CH_2OCH_2$— | 2-Cl-phenyl |
| A.874 | $C_2H_5$ | Tetrahydropyran-4-yl | —$CH_2CH_2OCH_2$— | 2-Cl-phenyl |
| A.875 | n-$C_3H_7$ | Tetrahydropyran-4-yl | —$CH_2CH_2OCH_2$— | 2-Cl-phenyl |
| A.876 | $C_2H_5$ | Tetrahydrothiopyran-3-yl | —$CH_2CH_2OCH_2$— | 2-Cl-phenyl |
| A.877 | n-$C_3H_7$ | Tetrahydrothiopyran-3-yl | —$CH_2CH_2OCH_2$— | 2-Cl-phenyl |
| A.878 | $C_2H_5$ | Tetrahydropyran-3-yl | —$CH_2CH_2OCH_2$— | 3-Cl-phenyl |
| A.879 | n-$C_3H_7$ | Tetrahydropyran-3-yl | —$CH_2CH_2OCH_2$— | 3-Cl-phenyl |
| A.880 | $C''H_5$ | Tetrahydropyran-4-yl | —$CH_2CH_2OCH_2$— | 3-Cl-phenyl |
| A.881 | n-$C_3H_7$ | Tetrahydropyran-4-yl | —$CH_2CH_2OCH_2$— | 3-Cl-phenyl |
| A.882 | $C_2H_5$ | Tetrahydrothiopyran-3-yl | —$CH_2CH_2OCH_2$— | 3-Cl-phenyl |
| A.883 | n-$C_3H_7$ | Tetrahydrothiopyran-3-yl | —$CH_2CH_2OCH_2$— | 3-Cl-phenyl |
| A.884 | $C_2H_5$ | Tetrahydropyran-3-yl | —$CH_2CH_2OCH_2$— | 4-Cl-phenyl |
| A.885 | n-$C_3H_7$ | Tetrahydropyran-3-yl | —$CH_2CH_2OCH_2$— | 4-Cl-phenyl |
| A.886 | $C_2H_5$ | Tetrahydropyran-4-yl | —$CH_2CH_2OCH_2$— | 4-Cl-phenyl |
| A.887 | n-$C_3H_7$ | Tetrahydropyran-4-yl | —$CH_2CH_2OCH_2$— | 4-Cl-phenyl |
| A.888 | $C_2H_5$ | Tetrahydrothiopyran-3-yl | —$CH_2CH_2OCH_2$— | 4-Cl-phenyl |
| A.889 | n-$C_3H_7$ | Tetrahydrothiopyran-3-yl | —$CH_2CH_2OCH_2$— | 4-Cl-phenyl |
| A.890 | $C_2H_5$ | Tetrahydropyran-3-yl | —$CH_2CH_2OCH_2$— | 2-$CH_3$ |
| A.891 | n-$C_3H_7$ | Tetrahydropyran-3-yl | —$CH_2CH_2OCH_2$— | 2-$CH_3$ |
| A.892 | $C_2H_5$ | Tetrahydropyran-4-yl | —$CH_2CH_2OCH_2$— | 2-$CH_3$ |
| A.893 | n-$C_3H_7$ | Tetrahydropyran-4-yl | —$CH_2CH_2OCH_2$— | 2-$CH_3$ |
| A.894 | $C_2H_5$ | Tetrahydrothiopyran-3-yl | —$CH_2CH_2OCH_2$— | 2-$CH_3$ |
| A.895 | n-$C_3H_7$ | Tetrahydrothiopyran-3-yl | —$CH_2CH_2OCH_2$— | 2-$CH_3$ |
| A.896 | $C_2H_5$ | Tetrahydropyran-3-yl | —$CH_2CH_2OCH_2$— | 3-$CH_3$ |
| A.897 | n-$C_3H_7$ | Tetrahydropyran-3-yl | —$CH_2CH_2OCH_2$— | 3-$CH_3$ |
| A.898 | $C_2H_5$ | Tetrahydropyran-4-yl | —$CH_2CH_2OCH_2$— | 3-$CH_3$ |
| A.899 | n-$C_3H_7$ | Tetrahydropyran-4-yl | —$CH_2CH_2OCH_2$— | 3-$CH_3$ |
| A.900 | $C''H_5$ | Tetrahydrothiopyran-3-yl | —$CH_2CH_2OCH_2$— | 3-$CH_3$ |
| A.901 | n-$C_3H_7$ | Tetrahydrothiopyran-3-yl | —$CH_2CH_2OCH_2$— | 3-$CH_3$ |
| A.902 | $C_2H_5$ | Tetrahydropyran-3-yl | —$CH_2CH_2OCH_2$— | 4-$CH_3$ |
| A.903 | n-$C_3H_7$ | Tetrahydropyran-3-yl | —$CH_2CH_2OCH_2$— | 4-$CH_3$ |
| A.904 | $C_2H_5$ | Tetrahydropyran-4-yl | —$CH_2CH_2OCH_2$— | 4-$CH_3$ |
| A.905 | n-$C_3H_7$ | Tetrahydropyran-4-yl | —$CH_2CH_2OCH_2$— | 4-$CH_3$ |
| A.906 | $C_2H_5$ | Tetrahydrothiopyran-3-yl | —$CH_2CH_2OCH_2$— | 4-$CH_3$ |
| A.907 | n-$C_3H_7$ | Tetrahydrothiopyran-3-yl | —$CH_2CH_2OCH_2$— | 4-$CH_3$ |
| A.908 | $C_2H_5$ | Tetrahydropyran-3-yl | —$CH_2CH_2OCH_2$— | 4-tert.-$C_4H_9$ |
| A.909 | n-$C_3H_7$ | Tetrahydropyran-3-yl | —$CH_2CH_2OCH_2$— | 4-tert.-$C_4H_9$ |
| A.910 | $C_2H_5$ | Tetrahydropyran-4-yl | —$CH_2CH_2OCH_2$— | 4-tert.-$C_4H_9$ |
| A.911 | n-$C_3H_7$ | Tetrahydropyran-4-yl | —$CH_2CH_2OCH_2$— | 4-tert.-$C_4H_9$ |
| A.912 | $C_2H_5$ | Tetrahydrothiopyran-3-yl | —$CH_2CH_2OCH_2$— | 4-tert.-$C_4H_9$ |
| A.913 | n-$C_3H_7$ | Tetrahydrothiopyran-3-yl | —$CH_2CH_2OCH_2$— | 4-tert.-$C_4H_9$ |
| A.914 | $C_2H_5$ | Tetrahydropyran-3-yl | —$CH_2CH_2SCH_2$— | Phenyl |
| A.915 | n-$C_3H_7$ | Tetrahydropyran-3-yl | —$CH_2CH_2SCH_2$— | Phenyl |
| A.916 | $C_2H_5$ | Tetrahydropyran-4-yl | —$CH_2CH_2SCH_2$— | Phenyl |
| A.917 | n-$C_3H_7$ | Tetrahydropyran-4-yl | —$CH_2CH_2SCH_2$— | Phenyl |
| A.918 | $C_2H_5$ | Tetrahydrothiopyran-3-yl | —$CH_2CH_2SCH_2$— | Phenyl |
| A.919 | n-$C_3H_7$ | Tetrahydrothiopyran-3-yl | —$CH_2CH_2SCH_2$— | Phenyl |
| A.920 | $C''H_5$ | Tetrahydropyran-3-yl | —$CH_2CH_2SCH_2$— | 4-F-phenyl |

TABLE 8-continued

The following cyclohexenone derivatives of the formula II are known from EP-A 456 112

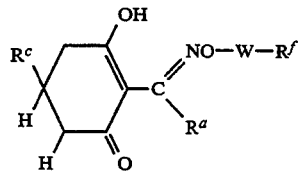

($R^b$, $R^d$, $R^e$ = H)

| No. | $R^a$ | $R^c$ | W | $R^f$ |
|---|---|---|---|---|
| A.921 | n-$C_3H_7$ | Tetrahydropyran-3-yl | —$CH_2CH_2SCH_2$— | 4-F-phenyl |
| A.922 | $C_2H_5$ | Tetrahydropyran-4-yl | —$CH_2CH_2SCH_2$— | 4-F-phenyl |
| A.923 | n-$C_3H_7$ | Tetrahydropyran-4-yl | —$CH_2CH_2SCH_2$— | 4-F-phenyl |
| A.924 | $C_2H_5$ | Tetrahydrothiopyran-3-yl | —$CH_2CH_2SCH_2$— | 4-F-phenyl |
| A.925 | n-$C_3H_7$ | Tetrahydrothiopyran-3-yl | —$CH_2CH_2SCH_2$— | 4-F-phenyl |
| A.926 | $C_2H_5$ | Tetrahydropyran-3-yl | —$CH_2CH_2SCH_2$— | 4-Cl-phenyl |
| A.927 | n-$C_3H_7$ | Tetrahydropyran-3-yl | —$CH_2CH_2SCH_2$— | 4-Cl-phenyl |
| A.928 | $C_2H_5$ | Tetrahydropyran-4-yl | —$CH_2CH_2SCH_2$— | 4-Cl-phenyl |
| A.929 | n-$C_3H_7$ | Tetrahydropyran-4-yl | —$CH_2CH_2SCH_2$— | 4-Cl-phenyl |
| A.930 | $C_2H_5$ | Tetrahydrothiopyran-3-yl | —$CH_2CH_2SCH_2$— | 4-Cl-phenyl |
| A.931 | n-$C_3H_7$ | Tetrahydrothiopyran-3-yl | —$CH_2CH_2SCH_2$— | 4-Cl-phenyl |
| A.932 | $C_2H_5$ | Tetrahydropyran-3-yl | —$(CH_2)_4$—O— | Phenyl |
| A.933 | n-$C_3H_7$ | Tetrahydropyran-3-yl | —$(CH_2)_4$—O— | Phenyl |
| A.934 | $C_2H_5$ | Tetrahydropyran-4-yl | —$(CH_2)_4$—O— | Phenyl |
| A.935 | n-$C_3H_7$ | Tetrahydropyran-4-yl | —$(CH_2)_4$—O— | Phenyl |
| A.936 | $C_2H_5$ | Tetrahydrothiopyran-3-yl | —$(CH_2)_4$—O— | Phenyl |
| A.937 | n-$C_3H_7$ | Tetrahydrothiopyran-3-yl | —$(CH_2)_4$—O— | Phenyl |
| A.938 | $C_2H_5$ | Tetrahydropyran-3-yl | —$(CH_2)_4$—O— | 2-F-phenyl |
| A.939 | n-$C_3H_7$ | Tetrahydropyran-3-yl | —$(CH_2)_4$—O— | 2-F-phenyl |
| A.940 | $C_2H_5$ | Tetrahydropyran-4-yl | —$(CH_2)_4$—O— | 2-F-phenyl |
| A.941 | n-$C_3H_7$ | Tetrahydropyran-4-yl | —$(CH_2)_4$—O— | 2-F-phenyl |
| A.942 | $C_2H_5$ | Tetrahydrothiopyran-3-yl | —$(CH_2)_4$—O— | 2-F-phenyl |
| A.943 | n-$C_3H_7$ | Tetrahydrothiopyran-3-yl | —$(CH_2)_4$—O— | 2-F-phenyl |
| A.944 | $C_2H_5$ | Tetrahydropyran-3-yl | —$(CH_2)_4$—O— | 3-F-phenyl |
| A.945 | n-$C_3H_7$ | Tetrahydropyran-3-yl | —$(CH_2)_4$—O— | 3-F-phenyl |
| A.946 | $C_2H_5$ | Tetrahydropyran-4-yl | —$(CH_2)_4$—O— | 3-F-phenyl |
| A.947 | n-$C_3H_7$ | Tetrahydropyran-4-yl | —$(CH_2)_4$—O— | 3-F-phenyl |
| A.948 | $C_2H_5$ | Tetrahydrothiopyran-3-yl | —$(CH_2)_4$—O— | 3-F-phenyl |
| A.949 | n-$C_3H_7$ | Tetrahydrothiopyran-3-yl | —$(CH_2)_4$—O— | 3-F-phenyl |
| A.950 | $C_2H_5$ | Tetrahydropyran-3-yl | —$(CH_2)_4$—O— | 4-F-phenyl |
| A.951 | n-$C_3H_7$ | Tetrahydropyran-3-yl | —$(CH_2)_4$—O— | 4-F-phenyl |
| A.952 | $C_2H_5$ | Tetrahydropyran-4-yl | —$(CH_2)_4$—O— | 4-F-phenyl |
| A.953 | n-$C_3H_7$ | Tetrahydropyran-4-yl | —$(CH_2)_4$—O— | 4-F-phenyl |
| A.954 | $C_2H_5$ | Tetrahydrothiopyran-3-yl | —$(CH_2)_4$—O— | 4-F-phenyl |
| A.955 | n-$C_3H_7$ | Tetrahydrothiopyran-3-yl | —$(CH_2)_4$—O— | 4-F-phenyl |
| A.956 | $C_2H_5$ | Tetrahydropyran-3-yl | —$(CH_2)_4$—O— | 4-Cl-phenyl |
| A.957 | n-$C_3H_7$ | Tetrahydropyran-3-yl | —$(CH_2)_4$—O— | 4-Cl-phenyl |
| A.958 | $C_2H_5$ | Tetrahydropyran-4-yl | —$(CH_2)_4$—O— | 4-Cl-phenyl |
| A.959 | n-$C_3H_7$ | Tetrahydropyran-4-yl | —$(CH_2)_4$—O— | 4-Cl-phenyl |
| A.960 | $C''H_5$ | Tetrahydrothiopyran-3-yl | —$(CH_2)_4$—O— | 4-Cl-phenyl |
| A.961 | n-$C_3H_7$ | Tetrahydrothiopyran-3-yl | —$(CH_2)_4$—O— | 4-Cl-phenyl |
| A.962 | $C_2H_5$ | Tetrahydropyran-3-yl | —$(CH_2)_4$—O— | 2,6-$Cl_2$-phenyl |
| A.963 | n-$C_3H_7$ | Tetrahydropyran-3-yl | —$(CH_2)_4$—O— | 2,6-$Cl_2$-phenyl |
| A.964 | $C_2H_5$ | Tetrahydropyran-4-yl | —$(CH_2)_4$—O— | 2,6-$Cl_2$-phenyl |
| A.965 | n-$C_3H_7$ | Tetrahydropyran-4-yl | —$(CH_2)_4$—O— | 2,6-$Cl_2$-phenyl |
| A.966 | $C_2H_5$ | Tetrahydrothiopyran-3-yl | —$(CH_2)_4$—O— | 2,6-$Cl_2$-phenyl |
| A.967 | n-$C_3H_7$ | Tetrahydrothiopyran-3-yl | —$(CH_2)_4$—O— | 2,6-$Cl_2$-phenyl |
| A.968 | $C_2H_5$ | Tetrahydropyran-3-yl | —$CH_2CH_2OCH_2CH_2$— | Phenyl |
| A.969 | n-$C_3H_7$ | Tetrahydropyran-3-yl | —$CH_2CH_2OCH_2CH_2$— | Phenyl |
| A.970 | $C_2H_5$ | Tetrahydropyran-4-yl | —$CH_2CH_2OCH_2CH_2$— | Phenyl |
| A.971 | n-$C_3H_7$ | Tetrahydropyran-4-yl | —$CH_2CH_2OCH_2CH_2$— | Phenyl |
| A.972 | $C_2H_5$ | Tetrahydrothiopyran-3-yl | —$CH_2CH_2OCH_2CH_2$— | Phenyl |
| A.973 | n-$C_3H_7$ | Tetrahydrothiopyran-3-yl | —$CH_2CH_2OCH_2CH_2$— | Phenyl |
| A.974 | $C_2H_5$ | Tetrahydropyran-3-yl | —$CH_2CH_2OCH_2CH_2$— | 4-F-phenyl |
| A.975 | n-$C_3H_7$ | Tetrahydropyran-3-yl | —$CH_2CH_2OCH_2CH_2$— | 4-F-phenyl |
| A.976 | $C_2H_5$ | Tetrahydropyran-4-yl | —$CH_2CH_2OCH_2CH_2$— | 4-F-phenyl |
| A.977 | n-$C_3H_7$ | Tetrahydropyran-4-yl | —$CH_2CH_2OCH_2CH_2$— | 4-F-phenyl |
| A.978 | $C_2H_5$ | Tetrahydrothiopyran-3-yl | —$CH_2CH_2OCH_2CH_2$— | 4-F-phenyl |
| A.979 | n-$C_3H_7$ | Tetrahydrothiopyran-3-yl | —$CH_2CH_2OCH_2CH_2$— | 4-F-phenyl |
| A.980 | $C_2H_5$ | Tetrahydropyran-3-yl | —$CH_2CH_2OCH_2CH_2$— | 4-Cl-phenyl |
| A.981 | n-$C_3H_7$ | Tetrahydropyran-3-yl | —$CH_2CH_2OCH_2CH_2$— | 4-Cl-phenyl |
| A.982 | $C_2H_5$ | Tetrahydropyran-4-yl | —$CH_2CH_2OCH_2CH_2$— | 4-Cl-phenyl |
| A.983 | n-$C_3H_7$ | Tetrahydropyran-4-yl | —$CH_2CH_2OCH_2CH_2$— | 4-Cl-phenyl |
| A.984 | $C_2H_5$ | Tetrahydrothiopyran-3-yl | —$CH_2CH_2OCH_2CH_2$— | 4-Cl-phenyl |
| A.985 | n-$C_3H_7$ | Tetrahydrothiopyran-3-yl | —$CH_2CH_2OCH_2CH_2$— | 4-Cl-phenyl |
| A.986 | $C_2H_5$ | Tetrahydropyran-3-yl | —$(CH_2)_5$—O— | Phenyl |
| A.987 | n-$C_3H_7$ | Tetrahydropyran-3-yl | —$(CH_2)_5$—O— | Phenyl |
| A.988 | $C_2H_5$ | Tetrahydropyran-4-yl | —$(CH_2)_5$—O— | Phenyl |

TABLE 8-continued

The following cyclohexenone derivatives of the formula II are known from EP-A 456 112

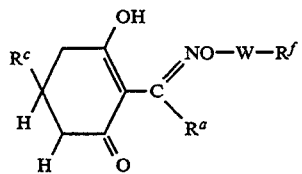

($R^b$, $R^d$, $R^e$ = H)

| No. | $R^a$ | $R^c$ | W | $R^f$ |
|---|---|---|---|---|
| A.989 | n-$C_3H_7$ | Tetrahydropyran-4-yl | —($CH_2$)$_5$—O— | Phenyl |
| A.990 | $C_2H_5$ | Tetrahydrothiopyran-3-yl | —($CH_2$)$_5$—O— | Phenyl |
| A.991 | n-$C_3H_7$ | Tetrahydrothiopyran-3-yl | —($CH_2$)$_5$—O— | Phenyl |
| A.992 | $C_2H_5$ | Tetrahydropyran-3-yl | —($CH_2$)$_5$—O— | 4-F-phenyl |
| A.993 | n-$C_3H_7$ | Tetrahydropyran-3-yl | —($CH_2$)$_5$—O— | 4-F-phenyl |
| A.994 | $C_2H_5$ | Tetrahydropyran-4-yl | —($CH_2$)$_5$—O— | 4-F-phenyl |
| A.995 | n-$C_3H_7$ | Tetrahydropyran-4-yl | —($CH_2$)$_5$—O— | 4-F-phenyl |
| A.996 | $C_2H_5$ | Tetrahydrothiopyran-3-yl | —($CH_2$)$_5$—O— | 4-F-phenyl |
| A.997 | n-$C_3H_7$ | Tetrahydrothiopyran-3-yl | —($CH_2$)$_5$—O— | 4-F-phenyl |
| A.998 | $C_2H_5$ | Tetrahydropyran-3-yl | —($CH_2$)$_5$—O— | 4-Cl-phenyl |
| A.999 | n-$C_3H_7$ | Tetrahydropyran-3-yl | —($CH_2$)$_5$—O— | 4-Cl-phenyl |
| A.1000 | $C_2H_5$ | Tetrahydropyran-4-yl | —($CH_2$)$_5$—O— | 4-Cl-phenyl |
| A.1001 | n-$C_3H_7$ | Tetrahydropyran-4-yl | —($CH_2$)$_5$—O— | 4-Cl-phenyl |
| A.1002 | $C_2H_5$ | Tetrahydrothiopyran-3-yl | —($CH_2$)$_5$—O— | 4-Cl-phenyl |
| A.1003 | n-$C_3H_7$ | Tetrahydrothiopyran-3-yl | —($CH_2$)$_5$—O— | 4-Cl-phenyl |

TABLE 9

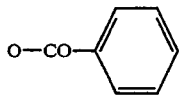

II

| No. | $R^a$ | $R^b$ | $R^c$ | $R^d$ | $R^e$ | W | $R^f$ | Lit. |
|---|---|---|---|---|---|---|---|---|
| A.1004 | n-$C_3H_7$ | Na | Methyl | $CH_3$ | $COOCH_3$ | —$CH_2CH$=$CH$— | H | DE-A 2 439 104 |
| A.1005 | n-$C_3H_7$ | H | Methyl | $CH_3$ | $C(CH_3)$=$NOCH_3$ | —$CH_2CH_2$— | H | EP-A 172 551 |
| A.1006 | n-$C_3H_7$ | Na | Tetrahydro-thiopyran-3-yl | H | H | —$CH_2CH$=$CH$— | 4-F-phenyl | EP-A 456 069 |
| A.1007 | $C_2H_5$ | Na | Tetrahydro-thiopyran-3-yl | H | H | —$CH_2CH$=$CH$— | 4-F-phenyl | EP-A 456 069 |
| A.1008 | n-$C_3H_7$ | 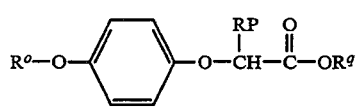 | Tetrahydro-thiopyran-3-yl | H | H | —$CH_2CH$=$CH$— | 4-F-phenyl | EP-A 456 069 |
| A.1009 | $C_2H_5$ | 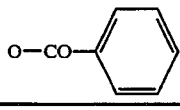 | Tetrahydro-thiopyran-3-yl | H | H | —$CH_2CH$=$CH$— | 4-F-phenyl | EP-A 456 069 |

Herbicidal active ingredients from the group of 2-(4-hetaryloxy)- or 2-(4-aryloxy)-phenoxycarboxylic acid derivatives of the formula III $$R^o-O-\underset{}{\bigcirc}-O-\underset{R^p}{\underset{|}{CH}}-\underset{}{\overset{O}{\underset{\|}{C}}}-OR^q$$

III where the substituents have the following meanings:
$R^o$ phenyl, pyridyl, benzoxazyl, benzothiazyl or benzopyrazinyl, where these aromatic ring systems may bear one to two radicals selected from the group consisting of: nitro, halogen such as fluorine, chlorine, bromine and iodine, especially fluorine and chlorine, branched or straight-chain $C_1$-$C_4$-alkyl such as methyl, ethyl, n-propyl, isopropyl, n-butyl and tert.-butyl, partially or completely halogenated $C_1$-$C_4$-alkyl, especially $C_1$-$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2difluoroethyl, 2,2-dichloro-2-fluoroethyl, 2,2,2-trichloroethyl and pentafluoroethyl, preferably trifluoromethyl, partially or completely halogenated $C_1$-$C_4$-alkoxy, especially $C_1$-$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably trifluoromethoxy;

$R^p$ hydrogen or methyl, preferably methyl, $R^q$ hydrogen, branched or straight-chain $C_1$-$C_4$-alkyl as mentioned above, especially methyl, ethyl, n-propyl and n-butyl, $C_3$-$C_4$-alkenyl such as prop-2-en-1-yl, but-2-en-1-yl, but-3-en-1-yl, 1-methyl-prop-2-en-1-yl, 2-methyl-prop-2-en-1-yl, especially prop-2-en-1-yl, $C_3$-$C_4$-alkynyl such as prop-2-yn-1-yl, but-2-yn-1-yl, but-3-yn-1-yl, 1-methyl-prop-2-yn-1-yl, 2-methyl-prop-2-yn-1-yl, preferably prop-2-yn-1-yl, $C_1$-$C_4$-alkoxy-$C_1$-$C_4$-alkyl such as methoxymethyl, ethoxymethyl, n-propoxymethyl, (1-methylethoxy) methyl, n-butoxymethyl, (1-methylpropoxy)methyl, (2-methylpropoxy)methyl, (1,1-dimethylethoxy) methyl, methoxyethyl, ethoxyethyl, n-propoxyethyl, (1-methylethoxy) ethyl, n-butoxyethyl, (1-methylpropoxy) ethyl, (2-methylpropoxy) ethyl, (1,1-dimethylethoxy) ethyl, 3-(methoxy)propyl, 2-(methoxy)propyl and 2-(ethoxy)propyl, preferably methoxymethyl and ethoxyethyl, $C_3$-$C_4$-alkylideniminooxy-$C_2$-$C_3$-alkyl, especially 2-propylideniminooxy-ethyl, tetrahydrofuranylmethyl, isoxazolidine or the equivalent or an agriculturally useful cation, for example an alkali metal cation such as sodium or potassium, one equivalent of an alkaline earth metal cation such as calcium, magnesium and barium, manganese, copper, zinc or iron cations, ammonium cations with—if desired—up to three substituents selected from the group consisting of $C_1$-$C_4$-alkyl radicals, hydroxy-$C_1$-$C_4$-alkyl radicals, phenyl or benzyl, such as tetraalkyl- and benzyltrialkylammonium cations, phosphonium cations, sulfonium cations such as trialkylsulfonium cations or sulfoxonium cations, are known from the literature (cf., for example, DE-A 22 23 894, DE-A 24 33 067 DE-A 25 76 251, DE-A 30 04 770, DE-A 32 46 847, BE-A 868 875, BE-A 858 618, EP-A 054 715, EP-A 248 968, EP-A 323 127 and U.S. Pat. No. 4,753,673).

The 2-(4-hetaryloxy)- and 2-(4-aryloxy-phenoxycarboxylic acid derivatives III may contain one or several centers of asymmetry. They are effective as racemates, as they are obtained in most methods of manufacture, but may if desired be prepared as pure isomers, or separated, by conventional methods.

Both the racemates and the pure isomers control unwanted plants from the Gramineae family. The tolerance by crop plants of these substances varies from commercially acceptable to unacceptable, depending on the substituents and application rate.

Specific examples of herbicidal 2-(4-hetaryloxy)- and 2-(4-aryloxy)-phenoxycarboxylic acid derivatives of the formula III whose crop plant tolerance can be improved by substituted thiochromenones I are listed in Table 10 below:

TABLE 10

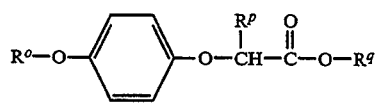

| No. | $R^o$ | $R^p$ | $R^q$ | Literature |
|---|---|---|---|---|
| B.01 |  | CH$_3$ | —CH$_3$ | DE-A 22 23 894 |
| B.02 |  | CH$_3$ | —n-C$_4$H$_9$ | BE-A 868 875 |
| B.03 |  | CH$_3$ | —CH$_2$CH$_2$OCH$_2$H$_5$ | US-A 4 753 673 |
| B.04 |  | CH$_3$ | —C$_2$H$_5$ | BE-A 858 618 |
| B.05 |  | CH$_3$ | —CH$_3$ | BE-A 868 875 |

TABLE 10-continued

Structure III:

R$^o$—O—(phenyl)—O—CH(R$^p$)—C(=O)—O—R$^q$

| No. | R$^o$ | R$^p$ | R$^q$ | Literature |
|---|---|---|---|---|
| B.06 | 4-F, 2-Cl pyridinyl | CH$_3$ | —CH$_2$—C≡CH | EP-A 248 968 |
| B.07 | 3,5-dichloropyridin-2-yl | CH$_3$ | N-pyrrolidinyloxy | DE-A 32 46 847 |
| B.08 | 6-chloroquinoxalin-2-yl | CH$_3$ | —C$_2$H$_5$ | DE-A 30 04 770 |
| B.09 | 6-chloroquinoxalin-2-yl | CH$_3$ | —CH$_2$CH$_2$—ON=C(CH$_3$)$_2$ | EP 54 715 |
| B.10 | 6-chloroquinoxalin-2-yl | CH$_3$ | —CH$_2$—(tetrahydrofuran-2-yl) | EP-A 323 727 |

Herbicidal active ingredients and safeners may be applied together or separately to the leaves and shoots of the crop plants and unwanted plants. It is, however, preferred to ply the herbicidal active ingredients and safeners simultaneously. If the herbicidal active ingredient and safener are applied separately, the safener is preferably applied first.

The safener and the herbicidal active ingredient may be formulated together or separately as suspensions, emulsions or solutions, and used as such to prepare spray liquors.

Safening effects are also achieved by treating the seeds of the crop plants or the seedlings with the safener prior to sowing or transplantation. The herbicidal active ingredient is then applied alone in conventional manner.

When the active ingredients are used for treating seed, amounts of from 0.1 to 10, and preferably from 1 to 2, g per kg of seed are generally required.

When the safener is used in seed swelling or for treating seedlings, solutions are preferably used which contain the safener in concentrations of from 1 to 10,000, and especially from 100 to 10,000, ppm.

Usually, the amount of safener I and herbicidal compound I or II varies from crop to crop; the ratios can vary over a wide range. They depend on the structure of the cyclohexenone derivatives II or the hetaryloxy- and aryloxyphenoxyacetic acid derivatives III, of the substituted thiochromenones I and the crop in which the compounds are applied. Suitable ratios of herbicidal active ingredient to safener-active thiochromenone I are from 1:10 to 1:0.01, preferably from 1:4 to 1:0.1.

The agents according to the invention, or the herbicidal active ingredients and safener if applied separately, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone and preferably water are suitable.

Aqueous formulations may be prepared from emulsion concentrates, pastes, oil dispersions, wettable powders or water-dispersible granules by adding water. To prepare emulsions, pastes and oil dispersions the ingredients and/or safeners as such or dissolved in an oil or solvent may be homogenized in water by means of wetting or dispersing agents, adherents or emulsifiers.

Concentrates which are suitable for dilution with water may be prepared from active ingredient and/or safener, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients and/or safener with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate; and ureas, and vegetable products such as grain meals, bark meal, wood meal, and nutshell meal, cellulosic powders, etc.

The formulations contain from 0.02 to 95, and preferably 0.5 to 90, % by weight of active ingredient and safener.

The herbicidal agents may contain, in addition to the antagonistically effective thiochromenones I and the herbicide from the group of cyclohexenones II or the (hetaryloxy)- or aryloxyphenoxycarboxylic acids III, further herbicidal or growth-regulating active ingredients of different chemical structure without the antagonistic effect of the substituted thiochromenones I being affected.

Manufacturing Examples (thiochromenones substituted according to the invention)

Example 1

2-Methylthiochromen-4(1H)-one

At 80° C., 100 g of polyphosphoric acid was placed in a receiver and over a period of 30 minutes a mixture of 11 g (100 mmol) of thiophenol and 13 g (100 mmol) of ethyl acetate was dripped in. This mixture is stirred for 15 minutes, and then poured onto 200 g of ice and subjected to suction filtration; yield: 17.0 g (97 %) of colorless crystals of m.p. 70° C.; active ingredient example 1.1.

The following compounds were prepared analogously:

TABLE A.1

| No. | Comp. I $R^1$ | $R^2$ | $R^3$ | m.p. [°C.] |
|---|---|---|---|---|
| 1.1 | Me | H | H | 70 |
| 1.2 | Me | H | 8-Cl | 95 |
| 1.3 | Me | H | 8-$CO_2H$ | 74 |
| 1.4 | Me | H | 6-$CMe_3$ | oil |
| 1.5 | Me | H | 6-Cl | 118 |
| 1.6 | Me | Me | 8-Cl | 123 |
| 1.7 | Me | Me | 8-$CO_2H$ | >250 |
| 1.8 | Me | Me | H | 103 |
| 1.9 | Me | Me | 6-Cl | 116 |
| 1.10 | Me | Me | 6-$CMe_3$ | oil |
| 1.11 | Me | Et | H | 57 |
| 1.12 | Me | Et | 8-Cl | 87 |
| 1.13 | Me | Et | 8-$CO_2H$ | 195 |
| 1.14 | Me | Et | 6-Cl | 132 |
| 1.15 | Me | Et | 6-$CMe_3$ | oil |
| 1.16 | Ph | H | H | oil |

Example 2

6-Chloro-4(1H)-oxo-thiochromene-2-carboxylic acid 2.9 g (50 mmol) of 4-chlorophenylmercaptofumaric acid is added to 50 ml of concentrated sulfuric acid in such a way that the internal temperature does not exceed 35° C. After 30 minutes at room temperature the mixture is poured onto ice and subjected to suction filtration; yield: 6.7 g (56%) of a colorless solid of m.p. 140°–145° C., active ingredient example 2.3.

The starting material may be prepared for example as follows:

4-Chlorophenylmercaptofumaric acid

At room temperature, a solution of 16.8 g (0.3 mol) of potassium hydroxide and 14.5 g (0.1 g) of 4-chlorothiophenol is placed in a receiver. A suspension of 21 g (0.14 mol) of the monopotassium salt of acetylenedicarboxylic acid in 60 ml of water is dripped in and the mixture is heated to 100° C. After 45 minutes at this temperature the mixture is cooled to 0° C. and the pH is adjusted to 2 by adding concentrated hydrochloric acid. After suction filtration the solid is washed with water and dried under reduced pressure; yield: 17.6 g (68%) of colorless needles of m.p.222°–226° C.

The following compounds may be obtained analogously to this two-stage process:

TABLE A.2

| No. | Comp. I $R^1$ | $R^2$ | $R^3$ | m.p. [°C.] |
|---|---|---|---|---|
| 2.1 | H | H | H | 198 |
| 2.2 | $CO_2H$ | H | H | 233–236 |
| 2.3 | $CO_2H$ | H | 6-Cl | 140–145 |
| 2.4 | $CO_2H$ | H | 6-$CMe_3$ | <35 |
| 2.5 | $CO_2H$ | H | 8-$CO_2H$ | 150 |
| 2.6 | H | H | 6-$CMe_3$ | oil |

Example 3

2-Amino-4(1H)-oxothiochromene-3-carbonitrile 10 g (47 mmol) of 2-acetylmercaptobenzoic acid and 20 ml of oxalyl chloride are stirred in 50 ml of absolute toluene for 30 minutes at 100° C. The solution is evaporated down until a viscous oil remains. The oil is added in one portion to a stirred mixture of 7 g (106 mmol) of malonic dinitrile in 100 ml of 1% strength sodium hydroxide solution. After 5 minutes, a further 7 g (106 mmol) of malonic dinitrile and 5 ml of 20% strength sodium hydroxide solution are added. The mixture is stirred for 20 minutes, brought to an internal temperature of 50° C., and 5 g of potassium hydroxide (as a 50% strength aqueous solution) is added. The homogeneous mixture is brought, at 0° C., to a pH of 4 with concentrated hydrochloric acid, the solid is filtered off and dried under reduced pressure; yield: 6.5 g (68%) of beige-colored thiochromenone of melting point >240° C., active ingredient example 3.1.

Thiochromenones having different substitution patterns in the heterocyclic moiety may be prepared in similar manner:

TABLE A.3

| No. | Comp. I | | | m.p. [°C.] |
|---|---|---|---|---|
| | $R^1$ | $R^2$ | $R^3$ | |
| 3.1 | $NH_2$ | CN | H | >240 |
| 3.2 | $NH_2$ | $CO_2Et$ | H | 235 |
| 3.3 | OH | $CP_2Me$ | H | 217 |

An example for the functionalization of a thiochromenone is given below:

Example 4

2(4'-Chlorobenzoyl)amino-4(1H)-oxothiochromene-3-carbonitrile

A mixture of 5 g (25 mmol) of 2-amino-4(1H)-oxothiochromene-3-carbonitrile and 4 g (25 mmol) of 4-chlorobenzoyl chloride are stirred in 60 ml of absolute pyridine for 8 hours at the reflux temperature. The mixture is evaporated down in a rotary evaporator, and the residue is digested with water and suction filtered; yield: 4 g (47%) of a beige-colored solid of melting point >250° C., active ingredient example 4.5.

Similar acylations lead to:

TABLE A.4

| No. | Comp. I | | | m.p. [°C.] |
|---|---|---|---|---|
| | $R^1$ | $R^2$ | $R^3$ | |
| 4.1 | —NHCO—Me | CN | H | 130 (subst.) |
| 4.2 | —NHCO—$CHMe_2$ | CN | H | 180 |
| 4.3 | —NHCO—$CMe_3$ | CN | H | 155-160 |
| 4.4 | —NHCO—$(CH_2)_3$—Me | CN | H | 115 |
| 4.5 | —NHCO-p-Cl—$C_6H_4$ | CN | H | >250 |
| 4.6 | —NHCO-p-$NO_2$—$C_6H_4$ | CN | H | >250 |
| 4.7 | —NHCO-p-Me—$C_6H_4$ | CN | H | >238 |

Example demonstrating the biological action

The influence of various representatives of the herbicidal agents according to the invention, or combinations consisting of herbicide and safener, on the growth of crop and unwanted plants compared with the influence of the herbicidal agent on its own is demonstrated by the following examples from greenhouse experiments:

The vessels employed were plastic flowerpots having a volume of 300 cm$^3$ and filled with a sandy loam containing about 3.0wt % humus. The seeds of the test plants were sown separately, according to species, and then moistened. The vessels were then covered with transparent plastic lids until the seedlings had germinated and the plants had taken root.

| List of test plants | |
|---|---|
| Botanical name | Common name |
| Setaria viridis | green foxtail |
| Triticum aestivum | spring wheat |

-continued

| List of test plants | |
|---|---|
| Botanical name | Common name |
| Zea mays | corn |

For the postemergence treatment, the plants were grown, depending on growth form, to a height of 3 to 20 cm before being treated with the compounds, which were suspended or emulsified in water and sprayed through finely distributing nozzles.

The following cyclohexenone derivative II was used by way of example:

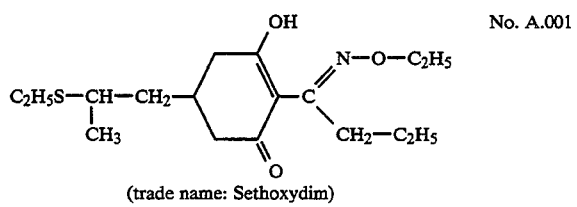

No. A.001

(trade name: Sethoxydim)

All safening compounds were formulated for postemergence treatment in a mixture consisting of 80wt % of cyclohexanone as diluent and 20wt % of a surfactant (Emulphor EL*)) containing 10wt % of active ingredient.

For comparison purposes, the herbicidal active ingredient was formulated as a 10 to 20wt % emulsion concentrate and used in the spray liquor together with that amount of solvent system with which the safeners were applied. The solvent was prepared by mixing the active ingredient with a solution of 93wt % of xylene and 7wt % of Lutensol AP-8**.

After the active ingredient mixtures had been applied, the test plants were cultivated in the greenhouse—heat-loving species at about 18° to 30° C., and those from milder climates at about 10° to 25° C.

The experiment was run for 3 to 5 weeks. During this period the plants were tended and their reactions to the treatments assessed.

The damage caused by the chemical agents was assessed on a 0 to 100% scale compared with untreated plants—0 denoting no damage and 100 complete destruction of the plants.

The improvement in the tolerance by crop plants from the Gramineae family, such as wheat and Indian corn, of herbicidal cyclohexenone derivatives II achieved by pyrido[2,3-d]pyrimidines I is apparent from the following Table B.1: *) ethoxylated castor oil **) nonionic surfactant based on alkylphenol polyethylene glycol ether

TABLE B.1

Improvement in the tolerance of the herbicide Sethoxydim by wheat as a result of the admixture of thiochromenone safeners; postemergence treatment in the greenhouse

| Safener Example No. | Application rate kg/ha | | Testplants and damage in % | |
|---|---|---|---|---|
| | Safener | Herbicide | Crop plant Wheat* | unwanted plant millet |
| — | — | 0.06 | 60 | 98 |
| — | — | 0.03 | 50 | 98 |
| 4.5 | 0.06 | 0.06 | 20 | 85 |
| | 0.03 | 0.03 | 10 | 90 |
| 4.1 | 0.06 | 0.06 | 50 | 100 |
| | 0.03 | 0.03 | 20 | 98 |
| 1.7 | 0.06 | 0.06 | 30 | 98 |
| | 0.03 | 0.03 | 0 | 98 |
| 1.13 | 0.06 | 0.06 | 40 | 98 |

TABLE B.1-continued

Improvement in the tolerance of the herbicide Sethoxydim by wheat as a result of the admixture of thiochromenone safeners; postemergence treatment in the greenhouse

| Safener Example No. | Application rate kg/ha Safener | Herbicide | Testplants and damage in % Crop plant Wheat* | unwanted plant millet |
|---|---|---|---|---|
| | 0.03 | 0.03 | 10 | 98 |
| 2.2 | 0.06 | 0.06 | 40 | 85 |
| | 0.03 | 0.03 | 10 | 75 |

*(Star)

We claim:

1. A herbicide containing at least one thiochromenone of the formula I

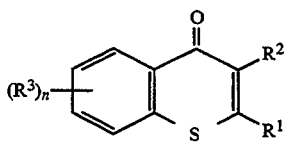

where n is 1, 2, 3 or 4, and the radicals $R^3$ may have different meanings when n is $>1$;

$R^1$ is hydrogen; cyano; halogen; unsubstituted or substituted alkyl, aryl or hetaryl;

$XR^4$ or $—COYR^4$, in which

X is oxygen, sulfur or $NR^5$,

Y is oxygen or $NR^5$, $R^4$ is one of the following groups:

hydrogen; formyl; alkyl; cycloalkyl; alkylcarbonyl; cycloalkylcarbonyl; alkylsulfonyl; cycloalkylsulfonyl; unsubstituted or substituted aryl, hetaryl, arylcarbonyl, hetarylcarbonyl, arylsulfonyl or hetarylsulfonyl, and $R^5$ is hydrogen or unsubstituted or substituted alkyl, aryl or hetaryl;

$R^2$ is hydrogen; cyano; nitroso; nitro; halogen; unsubstituted or substituted alkyl, alkoxy, alkylthio, aryl or hetaryl;

$—NR^4R^5$ or $—COYR^4$, in which

Y, $R^4$ an $R^5$ and have the abovementioned meanings;

$R^5$ is hydrogen; cyano; halogen; unsubstituted or substituted alkyl, aryl or hetaryl;

$—YR^4$, $—COYR^4$, $—COR^6$ or $—SO_2R^7$, in which

Y and $R^4$ have the abovementioned meanings;

$R^6$ is one of the following groups:

hydrogen; alkyl; cycloalkyl; unsubstituted or substituted aryl or hetaryl, and $R^7$ is hydrogen; alkyl; cycloalkyl; unsubstituted or substituted aryl or hetaryl, or $—NR^4R^5$ in which $R^4$ and $R^5$ have the abovementioned meanings, and the plant-tolerated salts of the compounds I in which one or more of the substituents is an acidic or basic group, and at least one herbicidally active ingredient selected from the group consisting of the cyclohexenone derivatives of the formula II

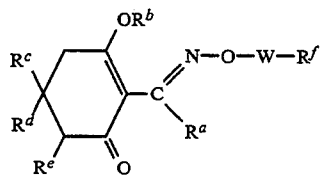

where $R^a$ is $C_1-C_6$-alkyl;

$R^b$ is hydrogen or one equivalent of an agriculturally suitable cation;

$R^c$ is $C_1-C_6$-alkyl, $C_1-C_4$-alkylthio-$C_1-C_6$-alkyl, $C_3-C_7$-cycloalkyl substituted by $C_1-C_4$-alkylthio, a 6-membered saturated heterocyclic structure which contains one oxygen or sulfur atom as heteroatom, or phenyl which may carry from one to three $C_1-C_4$-alkyl radicals;

$R^d$ is hydrogen or when $R^c$ is $C_1-C_6$-alkyl, $R^d$ is $C_1-C_6$-alkyl;

$R^e$ is hydrogen or $C_1-C_4$-alkoxycarbonyl;

W is a $C_1-C_6$ alkylene or $C_3-C_6$-alkenylene chain, which may carry one halogen atom;

a $C_3-C_6$-alkylene chain which may carry one $C_1-C_3$-alkyl radical and a methylene group of the chains may be substituted by oxygen; and $R^f$ is hydrogen or halophenyl.

2. A herbicide as claimed in claim 1, which contains a thiochromenone of the formula I as claimed in claim 1, where n is 1, 2, 3 or 4, and the radicals $R^3$ may have different meanings when n is $>1$;

$R^1$ is hydrogen; cyano; halogen; $C_5-C_{16}$-alkyl;

$C_1-C_4$-alkyl which may carry from one to five halogen atoms or one of the following radicals: hydroxyl, mercapto, $C_1-C_4$-alkoxy, $C_1-C_4$-alkylthio, phenyl, naphthyl, thienyl or pyridyl, where the aromatic radicals in turn may carry from one to five halogen atoms and from one to three of the following substituents: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, or where the aromatic radicals in turn may carry from one to five halogen atoms or from one to three of the following substituents: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

phenyl, naphthyl, thieny or pyridyl, where these aromatic radicals in turn may carry from one to five halogen atoms and from one to three of the following substituents: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, or where these aromatic radicals in turn may carry from one to five halogen atoms or from one to three of the following substituents: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

$—XR^4$ or $—COYR^4$, in which

X is oxygen, sulfur or $NR^5$,

Y is oxygen or $NR^5$, $R^4$ is one of the following groups: hydrogen; formyl; $C_1-C_{16}$-alkyl; $C_3-C_7$-cycloalkyl; $C_1-C_{16}$-alkylcarbonyl; $C_3-C_7$-cycloalkylcarbonyl; $C_1-C_{16}$-alkylsulfonyl; $C_3-C_7$-cycloalkylsulfonyl; phenyl, naphthyl, thienyl, pyridyl, phenylcarbonyl, naphthylcarbonyl, thienylcarbonyl, pyridylcarbonyl, phenylsulfonyl, naphthylsulfonyl, thienylsulfonyl or pyridylsulfonyl, where these aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where these aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, and $R^5$ is hydrogen or $C_1$-$C_{16}$-alkyl which may carry a hydroxyl or $C_1$-$C_4$-alkoxy group, or is phenyl, naphthyl, thienyl or pyridyl, where these aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where these aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

$R^2$ is hydrogen; cyano; nitroso; nitro; halogen; $C_5$-$C_{16}$alkyl;

$C_1$-$C_4$-alkyl, $C_1$-$C_4$-alkoxy or $C_1$-$C_4$-alkylthio, where these groups may carry from one to five halogen atoms or one of the following radicals: hydroxyl, mercapto, $C_1$-$C_4$-alkoxy, $C_1$-$C_4$-alkylthio, phenyl, naphthyl, thienyl or pyridyl, and where the aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where the aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

phenyl, naphthyl, thienyl or pyridyl, where these aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where these aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

—$NR^4R^5$ or —$COYR^4$, in which

Y, $R^4$ and $R^5$ have the abovementioned meanings;

$R^3$ is hydrogen; cyano; halogen; $C_5$-$C_{16}$-alkyl;

$C_1$-$C_4$-alkyl which may carry from one to five halogen atoms or one of the following radicals: hydroxyl, mercapto, $C_1$-$C_4$-alkoxy, $C_1$-$C_4$-alkylthio, phenyl, naphthyl, thienyl or pyridyl, and where the aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where the aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

phenyl, naphthyl, thienyl or pyridyl, where these aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where these aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

—$YR^4$, —$COYR^4$, —$COR^6$ or —$SO_2R^7$, in which

Y and $R^4$ have the abovementioned meanings;

$R^6$ is one of the following groups:

hydrogen; $C_1$-$C_{16}$-alkyl; $C_3$-$C_7$-cycloalkyl;

phenyl, naphthyl, thienyl or pyridyl, where these aromatic radicals in turn may carry from one to five halogen atoms and from one to three of the following substituents: $C_1$-$C_1$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where these aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

and $R^7$ is hydrogen; $C_1$-$C_{16}$-alkyl; $C_3$-$C_7$-cycloalkyl;

phenyl, naphthyl, thienyl or pyridyl, where these aromatic radicals in turn may carry from one to five halogen atoms and from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or where these aromatic radicals in turn may carry from one to five halogen atoms or from one to three of the following substituents: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, or —$NR^4R^5$, where $R^4$ and $R^5$ have the abovementioned meanings.

3. A herbicide as claimed in claim 1, which contains at least one thiochromenone of the formula I as claimed in claim 1, where n is 1 or 2.

4. A herbicide as claimed in claim 1, which contains at least one thiochromenone of the formula I as claimed in claim 1, where $R^1$ is hydrogen; halogen;

$C_1$- or $C_2$-alkyl which may carry from one to five halogen atoms or one of the following radicals: $C_1$- or $C_2$-alkoxy, $C_1$- or $C_2$-alkylthio, phenyl, naphthyl, thienyl or pyridyl, where the aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where the aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$- alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

—$XR^4$ or —$COYR^4$, in which

X and Y are each oxygen or $NR^5$, $R^4$ is one of the following groups:

hydrogen; $C_1$–$C_6$-alkyl; $C_3$–$C_7$-cycloalkyl;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_1$-alkoxy, $C_1$- or $C_2$-haloalkoxy, $C_1$- or $C_2$-alkylthio and $C_1$- or $C_2$-haloalkylthio, and $R^5$ is hydrogen or $C_1$–$C_6$-alkyl which may carry a hydroxyl or a $C_1$–$C_4$-alkoxy group.

5. A herbicide as claimed in claim 1, which contains at least one thiochromenone of the formula I as claimed in claim 1, where $R^2$ has the following meanings: hydrogen; halogen;

$C_1$- or $C_2$-alkyl, $C_1$- or $C_2$-alkoxy, or $C_1$- or $C_2$-alkylthio, where these groups may carry from one to five halogen atoms or one of the following radicals: $C_1$- or $C_2$-alkoxy, $C_1$- or $C_2$-alkylthio, phenyl, naphthyl, thienyl or pyridyl, where the aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where the aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

—$NR^4R^5$ or —$COYR^4$, in which

Y is oxygen or $NR^5$, $R^4$ is one of the following groups:

hydrogen; $C_1$–$C_6$-alkyl; $C_3$–$C_7$-cycloalkyl;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, and $R^5$ is hydrogen or $C_1$–$C_6$-alkyl which may carry a hydroxyl or a $C_1$–$C_4$-alkoxy group.

6. A herbicide as claimed in claim 1, which contains at least one thiochromenone of the formula I as claimed in claim 1, where $R^3$ has the following meanings: hydrogen; halogen;

$C_1$–$C_4$-alkyl which may carry from one to five halogen atoms or one of the following radicals: $C_1$- or $C_2$-alkoxy, $C_1$- or $C_2$-alkylthio, phenyl, naphthyl, thienyl or pyridyl, where the aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where the aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

—$YR^4$, —$COYR^4$, —$COR^6$ or —$SO_2R^7$, in which

Y is oxygen or $NR^5$, $R^4$ is one of the following groups:

hydrogen; $C_1$–$C_6$-alkyl; $C_3$–$C_7$-cycloalkyl;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

$R^5$ is hydrogen or $C_1$–$C_6$-alkyl which may carry a hydroxyl or a $C_1$–$C_4$-alkoxy group;

$R^6$ is one of the following groups:

hydrogen; $C_1$–$C_6$-alkyl; $C_3$–$C_7$-cycloalkyl;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

and $R^7$ is hydrogen; $C_1$–$C_6$-alkyl; $C_3$–$C_7$-cycloalkyl;

phenyl, naphthyl, thienyl or pyridyl, where these aromatic radicals in turn may carry from one to five halogen atoms and from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio, or where these aromatic radicals in turn may carry from one to five halogen atoms or from one to three of the following substituents: $C_1$- or $C_2$-alkyl, $C_1$- or $C_2$-haloalkyl, $C_1$- or $C_2$-alkoxy, $C_1$- or $C_2$-haloalkoxy, $C_1$- or $C_2$-alkylthio and $C_1$- or $C_2$-haloalkylthio;

or —$NR^4R^5$, where $R^4$ and $R^5$ have the abovementioned meanings.

7. A herbicide as claimed in claim 1, which contains at least one thiochromenone of the formula I as claimed in claim 1, where n is 1 or 2;

$R^1$ is hydrogen; halogen;

$C_1$- or $C_2$-alkyl which may carry from one to five halogen atoms or a $C_1$- or $C_2$-alkoxy group;

phenyl which may carry from one to five halogen atoms and from one to three of the following substituents: $C_1$- or $C_2$-alkyl, $C_1$- or $C_2$-alkoxy and $C_1$- or $C_2$-alkylthio, or where these aromatic radicals in turn may carry from one to five halogen atoms or from one to three of the following substituents: $C_1$- or $C_2$-alkyl, $C_1$- or $C_2$-alkoxy and $C_1$- or $C_2$-alkylthio;

—$XR^4$ and —$COYR^4$, in which

X and Y are each oxygen or $NR^5$, $R^4$ is one of the following groups:

hydrogen; $C_1$-$C_6$-alkyl; $C_3$-$C_7$-cycloalkyl;

phenyl which may carry from one to five halogen atoms and from one to three of the following substituents: $C_1$- or $C_2$-alkyl, $C_1$- or $C_2$-alkoxy and $C_1$- or $C_2$-alkylthio, or which may carry from one to five halogen atoms or from one to three of the following substituents: $C_1$- or $C_2$-alkyl, $C_1$- or $C_2$-alkoxy and $C_1$- or $C_2$-alkylthio, and $R^5$ is hydrogen or $C_1$-$C_6$-alkyl;

$R^2$ is hydrogen; halogen;

$C_1$- or $C_2$-alkyl or $C_1$- or $C_2$-alkoxy where these groups may carry from one to five halogen atoms or a $C_1$- or $C_2$-alkoxy radical;

phenyl which may carry from one to five halogen atoms and from one to three of the following substituents: $C_1$- or $C_2$-alkyl, $C_1$- or $C_2$-alkoxy and $C_1$- or $C_2$-alkylthio, or where these aromatic radicals in turn may carry from one to five halogen atoms or from one to three of the following substituents: $C_1$- or $C_2$-alkyl, $C_1$- or $C_2$-alkoxy and $C_1$- or $C_2$-alkylthio, —$NR^4R^5$ or —$COYR^4$, in which Y, $R^4$ and $R^5$ have the abovementioned meanings, $R^5$ is hydrogen; halogen;

$C_1$-$C_4$-alkyl which may carry from one to five halogen atoms or a $C_1$- or $C_2$-alkoxy radical;

—$YR^4$, —$COYR^4$, —$COR^6$ or —$SO_2R^7$, in which

Y and $R^4$ have the abovementioned meanings and $R^6$ and $R^7$ independently of one another are each $C_1$-$C_6$-alkyl; $C_3$-$C_7$-cycloalkyl;

phenyl which may carry from one to five halogen atoms and from one to three of the following substituents: $C_1$- or $C_2$-alkyl, $C_1$- or $C_2$-alkoxy and $C_1$- or $C_2$-alkylthio, or which may carry from one to five halogen atoms or from one to three of the following substituents: $C_1$- or $C_2$-alkyl, $C_1$- or $C_2$-alkoxy and $C_1$- or $C_2$-alkylthio.

8. A method for controlling undesirable plant growth, wherein at least one substituted thiochromenone of the formula I as defined in claim 1 and at least one cyclohexenone derivative of the formula I as defined in claim 1 are applied simultaneously or in succession, before, during or after sowing of crops or before or during emergence of the crops.

9. A method for selectively controlling undesirable plant growth, wherein the leaves of the crops and the undesirable plants are treated simultaneously or in succession, by the postemergence method, with at least one substituted thiochromenone of the formula I as defined in claim 1 and at least one cyclohexenone derivative of the formula II as defined in claim 1.

10. A method for preventing damage to crops by herbicidal cyclohexenone derivatives of the formula II as defined in claim 1, wherein the seed of the crops is treated with a thiochromenone of the formula I as defined in claim 1 in an amount which has an antagonistic action.

11. A method as claimed in claim 8, wherein the crops are barley, wheat, corn, millet or rice.

12. A method as claimed in claim 9, wherein the crops are barley, wheat, corn, millet or rice.

13. A method as claimed in claim 10, wherein the crops are barley, wheat, corn, millet or rice.

* * * * *

UNITED STATES PATENT AND TRADEMARK OFFICE
CERTIFICATE OF CORRECTION

PATENT NO.: 5,378,677

DATED: January 3, 1995

INVENTOR(S): HAGEN et al.

It is certified that error appears in the above-identified patent and that said Letters Patent is hereby corrected as shown below:

Column 81, claim 1, line 50, "$R^5$" should be --$R^3$--.

Signed and Sealed this

Second Day of May, 1995

Attest:

BRUCE LEHMAN

*Attesting Officer*     *Commissioner of Patents and Trademarks*